US007223408B2

(12) United States Patent
Cassetti et al.

(10) Patent No.: US 7,223,408 B2
(45) Date of Patent: May 29, 2007

(54) HUMAN PAPILLOMAVIRUS POLYPEPTIDES AND IMMUNOGENIC COMPOSITIONS

(75) Inventors: Maria Cristina Cassetti, Potomac, MD (US); Larry Smith, San Diego, CA (US); Jeffrey K. Pullen, New City, NY (US); Susan P. McElhiney, Hillburn, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/530,253

(22) PCT Filed: Oct. 2, 2003

(86) PCT No.: PCT/US03/31726

§ 371 (c)(1),
(2), (4) Date: Apr. 4, 2005

(87) PCT Pub. No.: WO2004/030636

PCT Pub. Date: Apr. 15, 2004

(65) Prior Publication Data

US 2006/0014926 A1    Jan. 19, 2006

Related U.S. Application Data

(60) Provisional application No. 60/415,929, filed on Oct. 3, 2002.

(51) Int. Cl.
*A61K 39/12* (2006.01)

(52) U.S. Cl. ............................... 424/204.1; 424/192.1; 435/6

(58) Field of Classification Search ............. 424/204.1, 424/192.1; 435/6
See application file for complete search history.

(56) References Cited

U.S. PATENT DOCUMENTS

| | | | |
|---|---|---|---|
| 5,719,054 A | 2/1998 | Boursnell et al. | |
| 6,004,557 A | 12/1999 | Edwards et al. | |
| 6,306,397 B1 | 10/2001 | Edwards et al. | |
| 6,365,160 B1 | 4/2002 | Webb et al. | |

FOREIGN PATENT DOCUMENTS

WO    WO 99/10375    *  3/1999

OTHER PUBLICATIONS

Von Knebel Doeberitz, M., et al., Inhibition of tumorigenicity of cervical cancer cells in nude mice by HPV E6-E7 anti-sense RNA, (1992) Int J Cancer 51, 831-4.
Crook, T., et al., Continued expression of HPV-16 E7 protein is required for maintenance of the transformed phenotype of cells co-transformed by HPV-16 plus EJ-ras, (1989) Embo J 8, 513-9.

He, Y., et al., Growth Inhibition of Human Papillomavirus 16 DNA-positive Mouse Tumor by Antisense RNA Transcribed from U6 Promoter, (1997) Cancer Res 57, 3993-9.
Smotkin, D., et al., Transcription of human papillomavirus type 16 early genes in a cervical cancer and a cancer-derived cell line and identification of the E7 protein, (1986) Proc Natl Acad Sci U S A 83, 4680-4.
Durst, M., et al., Human Papillomavirus Type 16 (HPV 16) Gene Expression and DNA Replication in Cervical Neoplasia: Analysis by in Situ Hybridization, (1992) Virology 189, 132-40.
Dyson, N., et al., The Human Papilloma Virus-16 E7 Oncoprotein Is Able to Bind to the Retinoblastoma Gene Product, (1989) Science 243, 934-7.
Cobrinik, D., et al., The Retinoblastoma protein and the regulation of cell cycling, (1992) Trends Biochem Sci 17, 312-5.
Scheffner, M., et al., The E6 Oncoprotein Encoded by Human Papillomavirus Types 16 and 18 Promotes the Degradation of p53, (1990) Cell 63, 1129-36.
Nakagawa, M., et al., Cytotoxic T Lymphocyte Responses to E6 and E7 Proteins of Human Papillomavirus Type 16: Relationship to Cervical Intraepithelial Neoplasia, (1997) J Infect Dis 175, 927-31.
Kadish, A. S., et al., Lymphoproliferative Responses to Human Papillomavirus (HPV) Type 16 Proteins E6 and E7: Outcome of HPV Infection and Associated Neoplasia, (1997) J Natl Cancer Inst 89, 1285-93.
Feltkamp, M. C., et al., Cytotoxic T lymphocytes raised against a subdominant epitope offered as a synthetic peptide eradicate human papillomavirus type 16-induced tumors, (1995) Eur J Immunol 25, 2638-42.
Lin, K. Y., et al., Treatment of Established Tumors with a Novel Vaccine That Enhances Major Histocompatibility Class II Presentation of Tumor Antigen, (1996) Cancer Res 56, 21-6.
Horton, R. M., et al., Engineering hybrid genes without the use of restriction enzymes: gene splicing by overlap extension, (1989) Gene 77, 61-8.
Pushko, P., et al., Replicon-Helper Systems from Attenuated Venezuelan Equine Encephalitis Virus: Expression of Heterologous Genes in Vitro and Immunization against Heterologous Pathogens In Vivo, (1997) Virology 239, 389-401.

(Continued)

*Primary Examiner*—Ali R. Salimi
(74) *Attorney, Agent, or Firm*—Darby & Darby

(57) ABSTRACT

The present invention provides immunogenic and pharmaceutical compositions for the treatment and prevention of human papillomavirus (HPV)-associated cancers and in particular, cervical cancer. In particular, this invention relates to fusion proteins, and the nucleic acids encoding these fusion proteins, used to generate immune responses against HPV. Specifically, this invention provides for fusions of HPV E6 and E7 in which the E6 and/or E7 contains one or more mutations. These mutations abrogate the transformation activity of these oncogenic proteins and, thus, confer safety to the E6/E7 fusions. In addition, these fusions maintain or increase the immunogenic efficacy of E6 and E7. Any gene or protein delivery method can be used to deliver or package the immunogenic compositions of the present invention.

10 Claims, 14 Drawing Sheets

OTHER PUBLICATIONS

Dalal, S., et al., Mutational Analysis of Human Papillomavirus Type 16 E6 Demonstrates that p53 Degradation Is Necessary for Immortalization of Mammary Epithelial Cells, (1996) J Virol 70, 683-8.

Shi, W., et al., Human Papillomavirus Type 16 E7 DNA Vaccine: Mutation in the Open Reading Frame of E7 Enhances Specific Cytotoxic T-Lymphocyte Induction and Antitumor Activity, (1999) J Virol 73, 7877-81.

Gao, Q., et al., Human Papillomavirus Type 16 E6-Induced Degradation of E6TP1 Correlates with Its Ability to Immortalize Human Mammary Epithelial Cells, (2001) J Virol 75, 4459-66.

Edmonds, C., et al., A Point Mutational Analysis of Human Papillomavirus Type 16 E7 Protein, (1989) J Virol 63, 2650-6.

Ressing, M. E., et al., Human CTL Epitopes Encoded by Human Papillomavirus Type 16 E6 and E7 Identified Through In Vivo and In Vitro Immunogenicity Studies of HLA-A*0201-Binding Peptides, (1995) J Immunol 154, 5934-43.

Ressing, M. E., et al., Occasional Memory Cytotoxic T-Cell Responses of Patients with Human Papillomavirus Type 16-positive Cervical Lesions against a Human Leukocyte Antigen-A*0201-restricted E7-encoded Epitope, (1996) Cancer Res 56, 582-8.

Evans, E. M., et al,. Infiltration of Cervical Cancer Tissue with Human Papillomavirus-specific Cytotoxic T-Lymphocytes, (1997) Cancer Res 57, 2943-50.

Rammensee, H. G., et al., Peptides Naturally Presented by MHC Class I Molecules, (1993) Annu Rev Immunol 11, 213-44.

Velders, M. P., et al., Eradication of Established Tumors by Vaccination with Venezuelan Equine Encephalitis Virus Replicon Particles Delivering Human Papillomavirus 16 E7 RNA, (2001) Cancer Res 61, 7861-7.

Boursnell, M.E.G, et al., Construction and characterization of a recombinant vaccinia virus expressing human papillomavirus proteins for immunotherapy of cervical cancer, (1996) Vaccine 14, 1485-1494.

Borysiewicz, L.K., et al., A recombinant vaccinia virus encoding human papillomavirus types 16 and 18, E6 and E7 proteins as immunotherapy for cervical cancer, (1996) The Lancet 347, 1523-27.

Gao, Q., et al., The E6 Oncoproteins of High-Risk Papillomaviruses Bind to a Novel Putative GAP Protein, E6TP1, and Target It for Degradation, (1999) Mol. and Cell. Biol. 19, 733-744.

De Jong, A., et al., Enhancement of human papillomavirus (HPV) type 16 E6 and E7-specific T-cell immunity in healthy volunteers through vaccination with TA-CIN, an HPV16 L2E7E6 fusion protein vaccine, (2002) Vaccine 20, 3456-3464.

Daemen, T., et al., Immunization strategy against cervical cancer involving an alphavirus vector expressing high levels of a stable fusion protein of human papillomavirus 16 E6 and E7, (2002) Gene Therapy 9, 85-94.

Fields Virology (2001) Fourth Edition, Ch. 65 and 66, pp. 2197-2264 Knipe & Howley Eds., Lippincott Williams and Wilkins.

Eiben GL et al., Establishment of an HLA-A*0201 Human Papillomavirus Type 16 Tumor Model to Determine the Efficacy of Vaccination Strategies in HLA-A0201 Transgenic Mice, Cancer Research, Oct. 15, 2002 vol. 62, No. 20 p. 5792-5799.

Engelhard, V. H., et al., Influenza A-Specific, HLA-A2.1-Restricted Cytotoxic T Lymphocytes From HLA-A2.1 Transgenic Mice Recognize Fragments of the M1 Protein, (1991) J Immunol 146, 1226-1232.

Shirai et al., CTL Responses of HLA-A2.1-Transgenic Mice Specific for Hepatitis C Viral Peptides Predict Epitopes for CTL of Humans Carrying HLA-A2.1, (1995) J Immunol 154, 2733-2742.

Zur Hausen, H., Papillomaviruses and Cancer: From Basic Studies to Clinical Application. Nat. Rev. Cancer, 2:342-350, 2002.

Walboomers, J. M., et al., Human Papillomavirus is a Necessary Cause of Invasive Cervical Cancer Worldwide. J. Pathol., 189:12-19, 1999.

Munger, K., et al., Biological Activities and Molecular Targets of the Human Papillomavirus E7 Oncoprotein. Oncogene, 20:7888-7898, 2001.

Wallin, K. L., et al., Type-Specific Persistence of Human Papillomavirus DNA Before the Development of Invasive Cervical Cancer. N. Eng. J. Med., 341:1633-1638, 1999.

Mantovanni, F., et al., The Human Papillomavirus E6 Protein and its Contribution to Malignant Progression. Oncogene, 20:7874-7887, 2001.

Eiben, G. L., et al., The Cell-Mediated Immune Response to Human Papillomavirus-Induced Cervical Cancer: Implications for Immunotherapy. Adv. Can. Res., 86:113-148, 2002.

Rayner, J. O., et al., Alphavirus Vectors and Vaccination. Rev. Med. Virol., 12:279-296, 2002.

Griffin, D. E., et al., Regulators of Apoptosis on the Road to Persistent Alphavirus Infection. Annu. Rev. Microbiol., 51:565-592, 1997.

Feltkamp, M. C. W., et al., Vaccination with Cytotoxic T Lymphocyte Epitope-Containing Peptide Protects Against a Tumor Induced by Human Papillomavirus Type 16-Transformed Cells. Eur. J. Immun. 23:2242-2249, 1993.

Grieder, F. B., et al., Specific Restrictions in the Progression of Venezuelan Equine Encephalitis Virus-Induced Disease Resulting from Single Amino Acid Changes in the Glycoproteins. Virology 206:994-1006, 1995.

Kast, W. M., Brandt, et al., Role of HLA-A Motifs Identification of Potential CTL Epitopes in Human Papillomavirus Type 16 E6 and E7 Proteins. J. Immunol., 152:3904-3912, 1994.

Ho, G. Y. F., et al., Natural History of Cervicovaginal Papillomavirus Infection in Young Women. N. Eng. J. Med., 338:423-428, 1998.

Daemen, T., et al., Eradication of Established Hpv16-Transformed Tumours after Immunisation with Recombinant Semliki Forest Virus Expressing a Fusion Protein of E6 and E7. Vaccine, 21:1082-1088, 2003.

Cheng, W. F., et al., Cancer Immunotherapy Using Sindbis Virus Replicon Particles Encoding a Vp22-Antigen Fusion. Hum. Gene Ther., 13:553-568, 2002.

MacDonald, G. H., et al., Role of Dendritic Cells Targeting Venezuelan Equine Encephalitis Virus Pathogenesis. J. Virol., 74:914-922, 2000.

Gardner, J. P., Frolov, et al., Infection of Human Dendritic Cells by a Sindbis Virus Replicon Vector is Determined by a Single Amino Acid Substitution in the E2 Glycoprotein. J. Virol. 74:11849-11857, 2000.

Nakagawa, M., Stites, et al., Persistence of Human Papillomavirus Type 16 Infection is Associated with Lack of Cytotoxic T Lymphocyte Response to the E6 Antigens. J. Inf. Dis., 182:595-598, 2000.

Welters, M. J. P., et al., Frequent Display of Human Papillomavirus Type 16 E6-Specific Memory T-Helper Cells in the Healthy Population as Witness of Previous Viral Encounter. Can. Res., 63:636-641, 2003.

Harrison's Principles of Internal Medicine (2001) Fifteenth Edition, p. 1119, Braunwald et al. Eds., McGraw-Hill.

Jewers et al., Regions of Human Papillomavirus Type 16 E7 Oncoprotein Required of Immortalization of Human Keratinocytes, (1992) J. Virol 66, p. 1329-1335.

Daemen et al., Genetic immunization against cervical carcinoma: induction of cytotoxic T lymphocyte activity with a recombinant alphavirus vector expressing human papillomavirus type 16 E6 asnd E7, (2000) Gene Therapy, 7, p. 1859-1866.

Longuet et al., Two Novel Genital Human Papillomavirus (HPV) Types, HPV68 and HPV70, Related to the Potentially Oncogenic HPV39, (1996) Journal of Clinical Microbiology, p. 738-744.

Mantovani et al., "The Human Papillomavirus E6 Protein and its Contribution to Malignant Progression," Oncogene, 2001, vol. 20, pp. 7874-7887.

Munger et al., "Biological Activities and Molecular Targets of the Human Papillomavirus E7 Oncoprotein," Oncogene, 2001, vol. 20, pp. 7888-7898.

Velders et al., "Eradication of Established Tumors by Vaccination with Venezuelan Equine Encephalitis Virus Replicon Particles Delivering Human Papillomavirus 16 E7 RNA," Cancer Research, Nov. 1, 2001, pp. 7861-7867.

\* cited by examiner

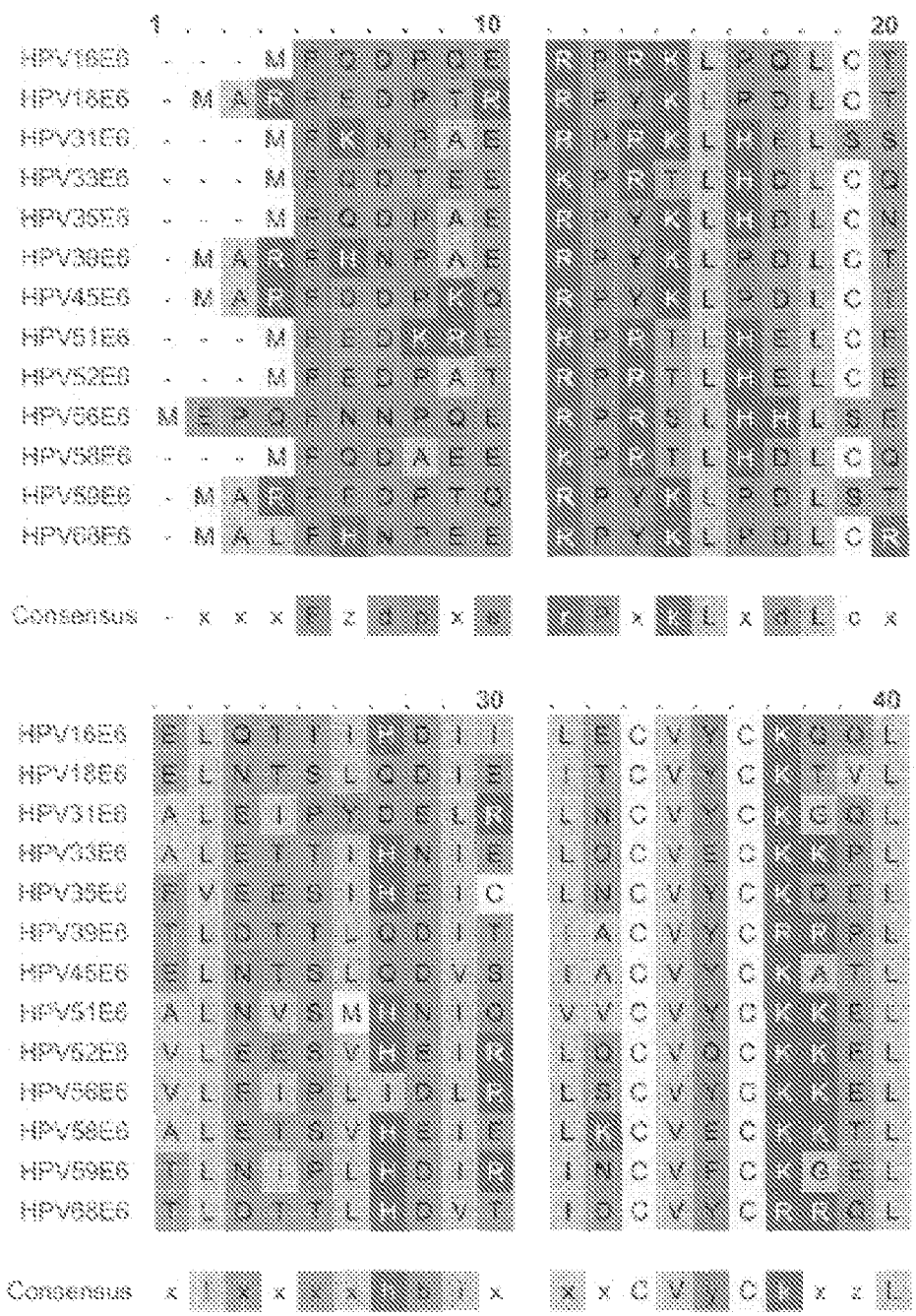

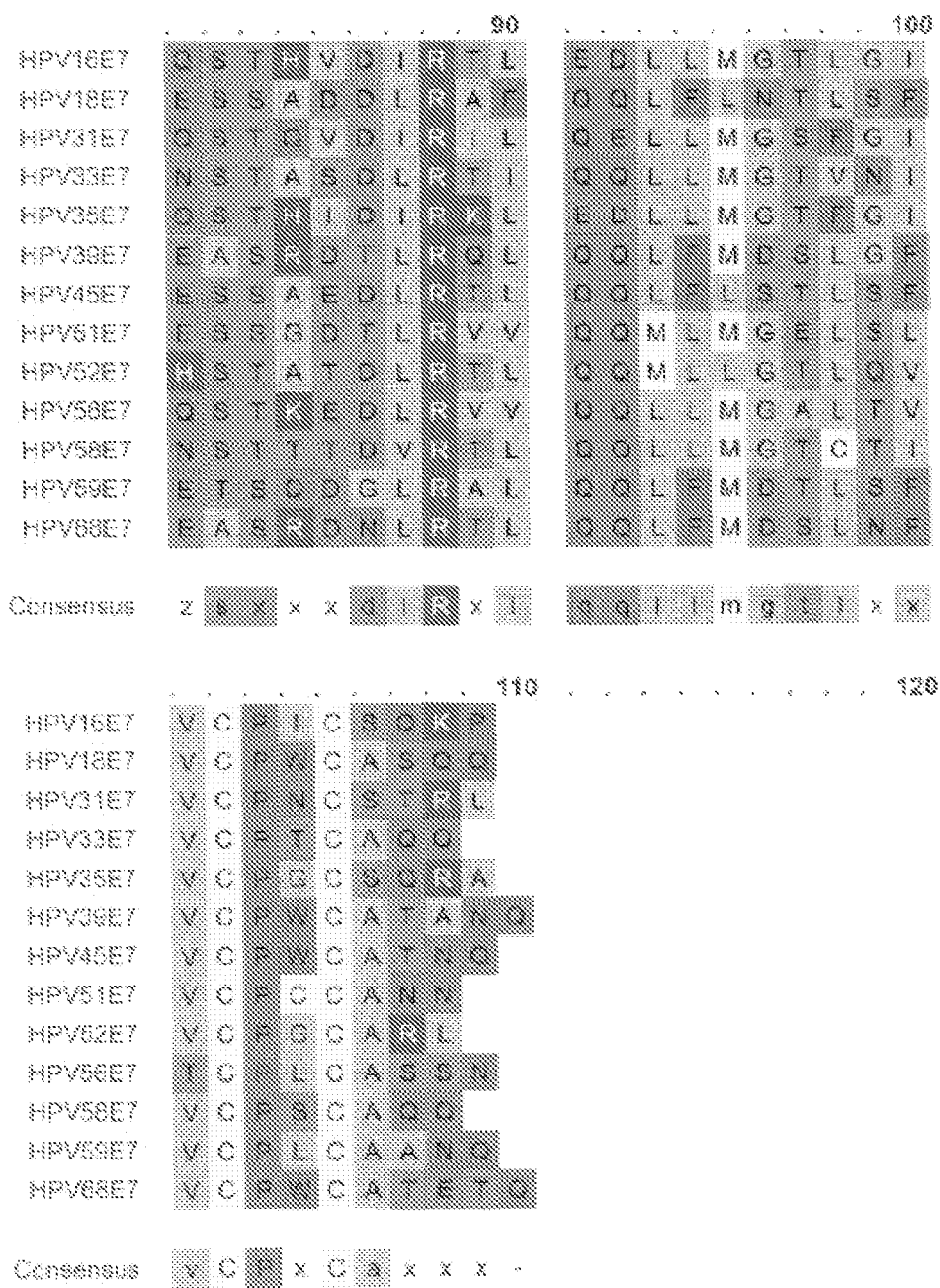

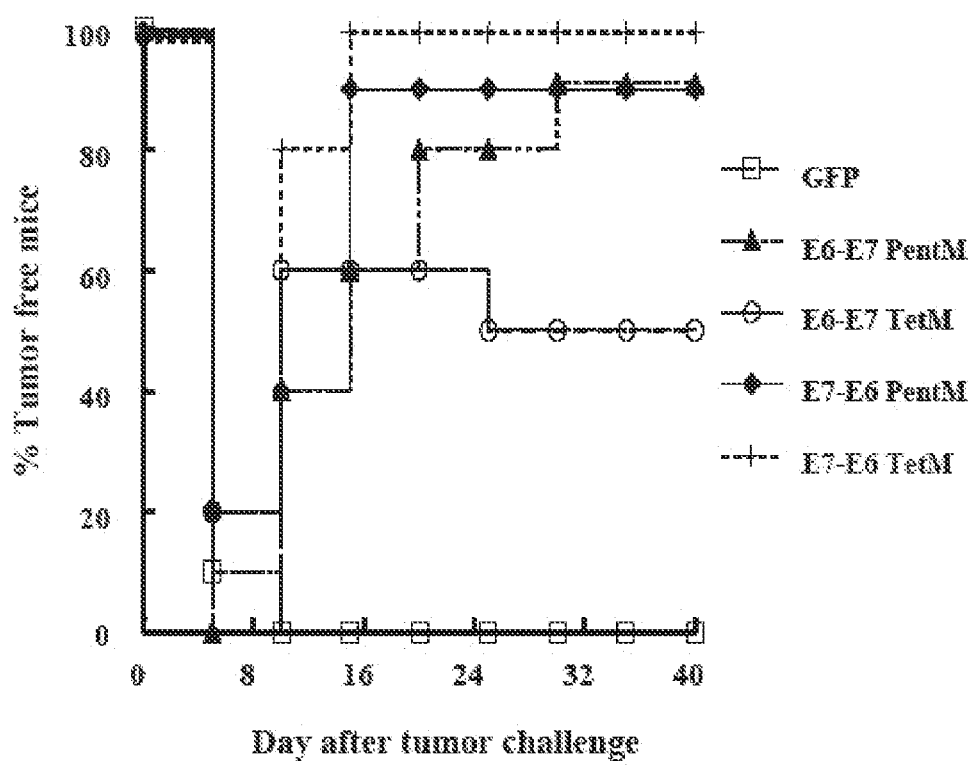

HUMAN PAPILLOMAVIRUS POLYPEPTIDES AND IMMUNOGENIC COMPOSITIONS

This application is a 371 National Phase of International Application No. PCT/US03/31726, filed Oct. 2, 2003, which claims priority to U.S. Provisional Patent Application Ser. No. 60/415,929, filed Oct. 3, 2002, both of which are incorporated herein by reference in their entireties.

FIELD OF THE INVENTION

This invention relates to pharmaceutical and immunogenic compositions used to treat or prevent cervical cancer and other cancers caused by human papillomaviruses (HPV). In particular, this invention relates to fusion proteins, and the nucleic acids encoding these fusion proteins, used to generate immune responses against HPV. These fusion proteins and polynucleotides are used in the treatment and prevention of HPV-induced cancers.

BACKGROUND OF THE INVENTION

Cancer of the uterine cervix is the second leading cause of tumor-related deaths in women, accounting for 250,000 deaths per year worldwide. Greater than 99% of all cervical cancers are known to be associated with human papillomavirus (HPV) infection, of which 50% are directly linked to HPV type 16 (HPV16) (Walboomers et al., J. Path. 1999, 189:12–19). While the majority of HPV16 infections are asymptomatic and transient, a certain percentage of them become persistent. About 1% of persistently infected individuals progress through increasingly severe cervical lesions known as cervical intraepithelial neoplasia (CIN), and eventially to invasive cervical carcinoma.

The early HPV proteins known as E6 and E7 are required to maintain the malignant phenotype (Von Knebel et al., Int J Cancer 1992, 51:831–4; Crook et al., Embo J 1989, 8:513–9; He and Huang, Cancer Res. 1997, 57:3993–9). These proteins are consistently expressed in CIN lesions and cancers (Smotkin and Wettstein, Proc Natl Acad Sci USA 1986, 83:4680–4; Durst et al., Virology 1992, 189:132–40). These proteins induce proliferation of the epithelium by disrupting the regulation of the cell cycle. Specifically, E7 binds and inactivates the cellular tumor suppressor retinoblastoma protein (Rb) (Dyson et al., Science 1989, 243: 934–7), which results in progression of the cell into S-phase of the cells cycle (Cobrinik et al., Trends Biochem Sci 1992, 17:312–5). The E6 protein of HPV16 induces degradation of the tumor suppression protein p53 (Scheffner et al., Cell 1990, 63:1129–36), preventing the cell from undergoing apoptosis.

Because tumor cells constitutively express the E6 and E7 proteins, and these proteins are not present in normal cells, these viral proteins are very attractive targets for cancer immune therapy. Many lines of evidence suggest that a cellular-mediated immune response against E6 and E7 in humans correlates with the natural regression of HPV lesions and viral DNA clearance (Nakagawa et al., J Infect Dis 1997, 175:927–31; Kadish et al., J Natl Cancer Inst 1997, 89:1285–93). Also a CTL response against E7 has been shown to protect mice against HPV16-positive tumors in different murine models (Feltkamp et al., Eur J Immunol 1995, 25:2638–42; Lin et al., Cancer Res 1996, 56:21–6).

Since cell-mediated immunity (CMI) appears important in controlling HPV infection and disease (Eiben, G. L. et al., Adv Can Res 2002, 86:113–148), a therapeutic vaccine should generate optimal T cell responses against numerous HPV E6 and E7 antigenic peptides for effective coverage in human leukocyte antigen (HLA) diverse populations.

A promising vaccine vector for delivering E6/E7 antigens is a recombinant alphavirus (AV) vector derived from the attenuated 3014 strain of Venezuelan equine encephalitis virus (VEE; Velders M. P. et al., Cancer Res 2001, 61:7861–7867). Replication incompetent VEE replicon particles (VRP) have proven to be highly effective vaccines in a number of preclinical infectious disease and tumor models (Rayner, J. O. et al., Rev Med Virol 2002, 12:279–296). AV-derived replicon vectors such as VEE encode heterologous genes in RNA form, do not spread beyond initial infection, and induce apoptosis of infected cells (Griffith, D. E. et al., Annu. Rev. Microbiol. 1997, 51:565–592). These attributes limit the opportunities for either prolonged protein expression or integration into host DNA which are characteristics of HPV-induced malignancies following natural infection. The low prevalence of pre-existing anti-VEE immunity and the prospects for repeated immunization with VRPs (Pushko, P. et al., Virology 1997, 239:389–401) are advantages over other recombinant viral vectors such as vaccinia virus or adenovirus.

Although attractive targets for cancer immune therapy, E6 and E7 have transforming activity. Consequently, immunotherapy methods using E6 and E7 that are currently contemplated in the art are potentially risky because these proteins can induce transformation and immortalization of cells.

There remains an unfulfilled need for efficacious compositions for the treatment and prevention of CIN and cervical carcinomal More specifically, there is a need for immunogenic compositions, including E6- and/or E7-based compositions, that are both safe and effective for treating end/or preventing CIN, cervical carcinoma, anal carcinoma, and other such disorders.

Previous studies of HPV immunogenic compositions have been limited by the lack of HLA class I expressing tumor models in mice. An HPV16 E6/E7 positive model is described herein; this model forms progressively growing tumors in HLA-A*0201 transgenic mice.

SUMMARY OF THE INVENTION

The present invention fulfills the above described and other needs by providing pharmaceutical compositions and polypeptides comprising fusions of E6 and E7 polypeptides bearing mutations and/or a fusion order (E7E6) that decreases the biological activity and therefore transforming activity potential of E6 and E7.

In particular, the present invention provides novel E6/E7 fusion polypeptides and the polynucleotides that encode them. In specific embodiments, the invention provides polypeptides comprising the human papillomavirus E6 and E7 polypeptides wherein the E7 polypeptide has mutations at any one or more of the amino acids corresponding to amino acids 24, 26 or 91 of SEQ ID NO: 14 and the E6 polypeptide has no mutations or has mutations at any one or more amino acids corresponding to amino acids 63 or 106 of SEQ ID NO: 13. In a specific embodiment, the fusion polypeptide comprises an E7 polypeptide in which one, or preferably both, of the amino acids corresponding to amino acids 24 and 26 of SEQ ID NO: 14 are mutated. These mutated polypeptides may have a glycine residue at any of these mutated positions and E6 may be carboxy terminal or amino terminal to E7.

The present invention also provides for isolated nucleic acids that encode these polypeptides. For example, in one embodiment of the invention the isolated nucleic acids comprise human papillomavirus E6 and E7 sequences wherein the E6 nucleotide sequence has mutations at any nucleotide(s) corresponding to nucleotides 187–189 or 316–318 of the HPV 16 E6 gene, and the E7 nucleotide sequence has mutations at any nucleotide(s) corresponding to nucleotides 70–72, 76–78 or 271–273 of the HPV 16 E7 gene, and wherein the mutation or mutations result in a different amino acid being encoded for. The present invention also provides pharmaceutical and immunogenic compositions comprising these polypeptides and polynucleotides.

The present invention also provides for isolated polypeptides having the amino acid sequence set forth in SEQ ID NO: 3, SEQ ID NO: 5, SEQ ID NO: 9, or SEQ ED NO: 11. In other embodiments, the invention provides isolated nucleic acids that encode such polypeptides, including nucleic acids having the nucleotide sequence SEQ ID NO: 4, SEQ ID NO: 6, SEQ ID NO: 10 or SEQ ID NO: 12.

Expression vectors comprising the nucleic acid sequences encoding E6/E7 fusions are also provided. For example, in a specific embodiment, the invention provides expression vectors comprising SEQ ID NOS: 4, 6, 10 or 12 operatively associated with (e.g., under the control of) an expression control sequence.

Host cells comprising nucleic acids encoding E6/E7 fusions are also provided, as well as host cells that express or contain the E6/E7 fusion polypeptides.

In still other embodiments, the invention also provides immunogenic compositions that comprise a nucleic acid or polypeptide of the invention and are useful, e.g., for treating or preventing cervical cancer. Such immunogenic compositions may comprise (a) a polypeptide of the invention (e.g., a polypeptide comprising the human papillomavirus E6 and E7 polypeptides wherein the E7 polypeptide has mutations at any one or more of the amino acids corresponding to amino acids 24, 26 or 91 of SEQ ID NO: 14 and the E6 polypeptide has no mutations or has mutations at any one or more amino acids corresponding to amino acids 63 or 106 of SEQ ID NO: 13), and (b) a pharmaceutically acceptable carrier. Optionally, an immunogenic composition of the invention may also contain an adjuvant.

Recombinant viruses are also provided that contain one or more nucleic acids of the invention, and/or encode one or more of the invention's polypeptides. Thus, for example, a recombinant virus of the invention may comprise a nucleic acid encoding a polypeptide as set forth in SEQ ID NOS: 3, 5, 9 or 11, and more particularly having the sequence set forth in any of SEQ ID NOS:4, 6, 10 or 12. In a particularly preferred embodiment, a recombinant virus of the invention is a modified Venezuelan equine encephalitis virus (VEEV).

Methods of using the above-mentioned compositions are additionally provided, and such methods are also considered part of the present invention. Thus, the invention also provides a method for producing an immune response in an individual by administering to that individual immunologically effective amounts of a polypeptide of the invention (e.g., one having the amino acid sequence set forth in any of SEQ ID NOS: 3, 5, 9 or 11) and a pharmaceutically effective carrier.

Methods for treating and/or preventing cervical cancer are also provided. For example, in one embodiment the invention provides methods for treating cervical cancer in which a patient diagnosed with cervical cancer is administered a polypeptide of the invention (e.g., one having the amino acid sequence set forth in any of SEQ ID NOS: 3, 5, 9 or 11) and a pharmaceutically acceptable carrier. In other embodiments, the invention provides methods for preventing cervical cancer in which a polypeptide of the invention and a pharmaceutically acceptable carrier are administered to an individual. In still other embodiments, the invention provides methods for treating and/or preventing cervical cancer in a patient by administering to the patient an immunologically effective amount of a nucleic acid of the invention (e.g., one having a nucleic acid sequence encoding a polypeptide having an amino acid sequence of SEQ ID NOS: 3, 5, 9, or 11, particularly set forth in any of SEQ ID NOS: 4, 6, 10 or 12).

BRIEF DESCRIPTION OF THE DRAWINGS

FIG. 1A shows the naturally occurring amino acids in E6, $^{63}$C and $^{106}$C, that were each mutated to glycine. FIG. 1B shows the naturally occurring amino acids in E7, $^{24}$C, $^{26}$E, and $^{91}$C, that were each mutated to glycine. Previously defined class I epitopes capable of binding HLA-A1, A2, A3, A11, and A24 alleles are shown in stippled boxes (Kast, W. M. et al., J Immunol 1994, 152:3904–3912).

FIGS. 2A–E are schematics showing the alignment and consensus sequence of the amino acid sequences of the E6 polypeptides of human papillomaviruses 18, 31, 33, 35, 39, 45, 51, 52, 56, 58, 59 and 68 (SEQ ID NOS: 15–26, respectively). The consensus sequence (SEQ ID NO: 39) is shown below the alignment. Capitalized letters in the consensus sequence indicate complete consensus and lowercase letters in the consensus sequence indicate high-frequency, but not complete consensus.

FIGS. 3A–C are schematics showing the alignment and consensus sequence of the amino acid sequences of the E7 polypeptides of human papillomaviruses 18, 31, 33, 35, 39, 45, 51, 52, 56, 58, 59 and 68 (SEQ ID NOS: 27–38, respectively). The consensus sequence (SEQ ID NO: 40) is shown below the alignment. Capitalized letters in the consensus sequence indicate complete consensus and lowercase letters in the consensus sequence indicate high-frequency, but not complete consensus.

FIG. 7 is a graph demonstrating percentage tumor free mice versus number of days after tumor challenge. HLA-A*0201 transgenic mice (n=10/gp) received 2×10$^6$ HLF16 tumor cells on day 0 and were immunized with the indicated VRP at days 5, 10, and 15. Tumors were monitored every 5 days.

Figure 8A:
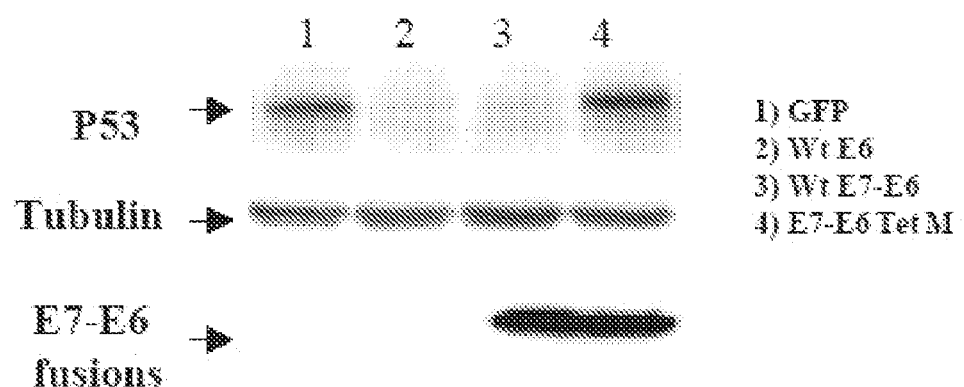
Figure 8B:
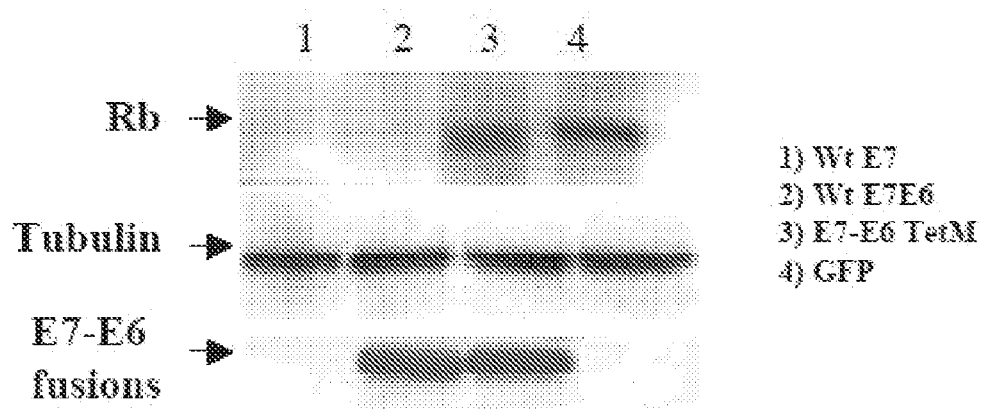

FIGS. 8A and 8B are Western blots detecting p53 (A) and Rb (B) expression in primary human mammary epithelial cells (MECs) infected with different VRP preparations. Twenty-four hours following infection with the indicated VRP (at MOI=10), 25 ug of each MEC cell lysate were run on SDS-PAGE, blotted, and probed for levels of p53 (A) and Rb (B). Equivalent protein loading was verified by probing with anti-tubulin antibody. The presence of E7 protein was verified by probing the indicated lanes with an anti-E7 antibody.

DETAILED DESCRIPTION OF THE INVENTION

The present invention provides for fusions of HPV E6 and E7 proteins, the nucleotide sequences encoding examples of such fusions, and mutant forms thereof. Although each of the specific mutations of HPV16 identified herewith (with the exception of E6 C106G, which had only previously been mutated to C106R (Dalal et al., J Virol 1996, 70:683–8)) has been previously disclosed, combinations of these mutations have not been made and combinations of these mutations have not been tested for their ability to retain immunogenicity while lacking transforming or immortalization capacity. For example, it was not known whether any other combinations of two or more mutations would result in polypeptides that maintained their immunogenic efficacy. The present invention discloses fusions of E6/E7 (the term "E6/E7" is used herein to indicate fusions in the order E6E7, E7E6 or both) proteins containing unique combinations of these mutations and the surprising finding that E6/E7 fusion proteins containing four or five defined mutations maintain their immunogenic efficacy. This finding is particularly important because a therapeutic immunogenic composition should generate optimal cellular responses against numerous HPV E6 and E7 antigenic peptides for effective coverage in HLA diverse populations. The present invention also discloses that these E6/E7 fusions bearing multiple mutations, while maintaining their immunological efficacy, do not maintain the functions necessary for E6's and E7's transforming capacity, namely p53 and pRB degradation. Specifically, the fusions of the present invention do not induce degradation of p53 or Rb and, thus, are safer than their non-mutant counterparts for delivery into or expression in a patient.

The present invention also discloses the surprising finding that E7E6 fusions, that is fusions in which E6 is carboxy terminal to E7, have increased immunological activity as compared to their E6E7 counterparts.

In specific examples, HPV16 E6E7 and E7E6 fusion proteins were produced and tested for immunogenicity and anti-tumor responses. Several point mutations were introduced into the E6 and E7 genes to inactivate their oncogenic potential, while preserving known HLA epitopes. Comparable CTL responses to the H-2D$^b$ restricted E7$_{49-57}$ epitope were observed among mice immunized with 3×10$^5$ infectious units of VRPs encoding wildtype or mutant fusion proteins. All of the wt and mutant fusion protein-expressing VRP immunogenic compositions eradicated 7 day-established C3 tumors in 90% or more of mice. In addition, E6E7 fusion constructs demonstrated anti-tumor efficacy in two other E6E7-positive tumor models. Specifically, E7E6 TetM VRPs conferred complete tumor rejection in the HLF16 tumor model. Primary human mammary epithelial cells infected with VRPs expressing mutant, but not wildtype, E6 and E7 genes demonstrated normal levels of both p53 and retinoblastoma proteins.

The E6E7 and E7E6 Fusions of the Invention

Figure 1A:
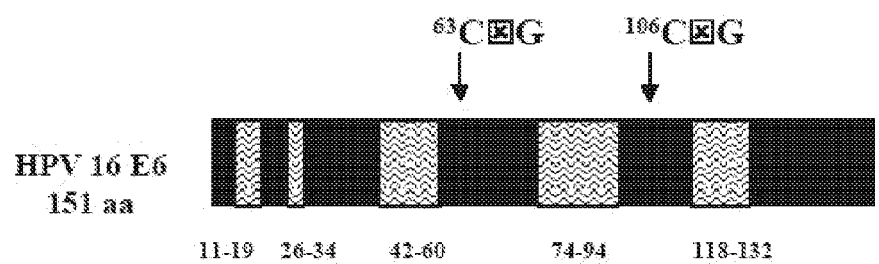
FIGS. 1A and 1B are schematic diagrams showing the location of the point mutations introduced into HPV16 E6 and E7 proteins in relation to putative epitopes for the major HLA-A Class I alleles.

The present invention provides for E6/E7 fusion polypeptides comprising multiple mutations, such as C24G, E26G and C91G in E7 and C63G and C106G in E6 (see FIGS. 1A and B). For example, the E6E7TetM and E7E6TetM fusion polypeptides comprise the E7 C24G and E26G mutations and the E6 C63G and C106G mutations, while the E6E7PentM and E7E6PentM fusion polypeptides comprise the C91G E7 mutation in addition to the four mutations present in the TetM mutants. These mutated fusion polypeptides, inter alia, may be unstable. Those of ordinary skill in the art appreciate that unstable proteins, as compared to stable proteins, have an increased capacity to develop CTL responses. Those skilled in the art will also appreciate that fusion proteins tend to not fold properly and thus are less stable than their non-fused counterparts. Thus, fusion proteins, such as those disclosed in the present invention, are better suited towards the production of cell-mediated immune responses than their unfused counterparts.

HPV16 E6E7 and E7E6 fusion proteins were produced and tested for immunogenicity and anti-tumor responses. Several point mutations were introduced into the E6 and E7 genes to inactivate their oncogenic potential, while preserving known HLA epitopes. Prior to the present invention it was not known whether the combinations of the mutations tested herein would destroy the polypeptides' immunogenicity or whether such mutated polypeptides would retain their immunogenicity. Comparable CTL responses to the H-2D$^b$ restricted E7$_{49-57}$ epitope were observed among mice immunized with 3×10$^5$ infectious units of VRPs encoding wild type or mutant fusion proteins. All of the wild type and mutant fusion protein-expressing VRP immunogenic compositions eradicated 7 day-established C3 tumors in 90% or more of mice. In addition, E6/E7 fusion constructs demonstrated anti-tumor efficacy in two other E6E7-positive tumor models.

The present invention provides fusion polypeptides comprising E6 and E7, in which E6 is either at the amino terminus or at the carboxy terminus. However, those skilled in the art will recognize from the instant disclosure that fusions in which E6 is carboxy terminal to E7 (E7E6 fusions), that is E6 follows E7, such as E7E6TetM and E7E6PentM, will have increased immunological efficacy as compared to fusions in which E6 is amino terminal to E7 (E6E7 fusions, such as E6E7TetM and E6E7PentM). In addition, it will be recognized by those skilled in the art that E7E6 fusions, that is fusions in which E6 is carboxy terminal to E7, will have decreased E6 activity as compared to E6E7 fusions. Thus, E7E6 fusions will generally be expected to be safer. Accordingly, fusions in which E6 is carboxy terminal to E7 are a more preferred embodiment of the present invention.

The present invention provides examples of particular nucleotide and amino acid mutations at positions corresponding to C24, E26 and C91 of HPV16 E7 and C63 and C106 of HPV16 E6. For example, the present invention provides cysteine 24 to be mutated to glycine (the corresponding mutation in the nucleotide sequence is CTG to CGG). These examples are not limiting. For example, mutations that similarly resulted in disruption of the zinc fingers or Rb binding can be used. For example, mutations at cysteine residues important for zinc finger formation can be changed to any other amino acid. Preferred mutations result in a destabilization of the protein and thus, an increase in the immunogenicity of the protein.

In a specific embodiment of the invention, the polypeptides are fusions of HPV16 E6 and E7 in which the E7 polypeptide has mutations at any amino acid(s) corresponding to positions 24, 26 or 91 of SEQ ID NO: 14 and the E6 polypeptide has either no mutations or has mutations at one or more amino acid(s) corresponding to positions 63 or 106 of SEQ ID NO: 13. In a preferred embodiment of the invention, the polypeptides are fusions of HPV16 E6 and E7 in which the E7 polypeptide has mutations at amino acids corresponding to positions 24 and 26 of SEQ ID NO: 14 and the E6 polypeptide has mutations selected from the group consisting of amino acids corresponding to positions 63 or 106 of SEQ ID NO: 13 or both.

It is understood in the art the the amino acid number is determined by counting methionine as the first amino acid, even in the case where the first methionine has been deleted in the second of the fusion proteins. For example, the G24 mutation of E6E7TetM (SEQ ID NO: 3) is considered to be at residue 24 of E7 in the polypeptide.

In another preferred embodiment of the present invention, the polynucleotides are fusions of HPV16 E6 and E7 polynucleotides in which the E6 polynucleotide has mutations at any of nucleotides 187–189 (which corresponds to nucleotides 290–292 of the HPV16 genome (GenBank accession number K02718)) or 316–318 (which corresponds to nucleotides 419–421 of the HPV16 genome), and the E7 nucleotide sequence has mutations at any of nucleotides 70–72 (which corresponds to nucleotides 631–633 of the HPV16 genome), 76–78 (which corresponds to nucleotides 637–639 of the HPV16 genome) or 271–273 (which corresponds to nucleotides 832–834 of the HPV16 genome). These nucleotide changes result in missense mutations, not nonsense mutations. In other words, these mutations result in a different amino acid being encoded.

The present invention provides polypeptides, and immunogenic and pharmaceutical compositions comprising these polypeptides, or comprising nucleotides encoding these polypeptides. As described infra these polypeptides and polynucleotides are described in the sequences provided herein. For example, the E6E7TetM polypeptide is described in SEQ ID NO: 3. Those skilled in the art will appreciate that the polypeptide and polynucleotide sequences of this invention are not limited to the exact sequences disclosed in this application. For example, the E6 and E7 sequences were obtained by performing PCR from the ATCC clone #45113 of HPV16. The E6 and E7 sequences of this ATCC clone vary slightly from those in the GenBank HPV16 sequence, K02718. Thus, those skilled in the art will appreciate that the invention also comprises substantially homologous or substantially similar amino acid and nucleotide sequences to those disclosed herewith and that the combination of mutations described can occur in the background of any E6 or E7 sequence. For example, these mutations and any number of combinations of these mutations can be in the context of the E6 and E7 sequences disclosed in K02718.

Those skilled in the art will appreciate that this invention can also be drawn to the other members of the papillomaviral family in addition to HPV16. Other papillomavirus genotypes associated with cancer, in particular, 18, 31, 33, 35, 39, 45, 51, 52, 56, 58, 59 and 68 have conserved motifs in their E6 and E7 proteins that are likely central to their oncogenic capacity (see Fields Virology Fourth Edition, 2001, Ch. 65 and 66, 2197–2265, Knipe & Howley Eds., Lippincott Williams and Wilkins). Notably, these E6 and E7 proteins have C-X-X-C zinc finger motifs and, for E7, a putative Rb binding motif L-X-C-X-E. Thus, an embodiment of the present invention comprises E6 and E7 fusion polypeptides and polynucleotides from other members of the papillomavirus family, which have mutations that correspond with the mutations disclosed in the present invention.

Amino acids and nucleotides that correspond to the positions of the particular amino acids and nucleotides disclosed in SEQ ID NOS: 1–12 can be determined by performing a sequence alignment. Examples of such sequence alignments are shown in FIGS. 2A–E and 3A–C. In these figures, the amino acids of the E6 and E7 polypeptides of HPVs 18, 31, 33, 35, 39, 45, 51, 52, 56, 58, 59 and 68 have been aligned, and consensus sequences are presented. The E6 consensus amino acid sequence is represented in SEQ ID NO: 39 and the E7 consensus amino acid sequence is represented in SEQ ID NO: 40.

These alignments demonstrate that the each of the mutations tested in the present invention are conserved in each of these HPV viruses and, thus, they too can be mutated in order to knock-out their oncogenic potential, while maintaining their ability to elicit an immune response. Amino acids that are involved in the formation of structures such as zinc fingers and binding motifs are often conserved. One can, for example, identify and mutate the conserved amino acids or nucleotides that correspond to amino acids 24, 26, and 91 of HPV16's E7 and to amino acids 63 or 106 of HPV16's E6 in each of the members of the HPV genotypes. For example, the alignment shown in FIGS. 2A–E demonstrates that the HPV18 E6 amino acid that corresponds to amino acid 63 of HPV16 E6 ($^{63}$C) is also a cysteine residue and that it is at position 65 of HPV18's E6. Accordingly, $^{66}$C of HPV18's E6, in addition to other residues that correspond to amino acids 24, 26, and 91 of HPV16's E7 and to amino acid 106 of HPV16's E6, can be mutated in the present invention. Similarly, mutations in any HPV E6 polypeptide corresponding to amino acids 65 or 108 of the E6 consensus sequence (SEQ ID NO: 39) or in any HPV E7 polypeptide corresponding to amino acids 25, 27 or 97 of the E7 consensus sequence (SEQ ID NO: 40) can be made in the present invention.

In one embodiment of the present invention, the fusion polypeptides comprise two of these mutations. In a further embodiment, these fusion polypeptides comprise three of these mutations. In another embodiment, these fusion polypeptides comprise four of these mutations. In yet another embodiment, these fusion polypeptides comprise all five of these mutations.

Molecular Biology Definitions. In accordance with the present invention, there may be employed conventional molecular biology, microbiology and recombinant DNA techniques within the skill of the art. Such techniques are explained fully in the literature. See, for example, Sambrook, Fitsch and Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames and S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

The polynucleotides herein may be flanked by natural regulatory sequences, or may be associated with heterologous sequences, including promoters, enhancers, response elements, signal sequences, polyadenylation sequences, introns, 5'- and 3'-non-coding regions and the like. The nucleic acids may also be modified by many means known in the art. Non-limiting examples of such modifications include methylation, "caps", substitution of one or more of the naturally occurring nucleotides (i.e., codon optimization of the third or initial "wobble" base), and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like. Other non-limiting examples of modification which may be made are provided, below, in the description of the present invention.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. Preferably, the coding sequence is an RNA sequence that is translated into a polypeptide in a cell in vitro or in vivo when placed under the control of appropriate regulatory sequences. The boundaries of the coding sequence are determined by a start codon near the 5' terminus and a downstream translation stop codon. A coding sequence can include, but is not limited to, prokaryotic sequences, cDNA from eukaryotic mRNA, genomic DNA sequences from eukaryotic (e.g., mammnalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences. "Expression control sequences" are the transcriptional control sequences involved in the initiation of transcription, such as promoters and enhancers.

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background. As described above, promoter DNA is a DNA sequence which initiates, regulates, or otherwise mediates or controls the expression of the coding DNA.

Amplification of a polynucleotide, as used herein, denotes the use of polymerase chain reaction (PCR) to increase the concentration of a particular DNA sequence within a mixture of DNA sequences. For a description of PCR see Saiki et al., Science 1988, 239:487.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence, which may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", and "expression vector" mean the vehicle by which a DNA or RNA sequence (e.g. a foreign gene) can be introduced into a host cell, so as to transform the host and promote expression of a polypeptide (e.g. transcription and translation) of the introduced sequence.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the trnsrmissible vector DNA. A segment or sequence of DNA having inserted or added DNA, such as an expression vector, can also be called a "DNA construct."

A common type of vector is a "plasmid", which generally is a self-contained molecule of double-stranded DNA. A plasmid can readily accept additional (foreign) DNA and which can readily be introduced into a suitable host cell. A plasmird vector often contains coding DNA and promoter DNA and has one or more restriction sites suitable for inserting foreign DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Routine experimentation in biotechnology can be used to determine which cloning vectors are best suited for used with the invention. In general, the choice of cloning vector depends on the size of the polynucleotide sequence and the host cells to be used.

A "polypeptide" is a chain of chemical building blocks called amino acids that are linked together by chemical bonds called "peptide bonds." The term "protein" refers to polypeptides that contain the amino acid residues encoded by a gene or by a nucleic acid molecule (e.g., an mRNA or a cDNA) tanscribed from that gene either directly or indirectly. Optionally, a protein may lack certain amino acid residues that are encoded by a gene or by an mRNA. A protein or polypeptide, including an enzyme, may be a "native" or "wild-type," meaning that it occurs in nature; or it may be a "mutant," "variant" or "modified," meaning that it has been made, altered, derived, or is in some way different or changed from a native protein or from another mutant.

"Mutation" means any process or mechanism resulting in a mutant protein, enzyme, polypeptide, polynucleotide, gene, or cell. This includes any mutation in which a protein, enzyme, polynucleotide, or gene sequence is altered, and any detectable change in a cell arising from such a mutation. The altered protein, enzyme, polypeptide or polynucleotide is a "mutant," also called a "variant." Typically, a mutation occurs in a polynucleotide or gene sequence, by point mutations (substitutions), deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent," i.e., not reflected in an amino acid alteration upon expression, leading to a "sequence-conservative" variant of the gene. This generally arises when one amino acid corresponds to more than one codon. Table 1 outlines which amino acids correspond to which codon(s).

Thus, due to the degeneracy of the genetic code, any three-nucleotide codon that encodes a mutated amino acid residue of an E6/E7 fusion polypeptide described herein is within the scope of the invention.

The terms "mutant" and "variant" may also be used to indicate a modified or altered gene, DNA or RNA sequence, enzyme, cell, etc., i.e., any kind of mutant. Such changes also include changes in the promoter, ribosome binding site, etc.

The term "variant amino acid sequences" refers to other suitable E6 and E7 fusion polypeptides which can differ from the specifically exemplified E6 and E7 fusion polypeptides by modifications which do not diminish immunogenicity. In making such changes, the hydropathic index of amino acids can be considered. The importance of the hydropathic amino acid index in conferring interactive biologic function on a polypeptide is generally understood in the art (Kyte and Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those within +/−1 are particularly preferred, and those within +/−0.5 are even more particularly preferred.

Substitution of like amino acids can also be made on the basis of hydrophilicity, particularly where the biologically functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0 +/−1); glutamate (+3.0 +/−1); serine (+0.3); asparagine (+0.2); glutamine (+0.2); glycine (0); proline (−0.5+/−1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within +/−2 is preferred; those within +/−1 are particularly preferred; and those within +/−0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

"Function-conservative variants" are proteins or enzymes in which a given amino acid residue has been changed without altering the overall structural conformation and specified function of the protein or enzyme. This includes but is not limited to, replacement of an amino acid with one having sumilar structural or physical properties, including polar or non-polar character, size, shape and charge (see, e.g., Table 1).

TABLE 1

Amino Acids, Corresponding Codons, and Functionality/Property

| Amino Acid | SLC | DNA codons | Side Chain Property |
|---|---|---|---|
| Isoleucine | I | ATT, ATC, ATA | Hydrophobic |
| Leucine | L | CTT, CTC, CTA, CTG, TTA, TTG | Hydrophobic |
| Valine | V | GTT, GTC, GTA, GTG | Hydrophobic |
| Phenylalanine | F | TTT, TTC | Aromatic side chain |
| Methionine | M | ATG | Sulfur group |
| Cysteine | C | TGT, TGC | Sulfur group |
| Alanine | A | GCT, GCC, GCA, GCG | Hydrophobic |
| Glycine | G | GGT, GGC, GGA, GGG | Hydrophobic |
| Proline | P | CCT, CCC, CCA, CCG | Secondary amine |
| Threonine | T | ACT, ACC, ACA, ACG | Aliphatic hydroxyl |
| Serine | S | TCT, TCC, TCA, TCG, AGT, AGC | Aliphatic hydroxyl |
| Tyrosine | T | TAT, TAC | Aromatic side chain |
| Tryptophan | W | TGG | Aromatic side chain |
| Glutamine | Q | CAA, CAG | Amide group |
| Asparagine | N | AAT, AAC | Amide group |
| Histidine | H | CAT, CAC | Basic side chain |
| Glutamic acid | E | GAA, GAG | Acidic side chain |
| Aspartic Acid | D | GAT, GAC | Acidic side chain |
| Lysine | K | AAA, AAG | Basic side chain |
| Arginine | R | CGT, CGC, CGA, CGG, AGA, AGG | Basic side chain |
| Stop codons | Stop | TAA, TAG, TGA | — |

As referred to herein, "sequence similarity" means the extent to which nucleotide or protein sequences are related. The extent of similarity between two sequences can be based on percent sequence identity and/or conservation. Amino acids other than those indicated as conserved may differ in a protein or enzyme so that the percent protein or amino acid sequence similarity between any two proteins of similar function may vary and can be, for example, at least 70%, even more preferably 80%, and most preferably at least 90%, as determined according to an alignment scheme.

"Sequence identity" herein means the extent to which two nucleotide or amino acid sequences are invariant.

Two DNA sequences are substantially homologous or substantially similar when at least about 80%, and most preferably at least about 90 or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, two amino acid sequences are substantially homologous or substantially similar when greater than 80% of the amino acids are identical, or greater than about 90% are similar. Preferably, the similar or homologous sequences are identified by sequence alignment.

"Sequence-conservative variants" of a polynucleotide sequence are those in which a change of one or more nucleotides within a given codon results in no alteration in the amino acid encoded by that codon.

"Sequence alignment" means the process of lining up two or more sequences to achieve maximal levels of sequence identity (and, in the case of amino acid sequences, conservation), e.g., for the purpose of assessing the degree of sequence similarity. Numerous methods for aligning sequences and assessing similarity and/or identity are known in the art such as, for example, the Cluster Method, wherein similarity is based on the MEGALIGN algorithm, as well as BLASIN, BLASTP, and FASTA (Lipman and Pearson, 1985; Pearson and Lipman, 1988). When using all of these programs, the preferred settings are those that result in the highest sequence similarity.

The term "heterologous" refers to a combination of elements not naturally occurring. For example, heterologous DNA refers to DNA that is not naturally located in the cell, or in a chromosomal site of the cell. Preferably, heterologous DNA includes a gene foreign to the cell. A heterologous expression regulatory element is a regulatory element operatively associated with a different gene that the one it is operatively associated with in nature.

Modifications, which do not normally alter the primary sequence of the E6 and E7 fusion polypeptides, include in vivo or in vitro chemical derivatization of polypeptides, e.g., acetylation, methylation, or carboxylation. Also included as variant polypeptides of this invention are these polypeptides modified by glycosylation, e.g., those made by modifying the glycosylation patterns of a polypeptide during its synthesis and processing or in further processing steps; or by exposing the polypeptide to enzymes which affect glycosylation, such as mammalian glycosylating or deglycosylating enzymes. Also embraced as variant polypeptides are the above-identified mutagenized sequences, which have phosphorylated amino acid residues, e.g., phosphotyrosine, phosphoserine, or phosphothreonine.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived there from can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

Polynucleotides are "hybridizable" to each other when at least one stand of one polynucleotide can anneal to another polynucleotide under defined stringency conditions. Stringency of hybridization is determined, e.g., by the temperature at which hybridization and/or washing is performed, and b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that "hybridize" to the polynucleotides herein may be of any length. In one embodiment, such polynucleotides are at least 10, preferably at least 15 and most preferably at least 20 nucleotides long. In another embodiment, polynucleotides that hybridize are of about the same length. In another embodiment, polynucleotides that hybridize include those which anneal under suitable stringency conditions and which encode polypeptides or enzymes having the same function, such as the ability to bind p53 (in the case of E6)or bind Rb (in the case of E7).

The general genetic engineering tools and techniques discussed here, including transformation and expression, the use of host cells, vectors, expression systems, etc., are well known in the art.

As used herein, the term "about" or "approximately" means within 50% of a given value, preferably within 20%, more preferably within 10%, more preferably still within 5%, and most preferably within 1% of a given value. Alternatively, the term "about" or "approximately" means that a value can fall within a scientifically acceptable error range for that type of value, which will depend on how qualitative a measurement can be given the available tools. "About" or "approximately" may define a distribution around a mean value, rather than a single value.

The Immunogenic and Pharmaceutical Compositions of the Invention

The present invention provides immunogenic and pharmaceutical compositions comprising fusion polypeptides and polynucleotides of human papillomavirus E6 and E7. These compositions can be used to treat and/or prevent papillomavirus-induced cancers, such as cervical cancer, and cervical lesions such as CIN. These compositions can also be used to treat lower gastrointestinal tract cancers, such as anal cancer, and other cancers of the reproductive system, such as penile and vulvar cancer.

Figure 3A:
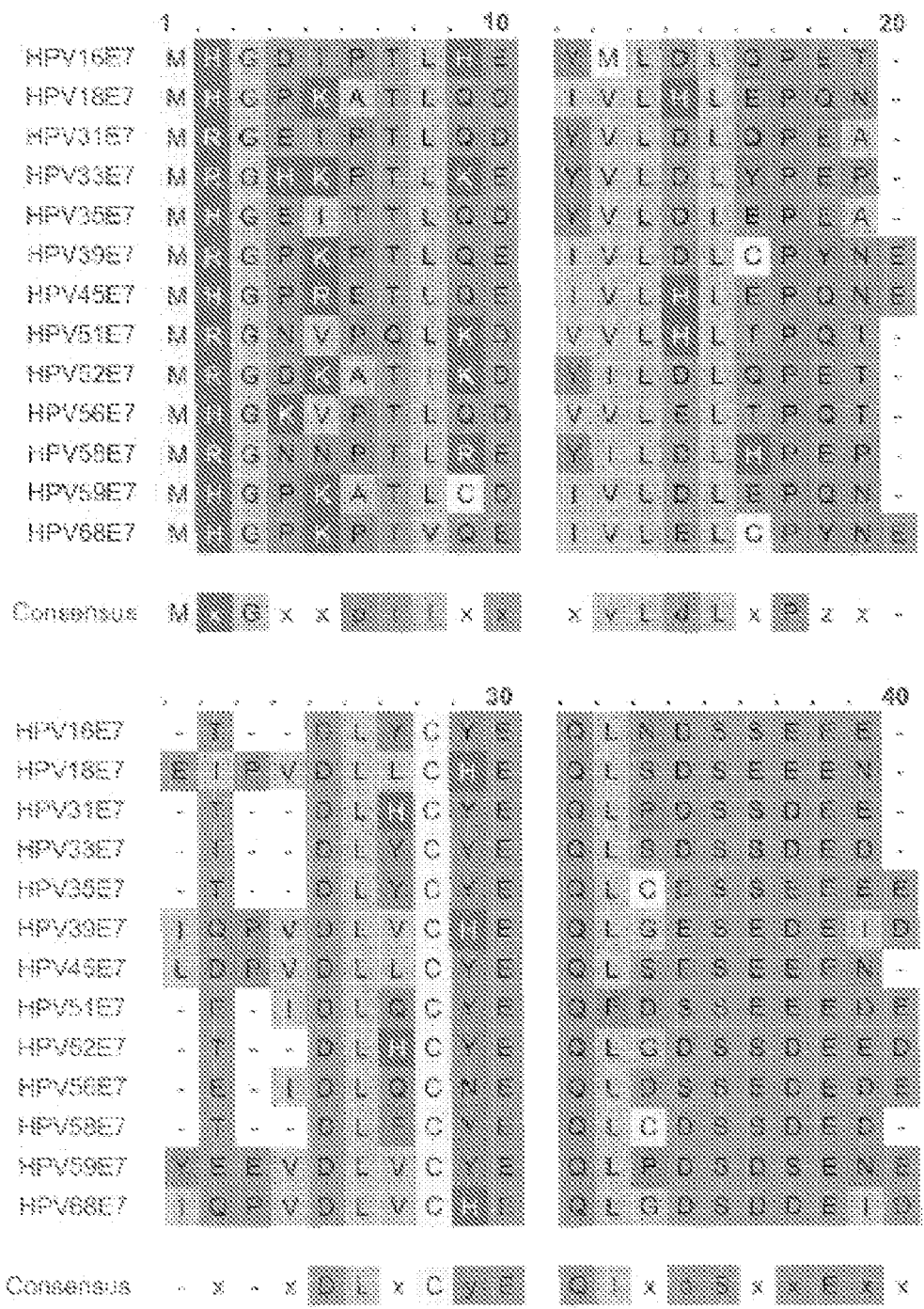
Figure 3B:
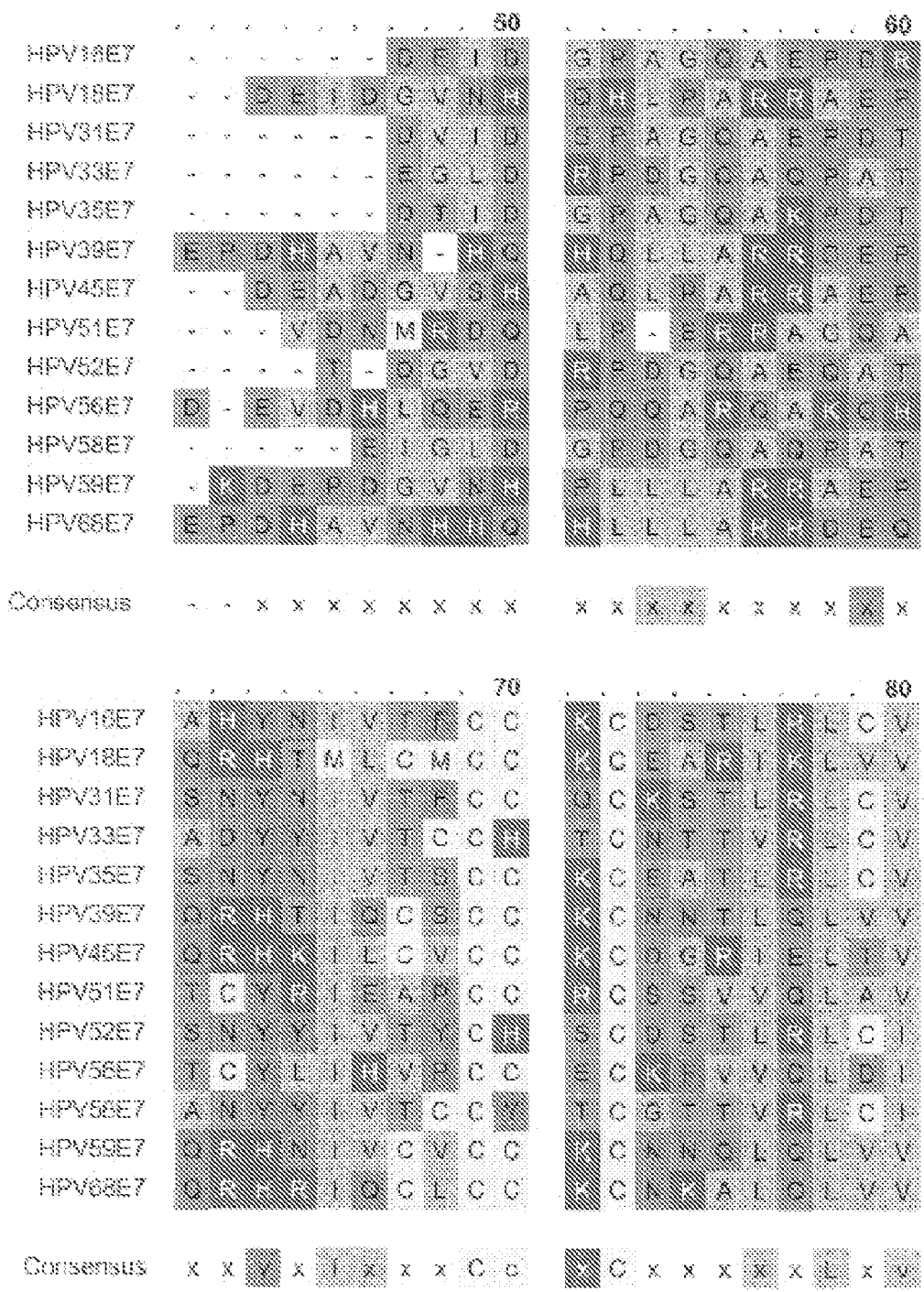

In a further embodiment, the present invention provides immunogenic and pharmaceutical compositions comprising fusions of polypeptides and fusions of polynucleotides of multiple papillomaviruses. For example, the present invention provides immunogenic and pharmaceutical compositions comprising fusions of E6 and E7 proteins from multiple members of the HPV family such as HPV 16, 18, 31, 33, 35, 39, 45, 51, 52, 56, 58, 59 and 68. Examples of HPV E6 polypeptides are shown in FIGS. 2A–E and the amino acid sequences of E6 from HPV 18, 31, 33, 35,39, 45, 51,52, 56, 58, 59 and 68 are set forth in SEQ ID NOS: 15–26, respectively. The nucleotide sequences encoding these HPV E6 polypeptides are set forth in SEQ ID NOS: 42–53, respectively. Examples of HPV E7 polypeptides are shown in FIGS. 3A–C and the amino acid sequences of E7 from HPV 18, 31, 33, 35, 39, 45, 51, 52, 56, 58, 59 and 68 are set forth in SEQ ID NOS: 27–38, respectively. The nucleotide sequences encoding these HPV E7 polypeptides are set forth in SEQ ID NOS: 54–65, respectively. These fusions contain mutations in the residues identified by alignment to correspond to the residues mutated in HPV16 described herein or that correspond to the conserved sequences as shown in the E6 and E7 consensus sequences (SEQ ID NOS: 39 and 40, respectively) that interfere with the protein's oncogenic characteristic without interfering with its ability to induce an immune response. In one embodiment of the present invention the immunogenic and pharmaceutical compositions comprise one fusion comprising E6 and E7 polypeptides from different members of the papillomavirus family. For example, a fusion can comprise in a single construct any possible combination of E6 and E7 from HPV 16, 18, 31, 33, 35, 39, 45, 51, 52, 56, 58, 59 and 68.

The number of E6/E7 polypeptides present in one fusion is limited only by the size limitations of the delivery mechanism or vector in which these compositions are delivered. For example, viruses, constrained by structural limitations, can only package a particular amount of nucleic acid. Those of ordinary skill in the art appreciate the capacity of different viruses to package nucleic acid and appreciate that it is routine to screen for nucleic acids that are of appropriate size for packaging.

Alternatively, the immunogenic and pharmaceutical compositions of the present invention can comprise multiple, different fusions of E6/E7. For example, the immunogenic or pharmaceutical composition can comprise multiple viral particles, each containing different fusions of E6 and E7 sequences from different papillomaviruses.

Immunogenic and pharmaceutical compositions comprising fusions of E6/E7 from multiple papillomaviruses are particularly advantageous because they generate an immune response to multiple E6 and E7 proteins and thus prevent cancers and neoplasias caused by each of these viruses. For example, each of HPV 16, 18, 31, 33, 35, 39, 45, 51, 52, 56, 58, 59 and 68 has been associated with cervical carcinoma and/or intraepithelial neoplasias (Harrison's Principles of Internal Medicine Fifteenth Edition, 2001, 1119; Braunwald et al., Eds., McGraw-Hill). Thus, a fusion of, for example, HPV16 and 18 E6 and E7 polypeptides would provide prevention and treatment of cancers of two different etiologies. Compositions comprising E6 and E7 polypeptides from multiple, different viruses are a particularly powerful means to treat and/or prevent a wide range of papillomavirus-induced cancers, such as cervical cancer, cervical lesions such as CIN, lower gastrointestinal tract cancers, such as anal cancer, and other cancers of the reproductive system, such as penile and vulvar cancer.

The skilled artisan will appreciate methods of determining the safety of immunogenic compositions. Exemplary methods for determining whether, for example, E6/E7 fusions have decreased or abrogated transforming and immortalization capacity include: determining p53 and/or Rb levels by, for example, Western blot, soft agar assays, transfecting primary keratinocytes or mammary epithelial cells and identifying loss of senescence, and transfecting cells and identifying changes in cell morphology. In addition to these functional assays, biochemical assays can be used. For example, the binding of E6 and E7 to cellular proteins such as p53, E6 TP-1, telomerase and Rb can be measured.

Assessing the levels of p53 and Rb is one method for determining the safety of recombinant viral particles, such as VEE, comprising E6/E7 fusions. The steady state levels of p53 and Rb in primary human MECs were assessed following infection with VRP-expressing wildtype HPV16 E6 and E7, as fusion or individual proteins, E7E6 TetM fusion protein, or GFP as a negative control. VRP infection of MECs revealed grossly reduced levels of p53 and Rb in cultures containing wildtype forms of E6 and E7, respectively; simply fusing E7 to E6 was not sufficient to impair the activity of either protein (FIGS. 8A and B). In contrast, MECs infected with E7E6 TetM VRPs containing E6 ($^{63}$C and $^{106}$C) and E7 ($^{24}$C and $^{26}$E) mutations contained normal levels of p53 and Rb (FIGS. 8A and B), indicating these four mutations extinguished the primary oncogenic activity of these proteins.

Because eradication of established tumors requires the induction of a strong T cell mediated immune response against the tumor specific viral antigens E6 and E7, Venezuelan equine encephalitis (VEE) replicons were chosen as the immunogenic composition vector. However, any gene or protein delivery method can be used to deliver and package the immunogenic compositions of the present invention. For example, other viral vectors known to those skilled in the art may be used or the nucleotides encoding the mutant fusion polypeptides may be delivered directly by a plasmid.

Recombinant AV vectors, of which VEE is a member, are particularly versatile because they may be launched as naked RNA, naked plasmid DNA or as particles, with the latter being the most effective formulation for use in immunogenic compositions. One distinguishing property of VRPs in contrast to the other AV replicons is their tropism for dendritic cells (MacDonald, G. H. et al., J Virol 2000, 74:914–922). VRP-targeted dendritic cells may be highly effective vehicles for conveying antigen into lymph nodes and may be an effective dose-sparing strategy.

The immunogenic compositions, particularly the nucleic acids, of the present invention can be delivered via viral vectors, such as lentiviruses, retroviruses, herpes viruses, adenoviruses, adeno-associated viruses, vaccinia virus, baculovirus, alphaviruses and other recombinant viruses with desirable cellular tropism. A wide variety of alphaviruses may be used as viral vectors, including, for example, Sindbis virus vectors, Semliki forest virus (ATCC VR 67; ATCC VR 1247), Ross River virus (ATCC VR 373; ATCC VR 1246) and Venezuelan equine encephalitis virus (ATCC VR 923; ATCC VR 1250; ATCC VR 1249; ATCC VR 532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994. Targeting to specific regions of cells is also provided, for example, targeting so that the fusion polypeptide is localized to the cell membrane, as described in U.S. Pat. No. 6,228,621.

Thus, a gene encoding an E6/E7 polypeptide fusion can be introduced in vivo, ex vivo, or in vitro using a viral vector or through direct introduction of a nucleic acid, such as a DNA or replicon RNA. Expression in targeted tissues can be effected by targeting the recombinant vector to specific cells, such as with a viral vector or a receptor ligand, or by using a tissue-specific promoter, or both. Targeted gene delivery is described in International Patent Publication WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 1992, 7:980–990). Preferably, the viral vectors are replication defective, that is, they are unable to replicate autonomously in the target cell. In general, the genomes of the replication defective viral vectors which are used within the scope of the present invention lack at least one region which is necessary for the replication of the virus in the infected cell. These regions can either be eliminated (in whole or in part), or rendered non-functional by any technique known to a person skilled in the art. These techniques include the total deletion, substitution (by other sequences, in particular by the inserted nucleic acid), partial deletion or addition of one or more bases to an essential (for replication) region (so as to cause a trame shift). Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

Viral vectors include an attenuated or defective DNA or RNA virus, such as, but not limited to, herpes simplex virus (HSV), Epstein Barr virus (EBV), adenovirus, adeno-associated virus (AAV), VEE, and the like. Defective viruses, which entirely or almost entirely lack viral genes, are preferred. Defective viruses do not generate progeny after introduction into the cell. Use of defective viral vectors allows for administration to cells in a specific, localized area, without concern that the viral vector will spread and infect other cells. Thus, a particular tissue can be specifically targeted. Examples of particular vectors include, but are not limited to, the replication defective VEE system as described by Pushko et al. (Virology 1997, 239:389–401), and an attenuated adenovirus vector, such as the vector described by Stratford-Perricaudet et al. (J. Clin. Invest. 1992, 90:626–630; see also La Salle et al., Science 1993, 259: 988–990), and a defective adeno-associated virus vector (Samulski et al., J. Virol. 1987, 61:3096–3101; Samulski et al., J. Virol. 1989, 63:3822–3828; Lebkowski et al., Mol. Cell. Biol. 1988, 8:3988–3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, and AAV vectors), Norgen (adenoviral vectors), Oxford BioMedica (Oxford, United Kingdom; lentiviral vectors), Transgene (Strasbourg, France; adenoviral, vaccinia, retroviral, and lentiviral vectors), AlphaVax (alphaviral vectors such as VEE vectors) and Invitrogen (Carlsbad, Calif.).

In another embodiment, the vector can be introduced in vivo by lipofection, as naked DNA, or with other transfection facilitating agents (peptides, polymers, bupivacaine etc.). Synthetic cationic lipids can be used to prepare liposomes for in vivo transfection of a gene encoding a marker (Felgner et al., Proc. Natl. Acad. Sci. U.S.A. 1987, 84:7413–7417; Felgner and Ringold, Science 1989, 337: 387–388; Mackey et al., Proc. Natl. Acad. Sci. U.S.A. 1988, 85:8027–8031; Ulmer et al., Science 1993, 259:1745–1748). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see, Mackey et al., Proc. Natl. Acad. Sci. U.S.A. 1988, 85:8027–8031). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce the vector in vivo as a naked DNA plasmid. Naked DNA vectors for gene therapy can be introduced into the desired host cells by methods known in the art, e.g., electroporation, nicroinjection, cell fusion, DEAE dextran, calcium phosphate precipitation, use of a gene gun (for example, the Helios gene gun system (Bio-Rad; Hercules, Calif.) can be used for epidermal gene delivery), or use of a DNA vector transporter (see, e.g., Wu et al., J. Biol. Chem. 1992, 267:963–967; Wu and Wu, J. Biol. Chem. 1988, 263:14621–14624; Hartmut et al., Canadian Patent Application No. 2,012,311, filed Mar. 15, 1990; Williams et al., Proc. Natl. Acad. Sci. U.S.A. 1991, 88:2726–2730). Receptor-mediated DNA delivery approaches can also be used (Curiel et al., Hum. Gene Ther. 1992, 3:147–154; Wu and Wu, J. Biol. Chem. 1987, 262: 4429–4432). U.S. Pat. Nos. 5,580,859 and 5,589,466 disclose delivery of exogenous DNA sequences, free of transfection facilitating agents, in a mammal. Alternatively, the DNA is formulated in compositions with transfection facilitating agents, which facilitate immunization, such as bupivicaine and other local anesthetics (U.S. Pat. No. 6,127,170). Recently, a relatively low voltage, high efficiency in vivo DNA transfer technique, termed electrotransfer, has been described (Mir et al., C.P. Acad. Sci. 1998, 321:893; WO 99/01157; WO 99/01158; WO 99/01175).

The term "immunogenic composition", as used herein, broadly refers to any compositions that may be administered to elicit an immunogenic response in the recipient. An immunogenic composition generally comprises an immunologically effective dose of an immunogen (e.g., an antigen of an infectious agent) and a pharmaceutically acceptable carrier and, optionally, an adjuvant. The pharmaceutically acceptable carrier may be sterile water or sterile isotonic saline, as well as any and all solvents, dispersion media, coatings, antibacterial and antifungal agents, isotonic and absorption delaying agents, and the like, compatible with administration to humans. The appropriate carrier will be evident to those skilled in the art and will depend in large part upon the route of administration.

An immunogenic composition may be administered to an organism, e.g., by inhalation or insufflation (either through the mouth or the nose), or by oral, buccal, vaginal, rectal or parenteral administration (e.g., by subcutaneous, intradermal, intramuscular, intraorbital, intracapsular, intraspinal, intrasternal, intraperitoneal or intravenous injection and the like). An immunogenic composition may also be administered by particle-mediated transfer (e.g., using a "particle gun"). See for example, Gainer et al., J. Neurooncol 2000, 47:23–30; Koide et al., Jpn J. Pharmacol 2000, 83:167–174; Kuriyama et al., Gene Ther. 2000, 7:1132–1136; and Yamauchi et al., J. Exp. Zool. 2000, 287:285–293. Such particle transfer methods are particularly preferred for DNA or vector immunogenic compositions, e.g., using a "gene gun." The appropriate route of administration is selected depending on the nature of the immunogenic composition used, and an evaluation of the age, weight, sex and general health of the patient and the antigens present in the immunogenic composition, and similar factors by an attending physician.

An immunogenic composition may comprise, for example, a suspension of an attenuated or killed infectious agent (e.g., a microorganism such as a bacterium or a virus, a parasite or other pathogen, etc.) that causes an infectious disease. Alternatively an immunogenic composition of the invention may be a polypeptide immunogenic compositions or a DNA immunogenic composition. The term "polypeptide immunogenic composition" refers to an immunogenic composition comprising an immunogenic polypeptide, for example a polypeptide derived from an infectious agent which may be an antigen, and therefore activates an immune response in an organism. The term "DNA immunogenic composition" is used herein to refer to immunogenic compositions delivered by means of a recombinant vector. An alternative term used herein is "vector immunogenic composition" (since some potential vectors, for example alphaviruses, are RNA viruses and since in some instances non-viral RNA instead of DNA may be delivered to cells).

The term "immunologically effective dose" refers to that amount of a compound or compositions that is sufficient to result in a desired activity. Thus, as used to describe an immunogenic composition, an immunologically effective dose refers to the amount of a compound or compositions (e.g., an antigen) that is sufficient to produce an effective immune response. In general, selection of the appropriate immunologically effective amount or dosage for the immmunogenic compositions of the present invention will also be based upon the particular immunogenic composition employed, as well as the physical condition of the subject, most especially including the general health and weight of the immunized subject. Such selection and upward or downward adjustment of the effective dose is within the skill of the art. The amount of active component required to induce an immune response without significant adverse side effects varies depending upon the composition employed.

For recombinant, preferably replication-defective, viruses containing the DNA encoding the mutant E6/E7 fusion polypeptides of this invention, the immunologically effective amount is an amount of recombinant virus that is effective in a route of administration to transfect the desired cells of the subject and provide sufficient levels of expression of the selected gene to provide the desired effect. The levels of immunity can be monitored to determine the need, if any, for boosters.

The term "adjuvant" refers to a compound or mixture that enhances the immune response to an antigen. An adjuvant can serve, e.g., as a tissue depot that slowly releases the antigen, and also as a lymphoid system activator that enhances the immune response (see, Hood et al., Immunology, Second Ed., 1984, Benjamin/Cummings: Menlo Park, Calif., p. 384). Such adjuvants also include, among others, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino] ethyl 2-Deoxy4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529). This 529 adjuvant is formulated as an aqueous form or as a stable emulsion.

Other adjuvants include mineral oil and water emulsions, aluminum salts (alum), such as aluminum hydroxide, aluminum phosphate, etc., Amphigen, Avridine, L121/squalene, D-lactide-polylactide/glycoside, muramyl dipeptide, killed Bordetella, saponins, such as Quil A or Stimulon™ QS-21 (Antigenics, Framingham, Mass.), described in U.S. Pat. No. 5,057,540, which is hereby incorporated by reference, and particles generated therefrom such as ISCOMS (immunostimulating complexes). Mycobacterium tuberculosis, bacterial lipopolysaccharides, synthetic polynucleotides such as oligonucleotides containing a CpG motif (U.S. Pat. No. 6,207,646, which is hereby incorporated by reference), cholera toxin (either in a wild-type or mutant form, e.g., wherein the glutamic acid at amino acid position 29 is replaced by another amino acid, preferably a histidine, in accordance with International Patent Publication No. WO 00/18434, incorporated herein by reference), a pertussis toxin (PI), or an E. coli heat-labile toxin (LT), particularly LT-K63, LT-R72, CT-S109, PT-K9/G129; see, e.g., International Patent Publication Nos. WO 93/13302 and WO 92/19265, incorporated herein by reference. Various cytokines and lymphokines are suitable for use as adjuvants. One such adjuvant is granulocyte-macrophage colony stimulating factor (GM-CSF), which has a nucleotide sequence as described in U.S. Pat. No. 5,078,996, which is hereby incorporated by reference. A plasmid containing GM-CSF cDNA has been transformed into E. coli and has been deposited with the American Type Culture Collection (ATCC), 10801 University Boulevard, Manassas, Va. 20110–2209, under Accession Number 39900. The cytokine Interleukin-12 (IL-12) is another adjuvant that is described in U.S. Pat. No. 5,723,127, which is hereby incorporated by reference. Other cytokines or lymphokines have been shown to have immune modulating activity, including, but not limited to, the interleukins 1-alpha, 1-beta, 2, 4, 5, 6, 7, 8, 10, 13, 14, 15, 16, 17 and 18, the interferons-alpha, beta and gamma, granulocyte colony stimulating factor, and the tumor necrosis factors alpha and beta, and are suitable for use as adjuvants.

Other suitable adjuvants include, but are not limited to: surface active substances (e.g., hexadecylamine, octadecylamine, octadecyl amino acid esters, lysolecithin, dimethyldioctadecylammonium bromide), methoxyhexadecylglycerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum phosphate, etc. and immune stimulating complexes. The immunogen may also be incorporated into liposomes, or conjugated to polysaccharides, lipopolysaccharides and/or other polymers for use in an immunogenic composition.

Exemplary adjuvants include, but are not limited to, incomplete Freund's adjuvant, surface active substances (for example, lysolecithin), pluronic polyols, polyanions, peptides, oil or hydrocarbon emulsions. Exemplary adjuvants also include potentially useful human adjuvants such as BCG (bacille Calmette-Guerin) and *Corynebacterium parvum*. In addition, immunostimulatory proteins, such as chemokines, or nucleic acid sequences encoding for chemokines, may be provided as an adjuvant to increase the immune response to an immunogenic composition.

The phrase "pharmaceutically acceptable" refers to molecular entities and compositions that are physiologically tolerable and do not typically produce an allergic or similar untoward reaction (for example, gastric upset, dizziness and the like) when administered to an individual. Preferably, and particularly where an immunogenic composition is used in humnans, the term "pharmaceutically acceptable" may mean approved by a regulatory agency (for example, the U.S. Food and Drug Agency) or listed in a generally recognized pharmacopeia for use in animals (for example, the U.S. Pharmacopeia).

The term "carrier" refers to a diluent, adjuvant, excipient, or vehicle with which a compound is administered. Sterile water or aqueous saline solutions and aqueous dextrose and glycerol solutions are preferably employed as carriers, particularly for injectable solutions. Exemplary suitable pharmaceutical carriers are described in "Remington's Pharmaceutical Sciences" by E. W. Martin.

Toxicity and therapeutic efficacy of compounds can be determined by standard pharmaceutical procedures, for example in cell culture assays or using experimental animals to determine the ILD50 and the ED50. The parameters LD50 and ED50 are well known in the art, and refer to the doses of a compound that are lethal to 50% of a population and therapeutically effective in 50% of a population, respectively. The dose ratio between toxic and therapeutic effects is referred to as the therapeutic index and may be expressed as the ratio: LD50/ED50. Compounds that exhibit large therapeutic indices are preferred. While compounds that exhibit toxic side effects may be used. However, in such instances it is particularly preferable to use delivery systems that specifically target such compounds to the site of affected tissue so as to minimize potential damage to other cells, tissues or organs and to reduce side effects.

Data obtained from cell culture assay or animal studies may be used to formulate a range of dosages for use in humans. The dosage of compounds used in therapeutic methods of the present invention preferably lie within a range of circulating concentrations that includes the ED50 concentration but with little or no toxicity (e.g., below the LD50 concentration). The particular dosage used in any application may vary within this range, depending upon factors such as the particular dosage form employed, the route of administration utilized, the conditions of the individual (e.g., patient), and so forth.

Non-human animals include, without limitation, laboratory animals such as mice, rats, rabbits, hamsters, guinea pigs, etc.; domestic animals such as dogs and cats; farm animals such as sheep, goats, pigs, horses, and cows; and non-human primates.

A therapeutically effective dose may be initially estimated from cell culture assays and formulated in animal models to achieve a circulating concentration range that includes the IC50. The IC50 concentration of a compound is the concentration that achieves a half-maximal inhibition of symptoms (e.g., as determined from the cell culture assays). Appropriate dosages for use in a particular individual, for example in human patients, may then be more accurately determined using such information.

The term "treat" means to attempt to elicit an anti tumor response against cells of the tumor, i.e., the cancer. An anti-tumor response includes, but is not limited to, increased time of survival, inhibition of tumor metastasis, inhibition of tumor growth, tumor regression, and development of a delayed-type hypersensitivity (DTH) response to unmodified tumor cells.

Measures of compounds in plasma may be routinely measured in an individual such as a patient by techniques such as high performance liquid chromatography (HPLC) or gas chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by the routes described above.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for construction with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The terms used in this specification generally have their ordinary meanings in the art, within the context of this invention and in the specific context where each term is used. Certain terms are discussed in the specification, to provide additional guidance to the practitioner in describing the compositions and methods of the invention and how to make and use them.

EXAMPLES

The present invention is described by way of the following examples. However, the use of these or other examples anywhere in the specification is illustrative only and in no way limits the scope and meaning of the invention or any exemplified term. Likewise, the invention is not limited to any preferred embodiment described herein. Indeed, many modifications and variations of the invention may be apparent to those skilled in the art upon reading this specification and can be made without departing from its spirit and scope.

Example 1

Design and Generation of HPV16 Immunogenic Composition Constructs

Materials and Methods

Figure 1B:
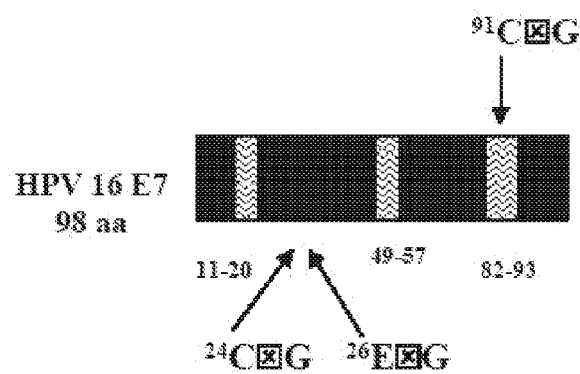
Figure 2B:
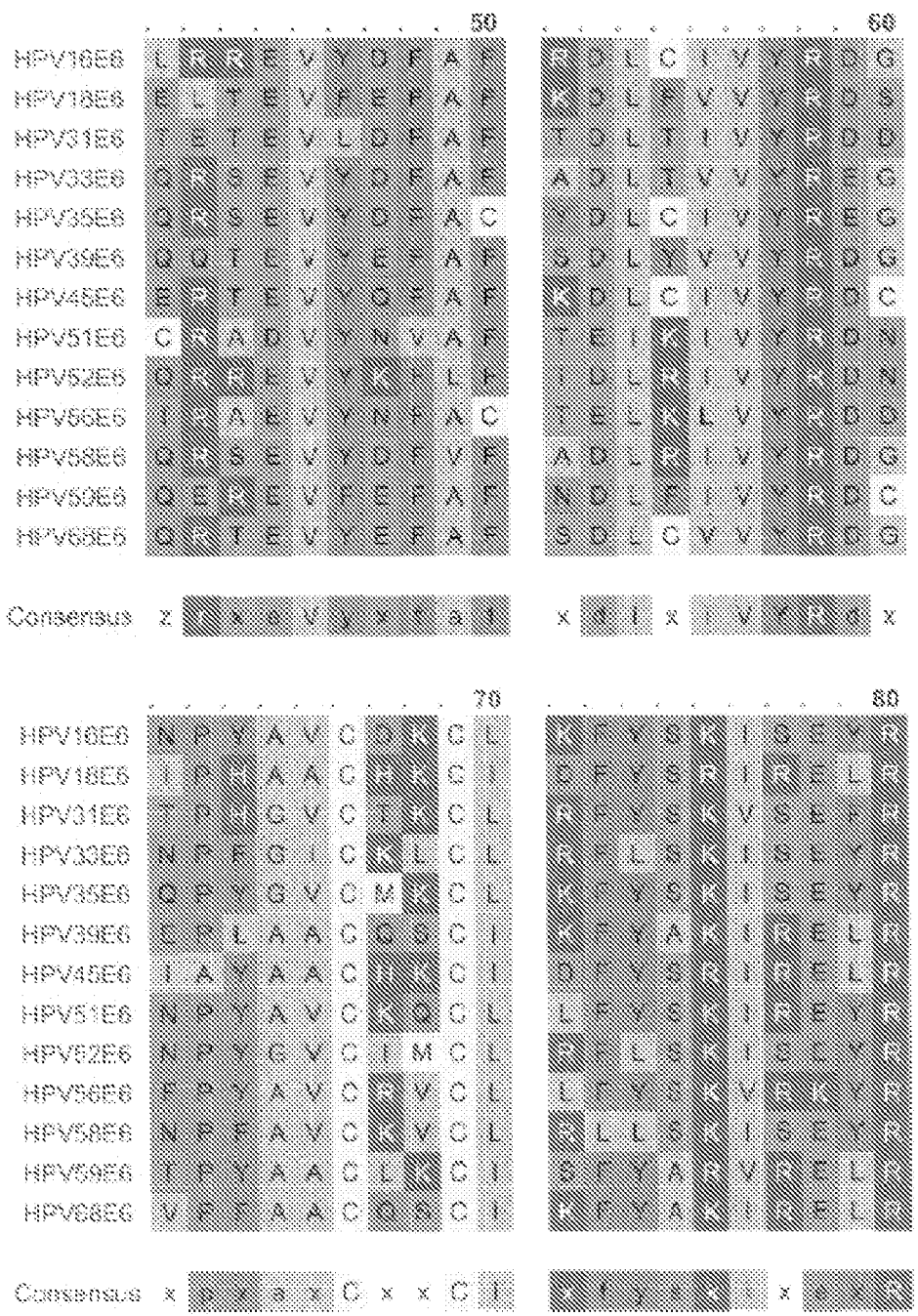
Figure 2C:
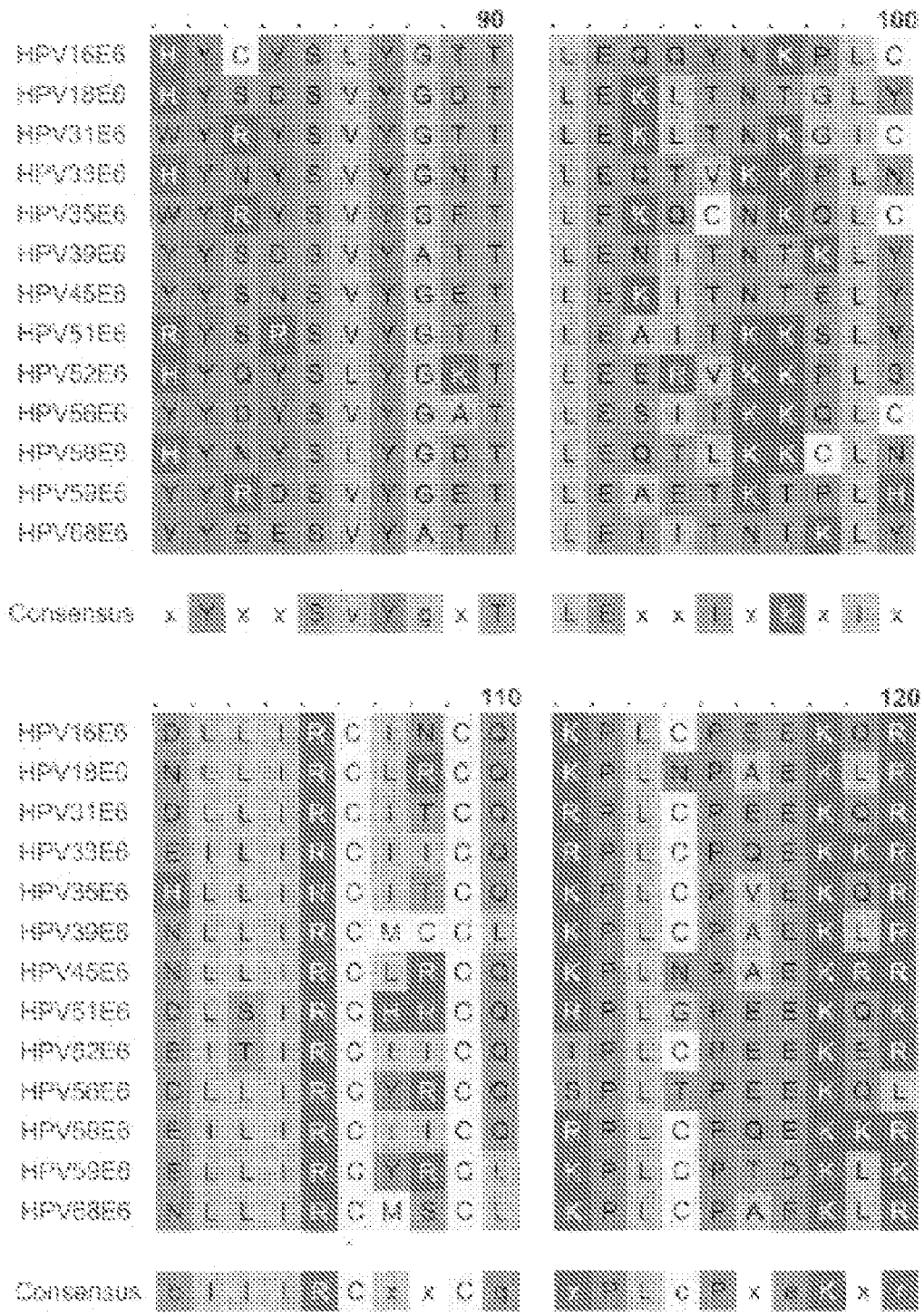
Figure 2D:
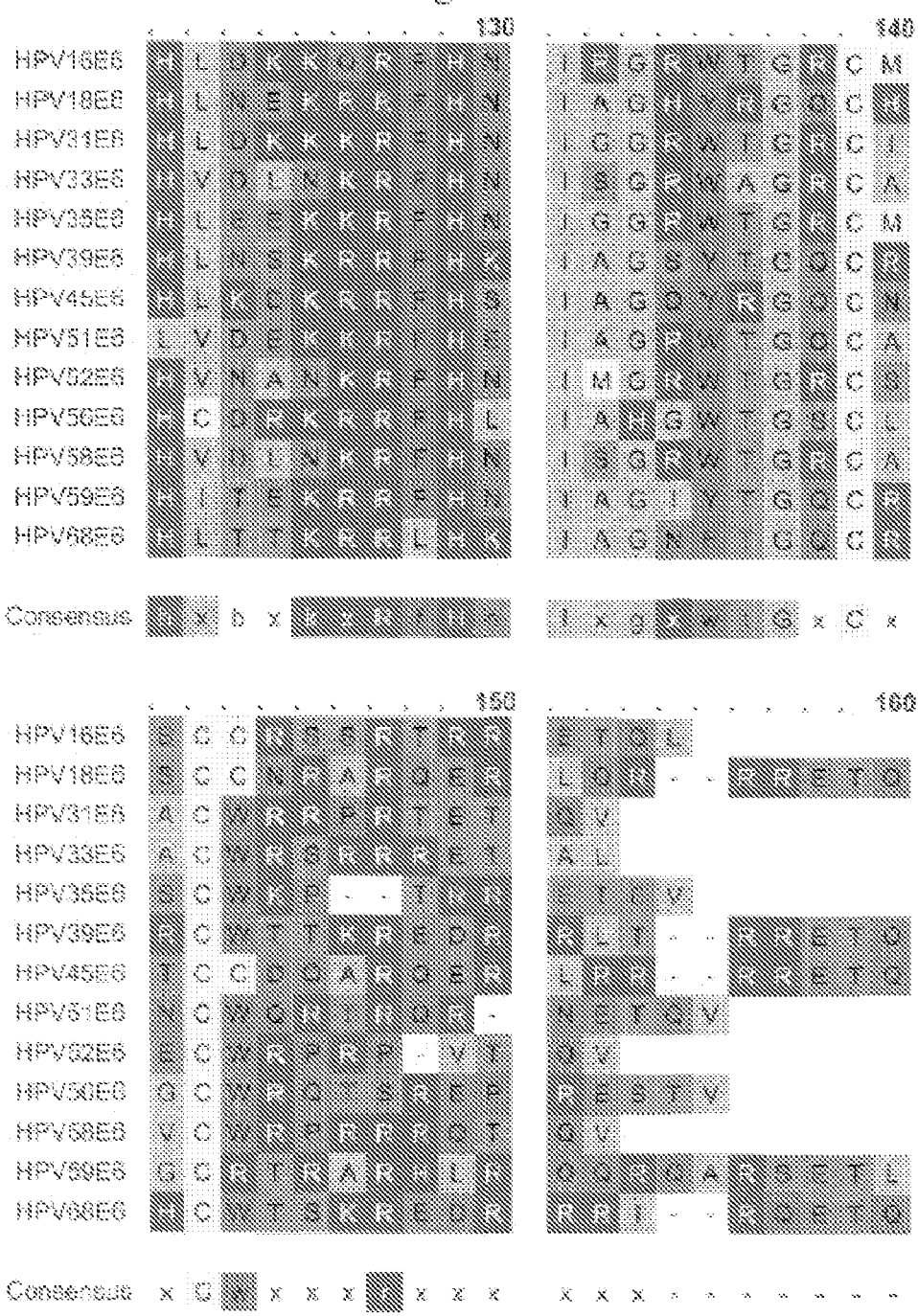
Figure 2E:
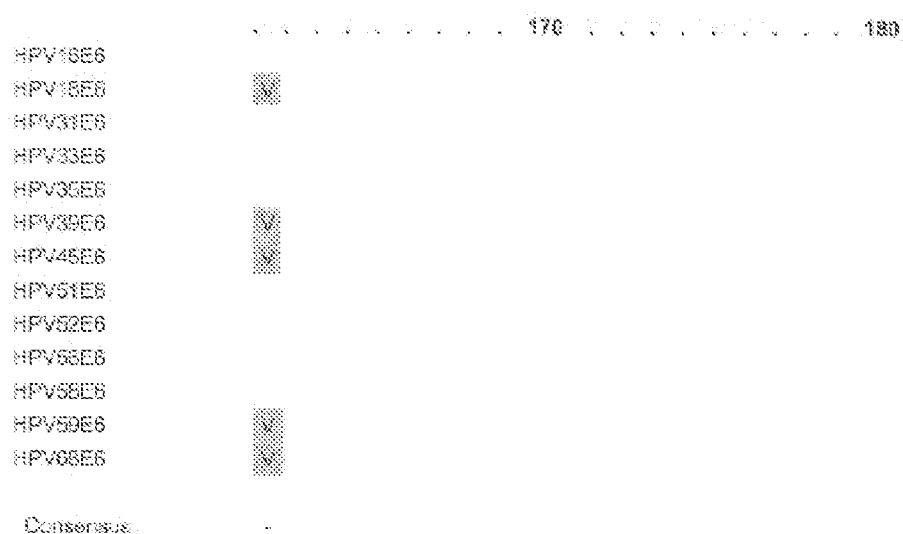

Generation of VEE-replicon constructs. The HPV16 E6 and E7 genes were obtained from pHPV-16 (ATCC, #45113) by PCR methods (Horton et al., Gene 1989, 77:61–8), and fused in two different orientations to generate open reading frames (ORFs) of 744 base pairs (bp) encoding 248 amino acids for all constructs. The methionine start codon of each downstream ORF was removed to eliminate any possibility of internal initiation. Specific nucleotides of the fused ORFs were mutagenized using the QuikChange® Site-Directed Mutagenesis Kit (Stratagene; La Jolla, Calif.). The wild-type (wt) and mutated (mut) fuised genes were sub-cloned into the vector pVR200 (AlphaVax; Durham, N.C.), a plasmid derived from the cDNA of a highly attenuated, non-neurotrophic mutant (V3014) of the Trinidad Donkey strain of Venezuelan equine encephalitis (VEE) (Grieder, F. B. et al., Virology 1995, 206:994–1006). The pVR200 plasmid is described in Pushko et al., (Virology 1997, 239:389–401, in particular see p. 390–391 "Cell lines and plasmids" and p. 393 FIG. 1b). Briefly, this plasmi(has the T7 promoter followed by VEE's non-structural genes, the subgenomic promoter 26S, the cloning site for the gene(s) of interest (in the present invention, the E6/E7 fuisions), and a NoII linearization site.

Replication-incompetent VEE replicon particles (VRPs) were prepared by the split helper method and titrated as described (Pushko et al., Virology 1997, 239:389–401). Briefly, the pVR200 plasmid (with the fusions of interest cloned in) was cotransfected into cells along with: (1) a capsid-encoding helper construct, and (2) a glycoprotein-encoding helper construct. Neither of these helper constructs had packaging sequences and therefore were not incorporated into VRPs. Thus, the resulting VRPs were replication defective. The potency of each VRP preparation, expressed as infectious units/milliliter (IU/ml), was defined by the nunber of E7-positive particles as determined by titration on baby hamster kidney (BHK)-21 cells. Titers of all VRP preparations exceeded $10^9$ IU per electroporation; an effective dose of $3 \times 10^5$ IU per immunization was used throughout these studies and as previously described (Velders M. P. et al., Cancer Res 2001, 61:7861–7867).

Western blots and Immunofluorescence. BHK-21 cells were infected with the indicated VRPS. Twenty-four hours post-infection the cells were either harvested in SDS sample buffer for Western blot analysis or fixed with methanol-acetone for immunofluorescence. To detect protein expression by Western blot, the proteins in the cell lysate were separated by SDS-PAGE, tansfenred onto a Polyvinyldene (PVD) membrane and analyzed with the Western Breeze detection system (Invitrogen; Carlsbad, Calif.) using an anti-HPV16 E7 monoclonal antibody (Zymed; San Francisco, Calif.). For immunofluorescence analysis, the fixed cells were incubated with a primary anti-E7 antibody followed by FITC-labeled goat anti-mouse secondary antibody (# 554001, Pharmingen; San Diego, Calif.). The cell nuclei were stained using Viaprobe (#555815, Pharmingen).

Results

In order to design effective and safe immunogenic compositions against HPV16-induced cervical cancer, antigenic diversity was increased by expressing both E6 and E7 tumor specific antigens. The inclusion of full-length E6 and E7 genes in a VRP immunogenic composition is desirable for maximizing the likelihood of expressing all possible epitopes for stimulating $CD8^+$ and $CD4^+$ T cells in HLA Class I and Class II-diverse human populations. Fusions of the E6 and E7 ORFs were accomplished in two different orientations by PCR and up to five amino acids were mutagenized (FIGS. 1A and B) to obtain expression constructs for producing particular E6/E7 fusion polypeptides.

A single amino acid substitution at position $^{63}C$ has been shown to destroy several HPV16 E6 functions: p53 degradation, E6TP-1 degradation, activation of telomerase, and, consequently, immortalization of primary epithelial cells (Gao, Q. et al., J Virol 2001, 75:4459–4466). HPV16 E6 containing a single point mutation at $^{106}C$ neither binds nor facilitates degradation of p53 and is incapable of immortalizing human MECs, a phenotype dependent upon p53 degradation (Dalal et al., J Virol 1996, 70:683–688). The 98 amino acid HPV16 E7 protein binds Rb through an LX-C-X-E motif; mutations at positions $^{24}C$ and $^{26}E$ of this motif destroy Rb binding and degradation (Munger, K, et al., Oncogene 2001, 20:7888–7898). In addition to these two point mutations in E7, a third amino acid, $^{91}C$, was mutated to destroy the single zinc finger in E7.

A first fusion protein, referred to here as E6E7wt comprises the amino acid sequence of a wild-type E6 polypeptide sequence (SEQ ID NO: 13) at the amino terminus and the amino acid sequence of a wild-type E7 polypeptide sequence (SEQ ID NO: 14) at the carboxy terminus. A representative amino acid sequence for such a fusion polypeptide is provided at SEQ ID NO: 1. An exemplary nucleotide sequence encoding such a wild-type E6E7 fusion polypeptide is set forth in SEQ ID NO: 2.

A second fusion polypeptide, referred to as E6E7TetM, was also prepared. Like the E6E7wt fusion polypeptide, E6E7TetM comprises an E6 polypeptide sequence at the amino terminus and an E7 polypeptide sequence at the carboxy terminus. However, the E6 polypeptide sequence of this construct contains glycine amino acids at residues 63 and 106 of the E6 polypeptide rather than the cysteine amino acids found in the wild-type E6 amino acid sequence (SEQ ID NO: 13). In addition, the E7 polypeptide sequence of this construct contains glycine amino acids at residues 24 and 26 of the E7 polypeptide rather than the cysteine (24) and glutamate (26) amino acids found in the wild-type E7 amino acid sequence (SEQ ID NO: 14). A representative amino acid sequence for such a fusion polypeptide is provided at SEQ ID NO: 3. An exemplary nucleotide sequence encoding such an E6E7TetM fusion polypeptide is set forth in SEQ ID NO: 4.

A third fusion polypeptide, referred to as E6E7PentM, was also prepared. Like the E6B 7TetM fusion polypeptide, E6E7PentM comprises an E6 polypeptide sequence, which comprises glycine amino acids at residues 63 and 106, at its amino terminus and an E7 polypeptide sequence, which comprises glycine amino acids at residues 24 and 26, at its carboxy terminus. However, the E7 polypeptide sequence of this fusion protein also contains a glycine amino acid at residue 91 of the E7 polypeptide sequence, rather than the cysteine amino acid found in the wild-type E7 amino acid sequence (SEQ ID NO: 14). A representative amino acid sequence for such a fusion polypeptide is provided at SEQ ID NO: 5. An exemplary nucleotide sequence encoding such an E6E7PentM fusion polypeptide is set forth in SEQ ID NO: 6.

A fourth fusion polypeptide, referred to as E7E6wt, comprises the amino acid sequence of a wild-type E7 polypeptide (SEQ ID NO: 14) sequence at the amino terminus and the amino acid sequence of a wild-type E6 polypeptide (SEQ ID NO: 13) sequence at the carboxy terminus. A representative amino acid sequence for such a fusion polypeptide is provided at SEQ ID NO: 7. An exemplary nucleotide sequence encoding such an E7E6wt fusion polypeptide is set forth in SEQ ID NO: 8.

A fifth fusion polypeptide, referred to as E7E6TetM, was also prepared. Like the E7E6wt fusion polypeptide, E7E6TetM comprises an E7 polypeptide sequence at the amino terminus and an E6 polypeptide sequence at the carboxy terminus. However, the E7 polypeptide of this construct contains a glycine residue at amino acids 24 and 26 of the E7 polypeptide, rather than the cysteine (24) and glutamate (26) amino acids found in the wild-type E7 amino acid sequence (SEQ ID NO: 14). In addition, the E6 polypeptide of this construct contains a glycine residue at amino acids 63 and 106 of the E6 polypeptide, rather than the cysteine amino acid found in the wild-type E6 amino acid sequence (SEQ ID NO: 13). A representative amino acid sequence for such a fusion polypeptide is provided at SEQ ID NO: 9. An exemplary nucleotide sequence encoding such an E7E6TetM fusion polypeptide is set forth in SEQ ID NO: 10.

A sixth fusion polypeptide, referred to as E7E6PentM, was also prepared. Like E7E6TetM, E7E6PentM comprises an E7 polypeptide, which comprises glycine amino acids at residues 24 and 26 of the E7 polypeptide, at its amino terminus and an E6 polypeptide, which comprises glycine amino acids at residues 63 and 106 of the E6 polypeptide, at is carboxy terminus. However, the E7 polypeptide sequence of this construct also contains a glycine amino acid at residue 91 of the E7 polypeptide, rather than the cysteine amino acid found in the wild-type E7 amino acid sequence (SEQ ID NO: 14). A representative amino acid sequence for such a fusion polypeptide is provided at SEQ ID NO: 11. An exemplary nucleotide sequence encoding such an E7E6TetM fusion polypeptide is set forth in SEQ ID NO: 12.

The mutations in E6 and E7 were designed to 1) disrupt three zinc fingers, therefore destabilizing the protein and accelerating degradation (and thus increase immunogenicity) ($^{63}$C and $^{106}$C of E6; $^{91}$C of E7 (Dalal et al., J Virol 1996, 70:683–8; Shi et al., J Virol 1999, 73:7877–81)); 2) perturb E6-induced degradation of p53 ($^{106}$C; (Dalal et al., J Virol 1996, 70:683–8)) and E6-TP1-binding (Gao et al., J Virol 2001, 75:4459–66); and 3) disrupt Rb binding and degradation by E7 ($^{24}$C and $^{26}$E; (Edmonds and Vousden, J Virol 1989, 63:2650–6)). These mutations were carefully chosen to lie outside known HLA epitopes, with the exception of $^{91}$C. Although $^{91}$C is known to be part of an HLA A2 epitope that spans amino acids 86–93 of E7 (Ressing et al., J Immunol 1995, 154:5934–43; Ressing et al., Cancer Res 1996, 56:582–8; Evans et al., Cancer Res 1997, 57:2943–50), it was decided mutate this amino acid to achieve maximum immunogenic composition safety, since this mutation disrupts a zinc finger of E7 known to be required for its immortalizing activity (Jewers et al., J. Virol 1992, 66:1329–1335). Since this mutation it is not located in the P2 amino acid anchor region of peptides with known HLA-A*0201 binding properties (Rammensee et al., Annu Rev Immunol 1993, 11:213–44), it is possible that C91G mutated polypeptides may retain their ability to bind the HLA-A*0201 molecule. Also, it is possible that the C91 mutation might affect the cleavage of another HLA epitope spanning amino acids 82–90 of E7. The fusion constructs containing those five amino acid mutations were named PentM.

Although mutations at each of these sites of HPV16 E6 and E7 had been previously disclosed individually, it was not known what combinations of these mutations, if any, would maintain their immunogenicity.

In order to develop a therapeutic cervical cancer immunogenic composition that elicits a robust cell-mediated response against the viral oncogene products E6 and E7, these fusions were cloned into the Venezuelan equine encephalitis (VEE) virus replicon-based system. The advantages of recombinant VEE immunogenic compositions include high levels otheterologous gene expression, dendritic-cell tropism (thereby targeting expression to lymphoid tissues, an important site for inducing immunity), induction of apoptosis and robust cellular and humoral immune responses and efficient repeated immunization, since there is no widespread existing immunity to VEE in humans. In addition, alphaviruses such as VEE replicate the RNA of interest in the cell cytosol and are cytopathic, thereby significantly reducing the risk of integration of E6 and E7 into the cellular genome.

To assess the expression of these fused constructs, BHK cells were infected with the recombinant VRPs and subsequently analyzed by Western blotting and immunofluorescence. Western blot analysis revealed that the E6E7 fusion proteins migrated generally at a molecular weight of about 30 kDa on SDS-PAGE. Although the expression level of the wildtype and mutated constructs was comparable, their intracellular localization was dramatically different. Inmunofluorescence staining of these fusion proteins revealed a punctate staining pattern overlapping the nuclei for both wildtype E6 and E7 VRPs, while a more diffuse, perinuclear staining was observed for all TetM and PentM VRPs (data not shown). Such a diffuse, perinuclear localization is suggestive of protein aggregation/misfolding. Such misfolding is suggestive of protein instability, further supporting that these fusions have an increased capacity to elicit CTL responses.

Example 2

Cellular Immune Responses Induced by Different Immunogenic Composition Constructs Materials and Methods Mice and cell lines. Specific pathogen-free 6–12 week old female C57BL/6 mice were obtained from Taconic Farms (Germantown, N.Y.). Mice were housed in the Wyeth and Loyola University (Chicago) animal facilities under filtertop conditions, with water and food ad libitum. Specific pathogen-free 6–week old female HLA-A*0201 mice were purchased from Jackson Laboratories (Bar Harbor, Me.). MC57G and ELA cells were used for cytotoxicity assays. BHK-21 cells were used for VEE RNA expresson, VEE replicon particle (VRP) packaging and titration (potency assays). Tumor challenge studies were performed using the E6E7-positive tumor lines C3 (Feltkamp, M. C. W. et al., Eur J Immun 1993, 23:2242–2249), TC-1 (Lin, K. Y., et al., Cancer Res 1996, 56:21–26), and HLF16. All cell lines (except HLF16, C3 and TC-1 cells) were obtained from American Type Culture Collection (ATCC; Manassas, Va.).

Cytotoxicity (CTL) assay. C57BL/6 mice were immunized subcutaneously with 3×10$^5$ infectious units of VRPs. Cytotoxicity assays were performed 4 weeks after immunizing mice with a single dose of $3\times10^5$ of the indicated VRP administered in the rear footpads. Single-cell splenocyte suspensions were restimulated (20:1) with mitomycin-C-treated MC57G cells infected with recombinant modified Vaccinia Virus Ankara (MVA) vectors encoding E7 or E6 (E7-MVA or E6-MVA) at a multiplicity of infection (MO1) of 5. CTL activity was measured 5 days later. E7- or E6-MVA-infected MC57G cells and HPV16 E7$_{49-57}$ H-2D$^b$-restricted peptide RAHYNIVTF (SEQ ID NO: 41, which corresponds to amino acids 49–57 of SEQ ID NO: 14); Lin et al., Cancer Res 1996, 56, 21–6)pulsed EL-4 cells (ATCC) served as targets. MC57G cells were infected for 1 h with either E7-MVA or E6-MVA at a MOI of 5. EL-4 cells ($1\times10^7$) were incubated with peptide (20 µg/ml) for 1 h. Target cells were then labeled 3 h later with Europium (Eu$^{+3}$; Sigma Chemical Co., St. Louis, Mo.) by electroporation. Effector and target cells were incubated at the indicated ratios for 3 h, after which supernatants were harvested and mixed with Enhancer solution (Wallac; Turku, Finland). Eu$^{+3}$ release was quantitated by time-resolved fluorescence using a 1234 Delfia fluorometer (Wallac). The percentage of specific lysis was calculated as (Experimental-spontaneous release/Maximal-spontaneous release)×100. The percentage spontaneous releases ranged from 5 to 10%.

Results

Figure 4A:
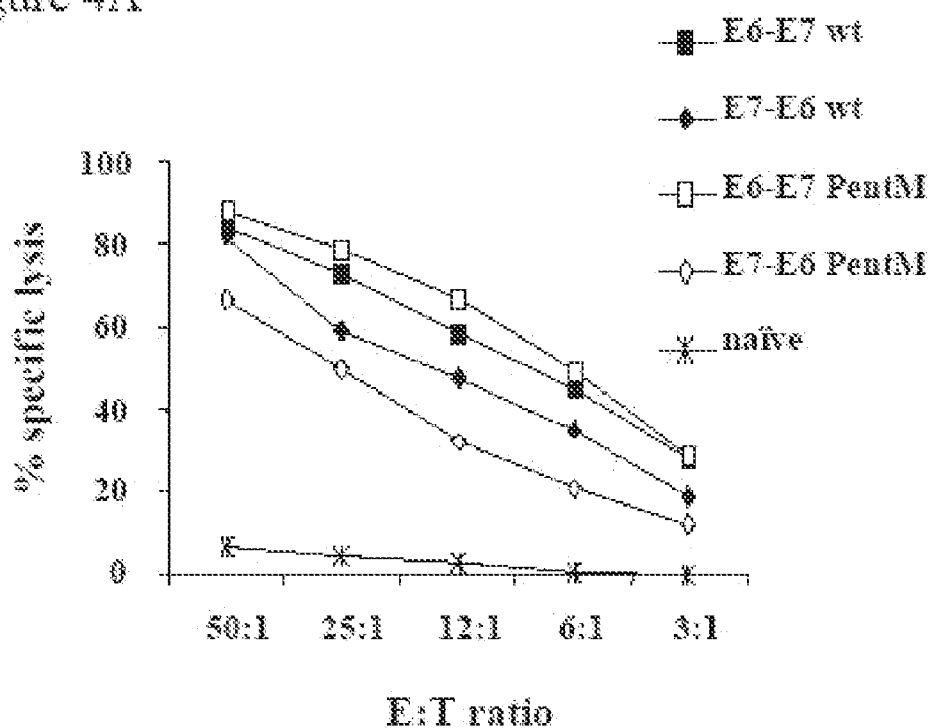
FIGS. 4A and 4B are graphs showing percentage specific lysis versus effector to target cell (E:T) ratio, which represents CTL responses following VRP immunization. C57BL/6 mice were immunized subcutaneously with 3×10$^5$ IU of the indicated VRP, and CTL assays were performed 1 month later. Cytotoxicity was measured by Europium release of E7-MVA (A) or E6-MVA (B) infected MC57G target cells. These results were reproduced in two additional experiments (data not shown).
Figure 4B:
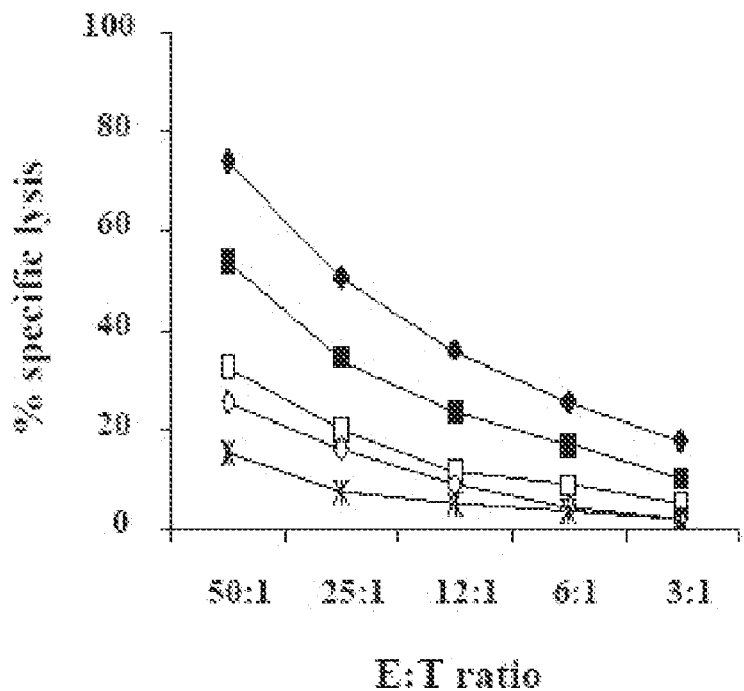

To characterize immune responses induced by the different immunogenic composition constructs, C57BL/6 mice were immunized subcutaneously in the rear footpads with $3\times10^5$ infectious units of the wt and PentM VRP constructs. One month after immunization, CTL-mediated lysis was measured by Europium release assay using MC57G targets infected with MVA encoding E6 or E7. FIG. 4A reveals that CTL from mice immunized with either wildtype or PentM VRPs killed E7 expressing targets. Identical results were found with EB7$_{49-57}$ peptide pulsed ELA targets (data not shown). CTL mediated lysis was also evident against E6 targets from mice immunized with all forms of VRPs, although lysis was substantially reduced in recipients of mutant VRPs (FIG. 4B). These results for E7 and E6 specific lysis were reproduced in two additional experiments and were also observed using TetM VRPs immunized mice (data not shown).

These results show that immunization with VRPs encoding mutant and wildtype fusion proteins generated similar CTL responses to the immunodominant E7$_{49-57}$ epitope which is important in tumor rejection. While CTL responses were clearly detectable against E6 targets from animals immunized with VRPs expressing wildtype genes, diminished CTL responses were observed in mice receiving a mutant form of E6, suggesting that $^{63}$C and/or $^{106}$C is an important component of an H-2$^b$-restricted epitope.

Example 3

Tumor Protection and Therapeutic Efficacy of Immunogenic Composition Constructs in C3 and TC1 Tumor Models Materials and Methods Tumor protection and therapeutic experiments. Groups of 14 C57BL/6 mice were anesthetized by intraperitoneal injection of 10 mg/kg xylazine (Sigma, St. Louis, Mo.) and 100 mg/kg ketamine (Abbott Laboratories, Chicago, Ill.) and immunized by injection of $3\times10^5$ VRPs into the hind footpads on days –21 and –7. Negative control mice received $3\times10^5$ IU of green fluorescent protein (GFP) VRP. One week later, half of the mice in each group were challenged by subcutaneous flank injections with $5\times10^5$ C3 cells (Feltkamp et al., Eur J Immunol 1995, 25:2638–42) and half were challenged with $5\times10^4$ TC-1 cells (Lin et al., Cancer Res 1996, 56:21–6). Tumor growth was monitored every three days. For C3 therapeutic experiments, mice were first challenged with $5\times10^5$ C3 tumor cells in the flank followed 7, 14, and 21 days later with the indicated VRP at $3\times10^5$ dose per immunization. For the human lung fibroblast (HLF) therapeutic experiment, HLA-A*0201 transgenic mice were challenged with $2\times10^6$ HLF16 cells by subcutaneous injection into the left flank on day 0. At 5, 10 and 15 days following challenge, mice were anesthetized as described above and immunized by injection of $3\times10^5$ VRPs into the hind footpads. Tumor growth was monitored every 5 days.

See also: Mice and Cell lines (above).

Results

Figure 5A:
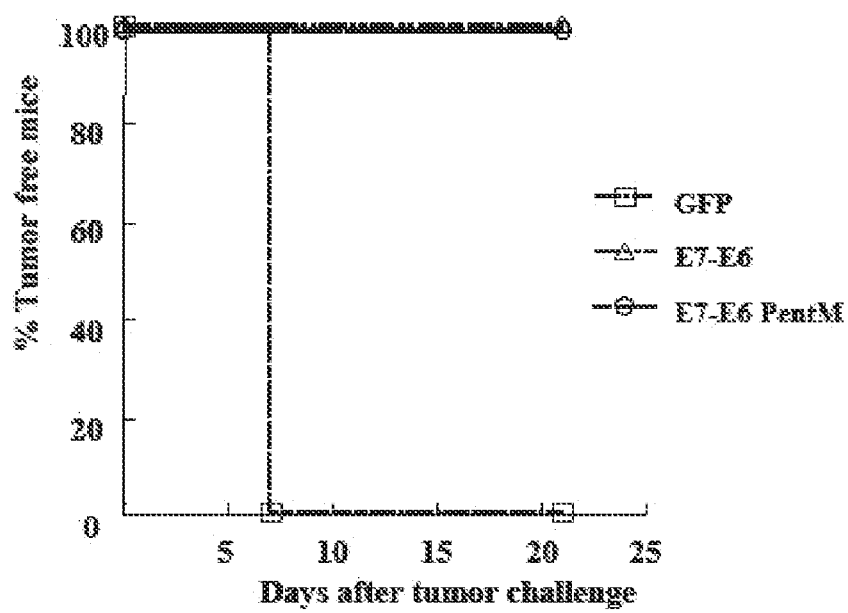
FIGS. 5A and 5B are graphs demonstrating percentage tumor free mice versus number of days after tumor challenge. C57BL/6 mice (n=8/gp) were primed and boosted with 3×10$^5$ IU of the indicated VRP immunogenic composition on days −21 and −7 and challenged on day 0 with either 5×10$^5$ C3 (A) or 5×10$^4$ TC-1 (B) tumor cells in the flank. Tumors were monitored every 3 days.
Figure 5B:
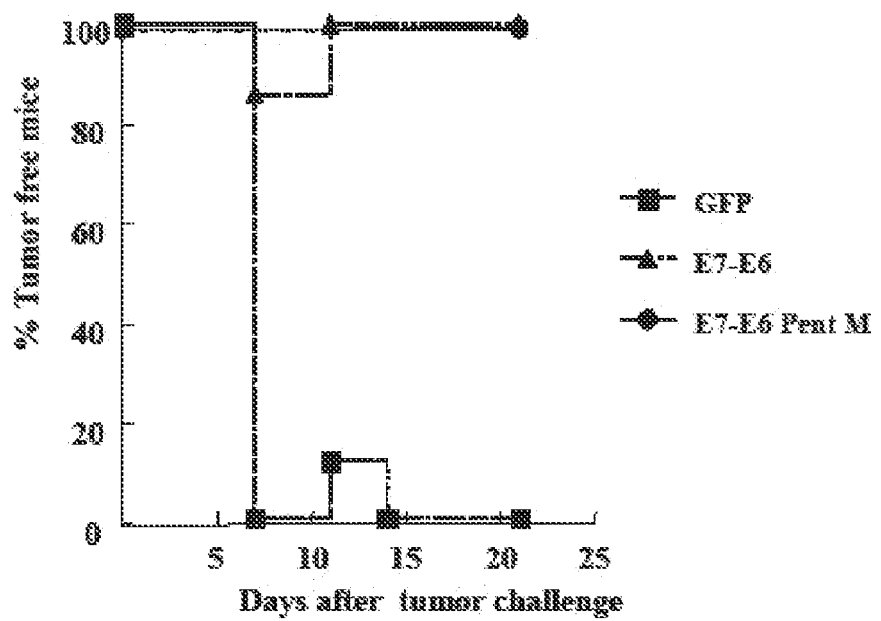

VRPs encoding wildtype E7E6 and E7E6PentM fusion proteins were compared for prophylactic antitumor efficacy in vivo. Mice in all groups were immunized at days 0 and 21 with $3\times10^5$ of the indicated VRP and subsequently challenged with C3 or TC-1 tumor cells. All mice receiving GFP-VRP as a negative control developed tumors within about 7 days post-tumor challenge (FIGS. 5A and B). In contrast, all mice receiving either E7E6 wildtype or PentM were protected from tumor challenge regardless of whether they received C3 ($5\times10^5$) FIG. 5A) or TC-1 ($5\times10^4$) (FIG. 5B) tumor cells. These data suggest that protection was not limited to a specific murine tumor challenge model and that protection was critically dependent upon VRP-encoded E6 and E7 gene products.

Figure 6:
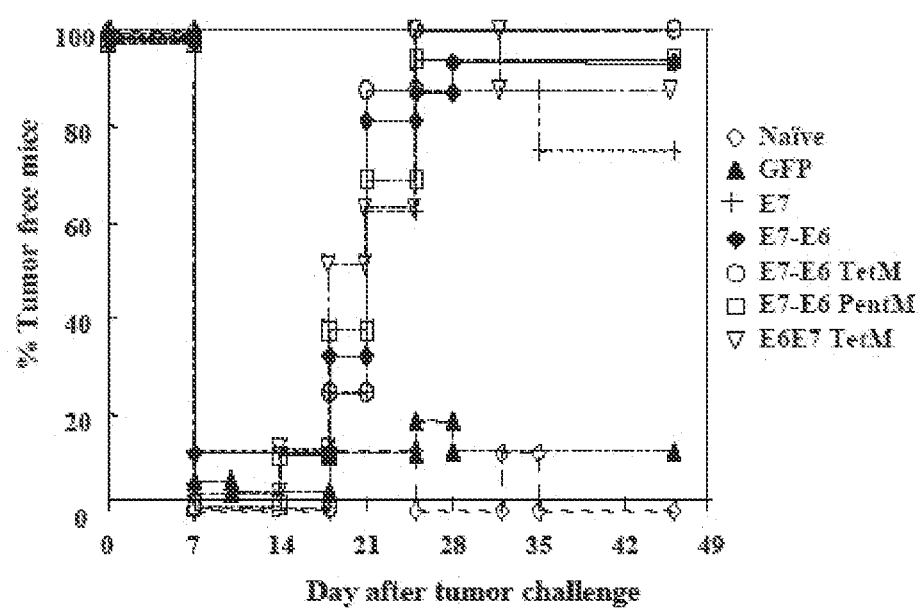
FIG. 6 is a graph demonstrating percentage tumor free mice versus number of days after tumor challenge. C57BL/6 mice (n=8–16/gp) received 5×10$^5$ C3 tumor cells on day 0 and were immunized with the indicated VRP at days 7, 14, and 21. Tumors were monitored every 3 days over 45 days.

As a more stringent measure of antitumor efficacy, in the next experiment mice were challenged with C3 tumor cells prior to immunization with E7E6 wildtype, PentM, or TetM VRPs at days 7, 14, and 21. FIG. 6 shows that 85%–100% of mice receiving any of the mutant or wildtype E6 and E7 fusion-protein-expressing VRPs rejected C3 tumors in contrast to 0%–12% of negative control mice. As shown previously by Velders et al. (Cancer Res 2001, 61:7861–7) and in FIG. 6, a VRP immunogenic composition expressing E7 alone promoted rejection in only 65%–75% of mice.

In conclusion, the inclusion of the gene encoding E6 as a fusion partner with E7 reproducibly enhanced therapeutic antitumor efficacy (85%–100%, FIG. 6) compared to E7 alone (67%–75%, FIG. 6) regardless of whether E6 was wild-type or mutated. Therefore, the mutations in E6, when expressed as a fusion with E7, did not result in a diminished antitumor effect in these tumor models. However, the results illustrate that optimal CTL responses to epitopes containing mutant amino acids may not be elicited in some individuals immunized with mutant VRP. In humans this may not be a cause for concern given the diversity of HLA Class I and Class II alleles compared to the limited number of H-2 alleles expressed by C57BL/6 mice.

Example 4

Therapeutic Efficacy of Immunogenic Composition Constructs in the HLF16 Tumor Model Although the results of Examples 2 and 3 show encouraging results, H-2b restricted T cell recognition of HPV antigens in C57BL/6 mice provides limited predictive value for HLA restricted anti-tumor responses. Therefore, the demonstration that the same immunogenic compositions can induce HLA-A*0201 restricted responses against HPV16 E6 and E7 in HLA-A*0201 transgenic mice is particularly important (Ressing et al., J Immunol 1995, 154:5934–5943).

CD8$^+$ T cells from HLA-A*0201 transgenic mice have been shown to recognize the same HLA-A*0201 restricted antigens as those recognized by HLA-A*0201 restricted human CTLs (Engelhard et al., J Immunol 1991, 146: 1226–1232; Shirai et al., J Immunol 1995, 154:2733–2742). The use of HLA transgenic mice could therefore overcome the limitations of H-2 restricted tumor rejection. However, no HPV tumor model has been available to test HLA-A*0201 restricted anti-tumor response. Here, the first HPV16 tumor model for HLA-A*0201 transgenic mice is presented (also described in Eiben G L et al., Cancer Research, Oct. 15, 2002, 62, No. 20). The immunogenicity of the E6/E7 fusions was tested in this model.

This tumor model was developed by transfecting fibroblasts from HLA-A 0201 transgenic C57BL/6 mice with HPV16 E6 and E7 and Ras V12, generating a cell line (HLF16) that is tumorigenic in HLA-A 0201 mice. The dominant H-2Db epitope was removed from the E7 gene to ensure that the anti-tumor responses would be independent of the 49–57 epitope and would be likely mediated through the HLA-A*0201.

The TetM set of constructs were used in the HLF tumor model. These constructs contained only four mutations: C63G and C106G in E6; C24G and E26G in E7. The mutation C91G in E7 (present in the PentM constructs) was eliminated because it is known to be part of HLA-A*0201 epitope that spans amino acids 86–93 of E7 (Ressing et al., 3 limunol 1995, 154:5934–43; Ressing et al., Cancer Res 1996, 56:582–8; Evans et al., Cancer Res 1997, 57:2943–50). By using a class II-binding algorithm (www.imtech.res.in/raghava/propred), it was also determined that there is a predicted epitope promiscuous for several class II haplotypes between amino acids 87 and 95 of E7. Since class II-mediated immune responses were found to be necessary for the therapeutic efficacy of the VRP immunogenic composition in the C3 tumor model, the hypothesis was that C91G mutation present in the PentM immunogenic composition constructs could disrupt human class II epitopes.

Materials and Methods

Construction and characterization of the HLF16 tumor model. The HLF16 tumor cell line was derived from heart lung tissue dissected from HLA-A2 Dd transgenic C57BL/6 mice. After several weeks in culture, adherent fibroblasts were transformed with a pIRES bi-cistronic vector containing E6/E7 and activated H-ras while conferring geneticin resistance. The only known H-2b Class I restricted epitope from the HPV16 E749–57 gene product (Velders et al., Cancer Res 1997, 61:7861–7867) was removed to ensure that the tumor would not present this immunodominant HPV16 E7 epitope. Transfectants were selected on G418 and clonally expanded. Individual clones were then tested for HLA-A*0201 expression by FACS analysis. Clones that showed the highest HLA-A*0201 expression were subsequently tested for their ability to form colonies in soft agar. Heart lung fibroblast clone 16 (HLF16) showed anchorage independent growth in soft agar and was chosen for further studies. E7 expression was evident in the cytoplasm and nucleus of HLF16 after immunofluorescence staining with an anti-E7 monoclonal antibody. To determine if the HLF16 line would in fact form tumors in mice, HLA-A*0201 transgenic mice were injected with different concentrations of tumor cells and monitored for 35 days. All mice developed tumors but only those challenged with the highest dose, $2\times10^6$ HLF16 cells, maintained a tumor over the timne course. The HLF16 tumor arose at approximately day 5 and continued to grow progressively until it became approximately 12×12×12 mm by day 35 at which point the mice were sacrificed. Construction and characteristics of the HLF16 tumor cell line is also described in Eiben G L et al. (Cancer Research, Oct. 15, 2002, 62, No. 20).

Soft Agar Assay. Anchorage-independent growth capability was determined by assessing the colony formation efficiency of cells suspended in soft agar. Transformed and control cells ($0.5\times10^6$, $0.25\times10^6$ and $0.1\times10^6$) were seeded in 5 ml of 0.3% overlay agar and added to 10 mm plates coated with 20 ml of 0.6% underlay agar. Plates were allowed to dry and were incubated at 37° C. Colonies were counted 3 weeks after plating.

See also: mice and cell lines, tumor protection and therapeutic experiments, and western blots and immunofluorescence (above).

Results

The TetM constructs were checked for expression by Western blot and immunofluorescence of BHK-infected cells. Both E6E7 and E7E6 TetM proteins migrated at about 30 kDa on SDS-PAGE and had a diffuse peri-nuclear localization very similarly to the PentM constructs.

Both PentM and TetM immunogenic composition constructs were analyzed for their tumor therapeutic efficacy in the HLF tumor model (FIG. 7). The transgenic mice were challenged with $2\times10^6$ HLF16 cells subcutaneously and at days 5, 10 and 15 after challenge, the mice were immunized with either GFP VRPs, TetM VRPs or PentM VRPs. Complete tumor rejection followed immunization with E7E6 TetM VRPs, while E7E6 PentM VRPs and E6E7 PentM VRPs induced tumor regression of 90% of the mice, except E6E7 TetM (FIG. 7). These results demonstrate that therapeutic immunization with several of the VRPs tested here resulted in a high degree of antitumor efficacy independent of contributions by T cells specific for $E7_{49-57}$. Furthermore, these results demonstrate that fusions in which E6 is carboxy terminal to E7 (E7E6 fusions) provide greater immune protection than their counterparts in which E6 is at the amino terminus (E6E7 fusions).

From the collective therapeutic efficacy data (FIGS. 6 and 7) across C3 and HLF16 tumor models, we can conclude that VRPs encoding mutant forms of HPV16 E6 and E7, without any auxiliary proteins, cytolines, or adjuvants, are highly effective at eradicating established murine tumors.

Example 5

Mutant E6 and E7 Expressing VRPS Do Not Induce Degradation of P53 and RB

The steady state levels of p53 and Rb in primary human MECs was assessed following infection with VRPs expressing wildtype HPV16 E6 and E7, as fusion or individual proteins, E7E6 TetM fusion protein, or GFP as a negative control.

Materials and Methods

Detection of p53 and Rb. Primary human mammary epithelial cells (MEC, Clonetics, San Diego, Calif.) were infected with VRPs encoding wildtype or mutant forms of E6 and E7 at MOI=10 and total cellular proteins harvested 16–20 hours later. To enhance p53 detection, cells were treated with 1.0 nM actinomycin D (Sigma, St. Louis, Mo.). Twenty-five micrograms of total protein were loaded per lane, electrophoresed by SDS-PAGE, and blotted to PVDF membranes. Western blots were probed using anti-p53 antibody (FL-393, Santa Cruz Biotech, Santa Cruz, Calif.) or anti-Rb antibody (Catalog # 554136, BD Pharmingen, San Diego, Calif.). Tubulin levels were monitored as loading controls by probing with an anti-tubulin antibody (H-235, Santa Cruz Biotech, Santa Cruz, Calif.).

Results

It was determined whether a mutant form of E6 and E7 fusion protein, when expressed in the context of VRP infection, would functionally inactivate p53 and Rb in comparison to wildtype versions of these proteins. The E7E6 TetM was selected because it demonstrated high antitumor efficacy (FIGS. 6 and 7) and contained a minimal number of mutations.

Primary human mammary epithelial cells (MEC) were infected with VRPs encoding HPV16 E6 alone, E7 alone, E7E6 wild-type, or E7E6 TetM. Approximately twenty hours post-infection with a MOI=10 of each of these VRPs, cell lysates containing equivalent amounts of total cellular protein were electrophoresed by SDS-PAGE, transferred to PVDF membranes, and probed with antibodies specific for p53 (FIG. 8A), Rb (FIG. 8B), and tubulin as a loading control. The results of these Western blots are shown in FIGS. 8A and 8B and are representative of two independent experiments.

MEC infected with VRPs encoding E6 alone or E7E6 wildtype fusion protein contained undetectable levels of p53 in contrast to MEC infected with E7E6 TetM which contained p53 levels comparable to negative control GFP-VRP infected samples (FIG. 8A). MEC infected with VRPs encoding E7 alone or E7E6 wildtype fusion protein contained undetectable levels of Rb in contrast to MEC infected with E7E6 TetM VRPs or GFP-VRPs (FIG. 8B). The presence of E7-containing fusion protein in the E7E6 wild-type and E7E6 TetM VRP infected samples was verified by probing those lanes with an anti-E7 monoclonal antibody (FIGS. 8A and B). The results show that p53 and Rb levels are grossly diminished in primary MEC expressing wildtype versions of E6 and E7 in the context of a VRP infection but are normal in MEC expressing E7E6 TetM following VRP infection.

In summary, VRP infection of MEC revealed grossly reclucea levels of p53 and Rb in cultures containing wild-type forms of E6 and E7, respectively; simply fusing E7 to E6 was not sufficient to impair the activity of either protein (FIGS. 8A and B). In contrast, MEC infected with E7E6 TetM VRPs containing E6 ($^{63}$C and $^{106}$C) and E7 ($^{24}$C and $^{26}$E) mutations contained normal levels of p53 and Rb (FIGS. 8A and B), indicating these four mutations extinguished the primary oncogenic activity of these proteins. An assessment of the immortalization potential of E7E6 TetM VRPs revealed that MEC died following infection, which is an expected consequence of expression of the AV nonstructural proteins expressed by replicons (Griffith et al., Annu. Rev. Microbiol. 1997, 51:565–592) and further supports the safety of this vector.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Numerous references, including patents, patent applications and various publications are cited and discussed in the description of this invention. The citation and/or discussion of such references is provided merely to clarify the description of the present invention and is not an admission that any such reference is "prior art" to the invention described herein. All references cited and/or discussed in this specification are incorporated herein by reference in their entirety and to the same extent as if each reference was individually incorporated by reference.

---

What is claimed is:

1. An isolated mutant polypeptide comprising human papillomavirus E6 and E7 polypeptides, wherein the E7 polypeptide has mutations at any one or more of the amino acids corresponding to amino acids 24, 26 or 91 of SEQ ID NO: 14 and the E6 polypeptide has no mutations or has mutations at any one or more of the amino acids corresponding to amino acids 63 or 106 of SEQ ID NO: 13 and the mutant polypeptide retains at least approximately 30% of the immunogenicity of an isolated polypeptide comprising human wild-type papillomavirus E6 and E7.

2. The mutant polypeptide of claim 1 wherein the mutated amino acids are mutated to glycine.

3. The mutant polypeptide of claim 1 wherein the E7 polypeptide precedes the E6 polypeptide.

4. The mutant polypeptide of claim 2 wherein the E7 polypeptide precedes the E6 polypeptide.

5. An immunogenic composition comprising:
   (a) the mutant polypeptide of claim 1; and
   (b) a pharmaceutically acceptable carrier.

6. The immunogenic composition of claim 5 further comprising adjuvant.

7. The isolated mutant polypeptide of claim 1 wherein the E7 polypeptide has mutations in at least two of amino acids corresponding to amino acids 24, 26 and 91 of SEQ ID NO: 14 and the E6 polypeptide has one or more mutations at amino acids corresponding to amino acids 63 and 106 of SEQ ID NO: 13.

8. The isolated mutant polypeptide of claim 1, wherein the mutant polypeptide retains at least approximately the same immunogenicity as an isolated polypeptide comprising human wild-type papillomavirus E6 and E7.

9. The isolated mutant polypeptide of claim 1, wherein the E6 polypeptide has mutations at any one or more of the amino acids corresponding to amino acids 63 or 106 of SEQ ID NO: 13.

10. A method for producing an immune response in an individual, which method comprises administering to the individual the immunogenic composition of claim 5 in an amount sufficient to produce the immune response.

* * * * *

SEQUENCE LISTING

```
<160> NUMBER OF SEQ ID NOS: 65

<210> SEQ ID NO 1
<211> LENGTH: 248
<212> TYPE: PRT
<213> ORGANISM: Human papillomavirus type 16

<400> SEQUENCE: 1

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60
```

-continued

| | | | | | | | | | | | | | | |
|---|---|---|---|---|---|---|---|---|---|---|---|---|---|---|
|Lys|Cys|Leu|Lys|Phe|Tyr|Ser|Lys|Ile|Ser|Glu|Tyr|Arg|His|Tyr|Cys|
|65| | | |70| | | |75| | | |80| | |

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Glu Thr Gln Leu His Gly Asp Thr Pro Thr Leu His Glu
145                 150                 155                 160

Tyr Met Leu Asp Leu Gln Pro Glu Thr Thr Asp Leu Tyr Cys Tyr Glu
                165                 170                 175

Gln Leu Asn Asp Ser Ser Glu Glu Glu Asp Glu Ile Asp Gly Pro Ala
            180                 185                 190

Gly Gln Ala Glu Pro Asp Arg Ala His Tyr Asn Ile Val Thr Phe Cys
            195                 200                 205

Cys Lys Cys Asp Ser Thr Leu Arg Leu Cys Val Gln Ser Thr His Val
    210                 215                 220

Asp Ile Arg Thr Leu Glu Asp Leu Leu Met Gly Thr Leu Gly Ile Val
225                 230                 235                 240

Cys Pro Ile Cys Ser Gln Lys Pro
                245

<210> SEQ ID NO 2
<211> LENGTH: 747
<212> TYPE: DNA
<213> ORGANISM: Human papillomavirus type 16

<400> SEQUENCE: 2

```
atgtttcagg acccacagga gcgacccaga aagttaccac agttatgcac agagctgcaa      60
acaactatac atgatataat attagaatgt gtgtactgca agcaacagtt actgcgacgt     120
gaggtatatg actttgcttt tcgggattta tgcatagtat atagagatgg gaatccatat     180
gctgtatgtg ataaatgttt aaagttttat tctaaaatta gtgagtatag acattattgt     240
tatagtgtgt atggaacaac attagaacag caatacaaca aaccgttgtg tgatttgtta     300
attaggtgta ttaactgtca aaagccactg tgtcctgaag aaaagcaaag acatctggac     360
aaaaagcaaa gattccataa tataaggggt cggtggaccg gtcgatgtat gtcttgttgc     420
agatcatcaa gaacacgtag agaaacccag ctgcatggag atacacctac attgcatgaa     480
tatatgttag atttgcaacc agagacaact gatctctact gttatgagca attaaatgac     540
agctcagagg aggaggatga aatagatggt ccagctggac aagcagaacc ggacagagcc     600
cattacaata ttgtaacctt ttgttgcaag tgtgactcta cgcttcggtt gtgcgtacaa     660
agcacacacg tagacattcg tactttggaa gacctgttaa tgggcacact aggaattgtg     720
tgccccatct gttctcagaa accataa                                          747
```

<210> SEQ ID NO 3
<211> LENGTH: 248
<212> TYPE: PRT
<213> ORGANISM: Human papillomavirus type 16

<400> SEQUENCE: 3

Met Phe Gln Asp Pro Gln Glu Arg Pro Arg Lys Leu Pro Gln Leu Cys

```
              1               5                  10                 15
            Thr Glu Leu Gln Thr Thr Ile His Asp Ile Ile Leu Glu Cys Val Tyr
                           20                  25                  30
            Cys Lys Gln Gln Leu Leu Arg Arg Glu Val Tyr Asp Phe Ala Phe Arg
                       35                  40                  45
            Asp Leu Cys Ile Val Tyr Arg Asp Gly Asn Pro Tyr Ala Val Gly Asp
                   50                  55                  60
            Lys Cys Leu Lys Phe Tyr Ser Lys Ile Ser Glu Tyr Arg His Tyr Cys
             65                  70                  75                  80
            Tyr Ser Val Tyr Gly Thr Thr Leu Glu Gln Gln Tyr Asn Lys Pro Leu
                               85                  90                  95
            Cys Asp Leu Leu Ile Arg Cys Ile Asn Gly Gln Lys Pro Leu Cys Pro
                           100                 105                 110
            Glu Glu Lys Gln Arg His Leu Asp Lys Lys Gln Arg Phe His Asn Ile
                       115                 120                 125
            Arg Gly Arg Trp Thr Gly Arg Cys Met Ser Cys Cys Arg Ser Ser Arg
                   130                 135                 140
            Thr Arg Arg Glu Thr Gln Leu His Gly Asp Thr Pro Thr Leu His Glu
            145                 150                 155                 160
            Tyr Met Leu Asp Leu Gln Pro Glu Thr Thr Asp Leu Tyr Gly Tyr Gly
                           165                 170                 175
            Gln Leu Asn Asp Ser Ser Glu Glu Asp Glu Ile Asp Gly Pro Ala
                       180                 185                 190
            Gly Gln Ala Glu Pro Asp Arg Ala His Tyr Asn Ile Val Thr Phe Cys
                   195                 200                 205
            Cys Lys Cys Asp Ser Thr Leu Arg Leu Cys Val Gln Ser Thr His Val
                   210                 215                 220
            Asp Ile Arg Thr Leu Glu Asp Leu Leu Met Gly Thr Leu Gly Ile Val
            225                 230                 235                 240
            Cys Pro Ile Cys Ser Gln Lys Pro
                           245

<210> SEQ ID NO 4
<211> LENGTH: 747
<212> TYPE: DNA
<213> ORGANISM: Human papillomavirus type 16

<400> SEQUENCE: 4
atgtttcagg acccacagga gcgacccaga aagttaccac agttatgcac agagctgcaa       60
acaactatac atgatataat attagaatgt gtgtactgca agcaacagtt actgcgacgt      120
gaggtatatg actttgcttt tcgggattta tgcatagtat atagagatgg gaatccatat      180
gctgtaggtg ataaatgttt aaagttttat tctaaaatta gtgagtatag acattattgt      240
tatagtgtgt atggaacaac attagaacag caatacaaca accgttgtgt tgatttgtta      300
attaggtgta ttaacggtca aaagccactg tgtcctgaag aaaagcaaag acatctggac      360
aaaaagcaaa gattccataa tataaggggt cggtggaccg tcgatgtat gtcttgttgc      420 agatcatcaa gaacacgtag agaaacccag ctgcatggag atacacctac attgcatgaa      480
tatatgttag atttgcaacc agagacaact gatctctacg gttatgggca attaaatgac      540
agctcagagg aggaggatga aatagatggt ccagctggac aagcagaacc ggacagagcc      600
cattacaata ttgtaacctt ttgttgcaag tgtgactcta cgcttcggtt gtgcgtacaa      660
agcacacacg tagacattcg tactttggaa gacctgttaa tgggcacact aggaattgtg      720
```

```
tgccccatct gttctcagaa accataa                                        747
```

<210> SEQ ID NO 5
<211> LENGTH: 248
<212> TYPE: PRT
<213> ORGANISM: Human papillomavirus type 16

<400> SEQUENCE: 5

```
Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Gly Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Gly Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu His Gly Asp Thr Pro Thr Leu His Glu
145                 150                 155                 160

Tyr Met Leu Asp Leu Gln Pro Glu Thr Thr Asp Leu Tyr Gly Tyr Gly
                165                 170                 175

Gln Leu Asn Asp Ser Ser Glu Glu Glu Asp Glu Ile Asp Gly Pro Ala
            180                 185                 190

Gly Gln Ala Glu Pro Asp Arg Ala His Tyr Asn Ile Val Thr Phe Cys
        195                 200                 205

Cys Lys Cys Asp Ser Thr Leu Arg Leu Cys Val Gln Ser Thr His Val
    210                 215                 220

Asp Ile Arg Thr Leu Glu Asp Leu Leu Met Gly Thr Leu Gly Ile Val
225                 230                 235                 240

Gly Pro Ile Cys Ser Gln Lys Pro
                245
```

<210> SEQ ID NO 6
<211> LENGTH: 747
<212> TYPE: DNA
<213> ORGANISM: Human papillomavirus type 16

<400> SEQUENCE: 6

```
atgtttcagg acccacagga gcgacccaga aagttaccac agttatgcac agagctgcaa     60
acaactatac atgatataat attagaatgt gtgtactgca agcaacagtt actgcgacgt    120
gaggtatatg actttgcttt tcgggattta tgcatagtat atagagatgg gaatccatat    180
gctgtaggtg ataatgtttt aagttttat tctaaaatta gtgagtatag acattattgt    240
tatagtgtgt atggaacaac attagaacag caatacaaca aaccgttgtg tgatttgtta    300
attaggtgta ttaacggtca aaagccactg tgtcctgaag aaaagcaaag acatctggac    360
aaaaagcaaa gattccataa tataaggggt cggtggaccg gtcgatgtat gtcttgttgc    420
```

```
agatcatcaa gaacacgtag agaaacccag ctgcatggag atacacctac attgcatgaa    480
tatatgttag atttgcaacc agagacaact gatctctacg ttatgggca attaaatgac    540 agctcagagg aggaggatga aatagatggt ccagctggac aagcagaacc ggacagagcc    600
cattacaata ttgtaacctt tgttgcaag tgtgactcta cgcttcggtt gtgcgtacaa     660
agcacacacg tagacattcg tactttggaa gacctgttaa tgggcacact aggaattgtg    720
ggccccatct gttctcagaa accataa                                        747
```

<210> SEQ ID NO 7
<211> LENGTH: 248
<212> TYPE: PRT
<213> ORGANISM: Human papillomavirus type 16

<400> SEQUENCE: 7

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro Phe Gln Asp Pro Gln Glu Arg Pro Arg Lys Leu Pro Gln Leu
            100                 105                 110

Cys Thr Glu Leu Gln Thr Thr Ile His Asp Ile Ile Leu Glu Cys Val
        115                 120                 125

Tyr Cys Lys Gln Gln Leu Leu Arg Arg Glu Val Tyr Asp Phe Ala Phe
    130                 135                 140

Arg Asp Leu Cys Ile Val Tyr Arg Asp Gly Asn Pro Tyr Ala Val Cys
145                 150                 155                 160

Asp Lys Cys Leu Lys Phe Tyr Ser Lys Ile Ser Glu Tyr Arg His Tyr
                165                 170                 175

Cys Tyr Ser Val Tyr Gly Thr Thr Leu Glu Gln Gln Tyr Asn Lys Pro
            180                 185                 190

Leu Cys Asp Leu Leu Ile Arg Cys Ile Asn Cys Gln Lys Pro Leu Cys
        195                 200                 205

Pro Glu Glu Lys Gln Arg His Leu Asp Lys Lys Gln Arg Phe His Asn
    210                 215                 220

Ile Arg Gly Arg Trp Thr Gly Arg Cys Met Ser Cys Cys Arg Ser Ser
225                 230                 235                 240

Arg Thr Arg Arg Glu Thr Gln Leu
                245
```

<210> SEQ ID NO 8
<211> LENGTH: 747
<212> TYPE: DNA
<213> ORGANISM: Human papillomavirus type 16

<400> SEQUENCE: 8

```
atgcatggag atacacctac attgcatgaa tatatgttag atttgcaacc agagacaact    60
```

-continued

```
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accatttcag    300
gacccacagg agcgacccag aaagttacca cagttatgca cagagctgca acaactata     360 catgatataa tattagaatg tgtgtactgc aagcaacagt tactgcgacg tgaggtatat    420
gactttgctt ttcgggattt atgcatagta tatagagatg gaatccata tgctgtatgt     480 gataaatgtt taaagtttta ttctaaaatt agtgagtata gacattattg ttatagtgtg    540
tatggaacaa cattagaaca gcaatacaac aaaccgttgt gtgatttgtt aattaggtgt    600
attaactgtc aaaagccact gtgtcctgaa gaaaagcaaa gacatctgga caaaaagcaa    660
agattccata atataagggg tcggtggacc ggtcgatgta tgtcttgttg cagatcatca    720
agaacacgta gagaaaccca gctgtaa                                         747
```

<210> SEQ ID NO 9
<211> LENGTH: 248
<212> TYPE: PRT
<213> ORGANISM: Human papillomavirus type 16

<400> SEQUENCE: 9

```
Met His Gly Asp Thr Pro Thr Leu His Glu Tyr Met Leu Asp Leu Gln
  1               5                  10                  15

Pro Glu Thr Thr Asp Leu Tyr Gly Tyr Gly Gln Leu Asn Asp Ser Ser
             20                  25                  30

Glu Glu Glu Asp Glu Ile Asp Gly Pro Ala Gly Gln Ala Glu Pro Asp
         35                  40                  45

Arg Ala His Tyr Asn Ile Val Thr Phe Cys Cys Lys Cys Asp Ser Thr
     50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro Phe Gln Asp Pro Gln Glu Arg Pro Arg Lys Leu Pro Gln Leu
            100                 105                 110

Cys Thr Glu Leu Gln Thr Thr Ile His Asp Ile Ile Leu Glu Cys Val
        115                 120                 125

Tyr Cys Lys Gln Gln Leu Leu Arg Arg Glu Val Tyr Asp Phe Ala Phe
    130                 135                 140

Arg Asp Leu Cys Ile Val Tyr Arg Asp Gly Asn Pro Tyr Ala Val Gly
145                 150                 155                 160

Asp Lys Cys Leu Lys Phe Tyr Ser Lys Ile Ser Glu Tyr Arg His Tyr
                165                 170                 175

Cys Tyr Ser Val Tyr Gly Thr Thr Leu Glu Gln Gln Tyr Asn Lys Pro
            180                 185                 190

Leu Cys Asp Leu Leu Ile Arg Cys Ile Asn Gly Gln Lys Pro Leu Cys
        195                 200                 205

Pro Glu Glu Lys Gln Arg His Leu Asp Lys Lys Gln Arg Phe His Asn
    210                 215                 220

Ile Arg Gly Arg Trp Thr Gly Arg Cys Met Ser Cys Cys Arg Ser Ser
225                 230                 235                 240

Arg Thr Arg Arg Glu Thr Gln Leu
                245
```

-continued

<210> SEQ ID NO 10
<211> LENGTH: 747
<212> TYPE: DNA
<213> ORGANISM: Human papillomavirus type 16

<400> SEQUENCE: 10

| | | | | | |
|---|---|---|---|---|---|
| atgcatggag | atacacctac | attgcatgaa | tatatgttag | atttgcaacc | agagacaact | 60 |
| gatctctacg | gttatgggca | attaaatgac | agctcagagg | aggaggatga | aatagatggt | 120 |
| ccagctggac | aagcagaacc | ggacagagcc | cattacaata | ttgtaacctt | ttgttgcaag | 180 |
| tgtgactcta | cgcttcggtt | gtgcgtacaa | agcacacacg | tagacattcg | tactttggaa | 240 |
| gacctgttaa | tgggcacact | aggaattgtg | tgccccatct | gttctcagaa | accatttcag | 300 |
| gacccacagg | agcgacccag | aaagttacca | cagttatgca | cagagctgca | acaactata | 360 |
| catgatataa | tattagaatg | tgtgtactgc | aagcaacagt | tactgcgacg | tgaggtatat | 420 |
| gactttgctt | ttcgggattt | atgcatagta | tatagagatg | ggaatccata | tgctgtaggt | 480 |
| gataaatgtt | taaagtttta | ttctaaaatt | agtgagtata | gacattattg | ttatagtgtg | 540 |
| tatggaacaa | cattagaaca | gcaatacaac | aaaccgttgt | gtgatttgtt | aattaggtgt | 600 |
| attaacggtc | aaaagccact | gtgtcctgaa | gaaaagcaaa | gacatctgga | caaaaagcaa | 660 |
| agattccata | tataaggggt | cggtggacc | ggtcgatgta | tgtcttgttg | cagatcatca | 720 |
| agaacacgta | gagaaaccca | gctgtaa | | | | 747 |

<210> SEQ ID NO 11
<211> LENGTH: 248
<212> TYPE: PRT
<213> ORGANISM: Human papillomavirus type 16

<400> SEQUENCE: 11

Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro Phe Gln Asp Pro Gln Glu Arg Pro Arg Lys Leu Pro Gln Leu
            100                 105                 110

Cys Thr Glu Leu Gln Thr Thr Ile His Asp Ile Ile Leu Glu Cys Val
        115                 120                 125

Tyr Cys Lys Gln Gln Leu Leu Arg Arg Glu Val Tyr Asp Phe Ala Phe
    130                 135                 140

Arg Asp Leu Cys Ile Val Tyr Arg Asp Gly Asn Pro Tyr Ala Val Gly
145                 150                 155                 160

Asp Lys Cys Leu Lys Phe Tyr Ser Lys Ile Ser Glu Tyr Arg His Tyr
                165                 170                 175

Cys Tyr Ser Val Tyr Gly Thr Thr Leu Glu Gln Gln Tyr Asn Lys Pro
            180                 185                 190

Leu Cys Asp Leu Leu Ile Arg Cys Ile Asn Gly Gln Lys Pro Leu Cys
            195                 200                 205

Pro Glu Glu Lys Gln Arg His Leu Asp Lys Lys Gln Arg Phe His Asn
            210                 215                 220

Ile Arg Gly Arg Trp Thr Gly Arg Cys Met Ser Cys Cys Arg Ser Ser
225                 230                 235                 240

Arg Thr Arg Arg Glu Thr Gln Leu
                245

<210> SEQ ID NO 12
<211> LENGTH: 747
<212> TYPE: DNA
<213> ORGANISM: Human papillomavirus type 16

<400> SEQUENCE: 12

```
atgcatggag atacacctac attgcatgaa tatatgttag atttgcaacc agagacaact      60
gatctctacg gttatgggca attaaatgac agctcagagg aggaggatga aatagatggt     120
ccagctggac aagcagaacc ggacagagcc cattacaata ttgtaacctt ttgttgcaag     180
tgtgactcta cgcttcggtt gtgcgtacaa agcacacacg tagacattcg tactttggaa     240
gacctgttaa tgggcacact aggaattgtg ggccccatct gttctcagaa accatttcag     300
gacccacagg agcgacccag aaagttacca cagttatgca cagagctgca acaactata      360
catgatataa tattagaatg tgtgtactgc aagcaacagt tactgcgacg tgaggtatat     420
gactttgctt tcgggatttt atgcatagta tatagagatg gaatcccata tgctgtaggt     480
gataaatgtt taaagtttta ttctaaaatt agtgagtata gacattattg ttatagtgtg     540
tatggaacaa cattagaaca gcaatacaac aaaccgttgt gtgatttgtt aattaggtgt     600
attaacggtc aaaagccact gtgtcctgaa gaaaagcaaa gacatctgga caaaaagcaa     660
agattccata atataagggg tcggtggacc ggtcgatgta tgtcttgttg cagatcatca     720
agaacacgta gagaaaccca gctgtaa                                         747
```

<210> SEQ ID NO 13
<211> LENGTH: 151
<212> TYPE: PRT
<213> ORGANISM: Human papillomavirus type 16

<400> SEQUENCE: 13

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg

```
                      130                 135                 140
Thr Arg Arg Glu Thr Gln Leu
145                 150

<210> SEQ ID NO 14
<211> LENGTH: 98
<212> TYPE: PRT
<213> ORGANISM: Human papillomavirus type 16

<400> SEQUENCE: 14

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 15
<211> LENGTH: 158
<212> TYPE: PRT
<213> ORGANISM: Human papillomavirus type 18

<400> SEQUENCE: 15

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Glu Thr Gln Val
145                 150                 155

<210> SEQ ID NO 16
<211> LENGTH: 149
<212> TYPE: PRT
<213> ORGANISM: Human papillomavirus type 31

<400> SEQUENCE: 16
```

```
Met Phe Lys Asn Pro Ala Glu Arg Pro Arg Lys Leu His Glu Leu Ser
1               5                   10                  15

Ser Ala Leu Glu Ile Pro Tyr Asp Glu Leu Arg Leu Asn Cys Val Tyr
            20                  25                  30

Cys Lys Gly Gln Leu Thr Glu Thr Glu Val Leu Asp Phe Ala Phe Thr
        35                  40                  45

Asp Leu Thr Ile Val Tyr Arg Asp Asp Thr Pro His Gly Val Cys Thr
    50                  55                  60

Lys Cys Leu Arg Phe Tyr Ser Lys Val Ser Glu Phe Arg Trp Tyr Arg
65                  70                  75                  80

Tyr Ser Val Tyr Gly Thr Thr Leu Glu Lys Leu Thr Asn Lys Gly Ile
                85                  90                  95

Cys Asp Leu Leu Ile Arg Cys Ile Thr Cys Gln Arg Pro Leu Cys Pro
                100                 105                 110

Glu Glu Lys Gln Arg His Leu Asp Lys Lys Arg Phe His Asn Ile
    115                 120                 125

Gly Gly Arg Trp Thr Gly Arg Cys Ile Ala Cys Trp Arg Arg Pro Arg
130                 135                 140

Thr Glu Thr Gln Val
145
```

```
<210> SEQ ID NO 17
<211> LENGTH: 149
<212> TYPE: PRT
<213> ORGANISM: Human papillomavirus type 33

<400> SEQUENCE: 17
```

```
Met Phe Gln Asp Thr Glu Glu Lys Pro Arg Thr Leu His Asp Leu Cys
1               5                   10                  15

Gln Ala Leu Glu Thr Thr Ile His Asn Ile Glu Leu Gln Cys Val Glu
            20                  25                  30

Cys Lys Lys Pro Leu Gln Arg Ser Glu Val Tyr Asp Phe Ala Phe Ala
        35                  40                  45

Asp Leu Thr Val Val Tyr Arg Glu Gly Asn Pro Phe Gly Ile Cys Lys
    50                  55                  60

Leu Cys Leu Arg Phe Leu Ser Lys Ile Ser Glu Tyr Arg His Tyr Asn
65                  70                  75                  80

Tyr Ser Val Tyr Gly Asn Thr Leu Glu Gln Thr Val Lys Lys Pro Leu
                85                  90                  95

Asn Glu Ile Leu Ile Arg Cys Ile Ile Cys Gln Arg Pro Leu Cys Pro
                100                 105                 110

Gln Glu Lys Lys Arg His Val Asp Leu Asn Lys Arg Phe His Asn Ile
    115                 120                 125

Ser Gly Arg Trp Ala Gly Arg Cys Ala Ala Cys Trp Arg Ser Arg Arg
130                 135                 140

Arg Glu Thr Ala Leu
145
```

```
<210> SEQ ID NO 18
<211> LENGTH: 149
<212> TYPE: PRT
<213> ORGANISM: Human papillomavirus type 35

<400> SEQUENCE: 18
```

```
Met Phe Gln Asp Pro Ala Glu Arg Pro Tyr Lys Leu His Asp Leu Cys
1               5                   10                  15
```

-continued

Asn Glu Val Glu Glu Ser Ile His Glu Ile Cys Leu Asn Cys Val Tyr
            20                  25                  30

Cys Lys Gln Glu Leu Gln Arg Ser Glu Val Tyr Asp Phe Ala Cys Tyr
        35                  40                  45

Asp Leu Cys Ile Val Tyr Arg Glu Gly Gln Pro Tyr Gly Val Cys Met
    50                  55                  60

Lys Cys Leu Lys Phe Tyr Ser Lys Ile Ser Glu Tyr Arg Trp Tyr Arg
65                  70                  75                  80

Tyr Ser Val Tyr Gly Glu Thr Leu Glu Lys Gln Cys Asn Lys Gln Leu
                85                  90                  95

Cys His Leu Leu Ile Arg Cys Ile Thr Cys Gln Lys Pro Leu Cys Pro
            100                 105                 110

Val Glu Lys Gln Arg His Leu Glu Glu Lys Lys Arg Phe His Asn Ile
        115                 120                 125

Gly Gly Arg Trp Thr Gly Arg Cys Met Ser Cys Trp Lys Pro Thr Arg
    130                 135                 140

Arg Glu Thr Glu Val
145

<210> SEQ ID NO 19
<211> LENGTH: 158
<212> TYPE: PRT
<213> ORGANISM: Human papillomavirus type 39

<400> SEQUENCE: 19

Met Ala Arg Phe His Asn Pro Ala Glu Arg Pro Tyr Lys Leu Pro Asp
1               5                   10                  15

Leu Cys Thr Thr Leu Asp Thr Thr Leu Gln Asp Ile Thr Ile Ala Cys
            20                  25                  30

Val Tyr Cys Arg Arg Pro Leu Gln Gln Thr Glu Val Tyr Glu Phe Ala
        35                  40                  45

Phe Ser Asp Leu Tyr Val Val Tyr Arg Asp Gly Glu Pro Leu Ala Ala
    50                  55                  60

Cys Gln Ser Cys Ile Lys Phe Tyr Ala Lys Ile Arg Glu Leu Arg Tyr
65                  70                  75                  80

Tyr Ser Asp Ser Val Tyr Ala Thr Thr Leu Glu Asn Ile Thr Asn Thr
                85                  90                  95

Lys Leu Tyr Asn Leu Leu Ile Arg Cys Met Cys Cys Leu Lys Pro Leu
            100                 105                 110

Cys Pro Ala Glu Lys Leu Arg His Leu Asn Ser Lys Arg Arg Phe His
        115                 120                 125

Lys Ile Ala Gly Ser Tyr Thr Gly Gln Cys Arg Arg Cys Trp Thr Thr
    130                 135                 140

Lys Arg Glu Asp Arg Arg Leu Thr Arg Arg Glu Thr Gln Val
145                 150                 155

<210> SEQ ID NO 20
<211> LENGTH: 158
<212> TYPE: PRT
<213> ORGANISM: Human papillomavirus type 45

<400> SEQUENCE: 20

Met Ala Arg Phe Asp Asp Pro Lys Gln Arg Pro Tyr Lys Leu Pro Asp
1               5                   10                  15

Leu Cys Thr Glu Leu Asn Thr Ser Leu Gln Asp Val Ser Ile Ala Cys
            20                  25                  30

```
Val Tyr Cys Lys Ala Thr Leu Glu Arg Thr Glu Val Tyr Gln Phe Ala
        35                  40                  45

Phe Lys Asp Leu Cys Ile Val Tyr Arg Asp Cys Ile Ala Tyr Ala Ala
    50                  55                  60

Cys His Lys Cys Ile Asp Phe Tyr Ser Arg Ile Arg Glu Leu Arg Tyr
65                  70                  75                  80

Tyr Ser Asn Ser Val Tyr Gly Glu Thr Leu Glu Lys Ile Thr Asn Thr
                85                  90                  95

Glu Leu Tyr Asn Leu Leu Ile Arg Cys Leu Arg Cys Gln Lys Pro Leu
                100                 105                 110

Asn Pro Ala Glu Lys Arg Arg His Leu Lys Asp Lys Arg Arg Phe His
            115                 120                 125

Ser Ile Ala Gly Gln Tyr Arg Gly Gln Cys Asn Thr Cys Cys Asp Gln
        130                 135                 140

Ala Arg Gln Glu Arg Leu Arg Arg Arg Glu Thr Gln Val
145                 150                 155
```

<210> SEQ ID NO 21
<211> LENGTH: 151
<212> TYPE: PRT
<213> ORGANISM: Human papillomavirus type 51

<400> SEQUENCE: 21

```
Met Phe Glu Asp Lys Arg Glu Arg Pro Arg Thr Leu His Glu Leu Cys
1               5                   10                  15

Glu Ala Leu Asn Val Ser Met His Asn Ile Gln Val Val Cys Val Tyr
                20                  25                  30

Cys Lys Lys Glu Leu Cys Arg Ala Asp Val Tyr Asn Val Ala Phe Thr
            35                  40                  45

Glu Ile Lys Ile Val Tyr Arg Asp Asn Asn Pro Tyr Ala Val Cys Lys
        50                  55                  60

Gln Cys Leu Leu Phe Tyr Ser Lys Ile Arg Glu Tyr Arg Arg Tyr Ser
65                  70                  75                  80

Arg Ser Val Tyr Gly Thr Thr Leu Glu Ala Ile Thr Lys Lys Ser Leu
                85                  90                  95

Tyr Asp Leu Ser Ile Arg Cys His Arg Cys Gln Arg Pro Leu Gly Pro
                100                 105                 110

Glu Glu Lys Gln Lys Leu Val Asp Glu Lys Lys Arg Phe His Glu Ile
            115                 120                 125

Ala Gly Arg Trp Thr Gly Gln Cys Ala Asn Cys Trp Gln Arg Thr Arg
        130                 135                 140

Gln Arg Asn Glu Thr Gln Val
145                 150
```

<210> SEQ ID NO 22
<211> LENGTH: 148
<212> TYPE: PRT
<213> ORGANISM: Human papillomavirus type 52

<400> SEQUENCE: 22

```
Met Phe Glu Asp Pro Ala Thr Arg Pro Arg Thr Leu His Glu Leu Cys
1               5                   10                  15

Glu Val Leu Glu Glu Ser Val His Glu Ile Arg Leu Gln Cys Val Gln
                20                  25                  30

Cys Lys Lys Glu Leu Gln Arg Arg Glu Val Tyr Lys Phe Leu Phe Thr
            35                  40                  45
```

```
Asp Leu Arg Ile Val Tyr Arg Asp Asn Asn Pro Tyr Gly Val Cys Ile
    50                  55                  60

Met Cys Leu Arg Phe Leu Ser Lys Ile Ser Glu Tyr Arg His Tyr Gln
 65                  70                  75                  80

Tyr Ser Leu Tyr Gly Lys Thr Leu Glu Glu Arg Val Lys Lys Pro Leu
                 85                  90                  95

Ser Glu Ile Thr Ile Arg Cys Ile Ile Cys Gln Thr Pro Leu Cys Pro
            100                 105                 110

Glu Glu Lys Glu Arg His Val Asn Ala Asn Lys Arg Phe His Asn Ile
        115                 120                 125

Met Gly Arg Trp Thr Gly Arg Cys Ser Glu Cys Trp Arg Pro Arg Pro
   130                 135                 140

Val Thr Gln Val
145

<210> SEQ ID NO 23
<211> LENGTH: 155
<212> TYPE: PRT
<213> ORGANISM: Human papillomavirus type 56

<400> SEQUENCE: 23

Met Glu Pro Gln Phe Asn Asn Pro Gln Glu Arg Pro Arg Ser Leu His
1               5                   10                  15

His Leu Ser Glu Val Leu Glu Ile Pro Leu Ile Asp Leu Arg Leu Ser
            20                  25                  30

Cys Val Tyr Cys Lys Lys Glu Leu Thr Arg Ala Glu Val Tyr Asn Phe
        35                  40                  45

Ala Cys Thr Glu Leu Lys Leu Val Tyr Arg Asp Asp Phe Pro Tyr Ala
    50                  55                  60

Val Cys Arg Val Cys Leu Leu Phe Tyr Ser Lys Val Arg Lys Tyr Arg
 65                  70                  75                  80

Tyr Tyr Asp Tyr Ser Val Tyr Gly Ala Thr Leu Glu Ser Ile Thr Lys
                 85                  90                  95

Lys Gln Leu Cys Asp Leu Leu Ile Arg Cys Tyr Arg Cys Gln Ser Pro
            100                 105                 110

Leu Thr Pro Glu Glu Lys Gln Leu His Cys Asp Arg Lys Arg Arg Phe
        115                 120                 125

His Leu Ile Ala His Gly Trp Thr Gly Ser Cys Leu Gly Cys Trp Arg
   130                 135                 140

Gln Thr Ser Arg Glu Pro Arg Glu Ser Thr Val
145                 150                 155

<210> SEQ ID NO 24
<211> LENGTH: 149
<212> TYPE: PRT
<213> ORGANISM: Human papillomavirus type 58

<400> SEQUENCE: 24

Met Phe Gln Asp Ala Glu Glu Lys Pro Arg Thr Leu His Asp Leu Cys
1               5                   10                  15

Gln Ala Leu Glu Thr Ser Val His Glu Ile Glu Leu Lys Cys Val Glu
            20                  25                  30

Cys Lys Lys Thr Leu Gln Arg Ser Glu Val Tyr Asp Phe Val Phe Ala
        35                  40                  45

Asp Leu Arg Ile Val Tyr Arg Asp Gly Asn Pro Phe Ala Val Cys Lys
    50                  55                  60
```

```
Val Cys Leu Arg Leu Leu Ser Lys Ile Ser Glu Tyr Arg His Tyr Asn
 65                  70                  75                  80

Tyr Ser Leu Tyr Gly Asp Thr Leu Glu Gln Thr Leu Lys Lys Cys Leu
                 85                  90                  95

Asn Glu Ile Leu Ile Arg Cys Ile Ile Cys Gln Arg Pro Leu Cys Pro
            100                 105                 110

Gln Glu Lys Lys Arg His Val Asp Leu Asn Lys Arg Phe His Asn Ile
            115                 120                 125

Ser Gly Arg Trp Thr Gly Arg Cys Ala Val Cys Trp Arg Pro Arg Arg
    130                 135                 140

Arg Gln Thr Gln Val
145
```

<210> SEQ ID NO 25
<211> LENGTH: 160
<212> TYPE: PRT
<213> ORGANISM: Human papillomavirus type 59

<400> SEQUENCE: 25

```
Met Ala Arg Phe Glu Asp Pro Thr Gln Arg Pro Tyr Lys Leu Pro Asp
 1               5                  10                  15

Leu Ser Thr Thr Leu Asn Ile Pro Leu His Asp Ile Arg Ile Asn Cys
                20                  25                  30

Val Phe Cys Lys Gly Glu Leu Gln Glu Arg Glu Val Phe Glu Phe Ala
             35                  40                  45

Phe Asn Asp Leu Phe Ile Val Tyr Arg Asp Cys Thr Pro Tyr Ala Ala
     50                  55                  60

Cys Leu Lys Cys Ile Ser Phe Tyr Ala Arg Val Arg Glu Leu Arg Tyr
 65                  70                  75                  80

Tyr Arg Asp Ser Val Tyr Gly Glu Thr Leu Glu Ala Glu Thr Lys Thr
                 85                  90                  95

Pro Leu His Glu Leu Ile Arg Cys Tyr Arg Cys Leu Lys Pro Leu
            100                 105                 110

Cys Pro Thr Asp Lys Leu Lys His Ile Thr Glu Lys Arg Arg Phe His
            115                 120                 125

Asn Ile Ala Gly Ile Tyr Thr Gly Gln Cys Arg Gly Cys Arg Thr Arg
    130                 135                 140

Ala Arg His Leu Arg Gln Gln Arg Gln Ala Arg Ser Glu Thr Leu Val
145                 150                 155                 160
```

<210> SEQ ID NO 26
<211> LENGTH: 158
<212> TYPE: PRT
<213> ORGANISM: Human papillomavirus type 68

<400> SEQUENCE: 26

```
Met Ala Leu Phe His Asn Pro Glu Glu Arg Pro Tyr Lys Leu Pro Asp
 1               5                  10                  15

Leu Cys Arg Thr Leu Asp Thr Thr Leu His Asp Val Thr Ile Asp Cys
                20                  25                  30

Val Tyr Cys Arg Arg Gln Leu Gln Arg Thr Glu Val Tyr Glu Phe Ala
             35                  40                  45

Phe Ser Asp Leu Cys Val Val Tyr Arg Asp Gly Val Pro Phe Ala Ala
     50                  55                  60

Cys Gln Ser Cys Ile Lys Phe Tyr Ala Lys Ile Arg Glu Leu Arg Tyr
 65                  70                  75                  80
```

```
Tyr Ser Glu Ser Val Tyr Ala Thr Thr Leu Glu Thr Ile Thr Asn Thr
                85                  90                  95

Lys Leu Tyr Asn Leu Leu Ile Arg Cys Met Ser Cys Leu Lys Pro Leu
            100                 105                 110

Cys Pro Ala Glu Lys Leu Arg His Leu Thr Thr Lys Arg Arg Leu His
        115                 120                 125

Lys Ile Ala Gly Asn Phe Thr Gly Gln Cys Arg His Cys Trp Thr Ser
    130                 135                 140

Lys Arg Glu Asp Arg Arg Ile Arg Gln Glu Thr Gln Val
145                 150                 155

<210> SEQ ID NO 27
<211> LENGTH: 105
<212> TYPE: PRT
<213> ORGANISM: Human papillomavirus type 18

<400> SEQUENCE: 27

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 28
<211> LENGTH: 98
<212> TYPE: PRT
<213> ORGANISM: Human papillomavirus type 31

<400> SEQUENCE: 28

Met Arg Gly Glu Thr Pro Thr Leu Gln Asp Tyr Val Leu Asp Leu Gln
1               5                   10                  15

Pro Glu Ala Thr Asp Leu His Cys Tyr Glu Gln Leu Pro Asp Ser Ser
            20                  25                  30

Asp Glu Glu Asp Val Ile Asp Ser Pro Ala Gly Gln Ala Glu Pro Asp
        35                  40                  45

Thr Ser Asn Tyr Asn Ile Val Thr Phe Cys Cys Gln Cys Lys Ser Thr
    50                  55                  60

Leu Arg Leu Cys Val Gln Ser Thr Gln Val Asp Ile Arg Ile Leu Gln
65                  70                  75                  80

Glu Leu Leu Met Gly Ser Phe Gly Ile Val Cys Pro Asn Cys Ser Thr
                85                  90                  95

Arg Leu

<210> SEQ ID NO 29
<211> LENGTH: 97
<212> TYPE: PRT
<213> ORGANISM: Human papillomavirus type 33

<400> SEQUENCE: 29
```

```
Met Arg Gly His Lys Pro Thr Leu Lys Glu Tyr Val Leu Asp Leu Tyr
1               5                  10                  15

Pro Glu Pro Thr Asp Leu Tyr Cys Tyr Glu Gln Leu Ser Asp Ser Ser
            20                  25                  30

Asp Glu Asp Glu Gly Leu Asp Arg Pro Asp Gly Gln Ala Gln Pro Ala
        35                  40                  45

Thr Ala Asp Tyr Tyr Ile Val Thr Cys Cys His Thr Cys Asn Thr Thr
 50                  55                  60

Val Arg Leu Cys Val Asn Ser Thr Ala Ser Asp Leu Arg Thr Ile Gln
 65                  70                  75                  80

Gln Leu Leu Met Gly Thr Val Asn Ile Val Cys Pro Thr Cys Ala Gln
                 85                  90                  95

Gln

<210> SEQ ID NO 30
<211> LENGTH: 99
<212> TYPE: PRT
<213> ORGANISM: Human papillomavirus type 35

<400> SEQUENCE: 30

Met His Gly Glu Ile Thr Thr Leu Gln Asp Tyr Val Leu Asp Leu Glu
1               5                  10                  15

Pro Glu Ala Thr Asp Leu Tyr Cys Tyr Glu Gln Leu Cys Asp Ser Ser
            20                  25                  30

Glu Glu Glu Glu Asp Thr Ile Asp Gly Pro Ala Gly Gln Ala Lys Pro
        35                  40                  45

Asp Thr Ser Asn Tyr Asn Ile Val Thr Ser Cys Cys Lys Cys Glu Ala
 50                  55                  60

Thr Leu Arg Leu Cys Val Gln Ser Thr His Ile Asp Ile Arg Lys Leu
 65                  70                  75                  80

Glu Asp Leu Leu Met Gly Thr Phe Gly Ile Val Cys Pro Gly Cys Ser
                 85                  90                  95

Gln Arg Ala

<210> SEQ ID NO 31
<211> LENGTH: 109
<212> TYPE: PRT
<213> ORGANISM: Human papillomavirus type 39

<400> SEQUENCE: 31

Met Arg Gly Pro Lys Pro Thr Leu Gln Glu Ile Val Leu Asp Leu Cys
1               5                  10                  15

Pro Tyr Asn Glu Ile Gln Pro Val Asp Leu Val Cys His Glu Gln Leu
            20                  25                  30

Gly Glu Ser Glu Asp Glu Ile Asp Glu Pro Asp His Ala Val Asn His
        35                  40                  45

Gln His Gln Leu Leu Ala Arg Arg Asp Glu Pro Gln Arg His Thr Ile
 50                  55                  60

Gln Cys Ser Cys Cys Lys Cys Asn Asn Thr Leu Gln Leu Val Val Glu
 65                  70                  75                  80

Ala Ser Arg Asp Thr Leu Arg Gln Leu Gln Gln Leu Phe Met Asp Ser
                 85                  90                  95

Leu Gly Phe Val Cys Pro Trp Cys Ala Thr Ala Asn Gln
                100                 105
```

<210> SEQ ID NO 32
<211> LENGTH: 106
<212> TYPE: PRT
<213> ORGANISM: Human papillomavirus type 45

<400> SEQUENCE: 32

Met His Gly Pro Arg Glu Thr Leu Gln Glu Ile Val Leu His Leu Glu
1               5                   10                  15

Pro Gln Asn Glu Leu Asp Pro Val Asp Leu Leu Cys Tyr Glu Gln Leu
            20                  25                  30

Ser Glu Ser Glu Glu Asn Asp Glu Ala Asp Gly Val Ser His Ala
        35                  40                  45

Gln Leu Pro Ala Arg Arg Ala Glu Pro Gln Arg His Lys Ile Leu Cys
    50                  55                  60

Val Cys Cys Lys Cys Asp Gly Arg Ile Glu Leu Thr Val Glu Ser Ser
65                  70                  75                  80

Ala Glu Asp Leu Arg Thr Leu Gln Gln Leu Phe Leu Ser Thr Leu Ser
                85                  90                  95

Phe Val Cys Pro Trp Cys Ala Thr Asn Gln
            100                 105

<210> SEQ ID NO 33
<211> LENGTH: 101
<212> TYPE: PRT
<213> ORGANISM: Human papillomavirus type 51

<400> SEQUENCE: 33

Met Arg Gly Asn Val Pro Gln Leu Lys Asp Val Val Leu His Leu Thr
1               5                   10                  15

Pro Gln Thr Glu Ile Asp Leu Gln Cys Tyr Glu Gln Phe Asp Ser Ser
            20                  25                  30

Glu Glu Glu Asp Glu Val Asp Asn Met Arg Asp Gln Leu Pro Glu Arg
        35                  40                  45

Arg Ala Gly Gln Ala Thr Cys Tyr Arg Ile Glu Ala Pro Cys Cys Arg
    50                  55                  60

Cys Ser Ser Val Val Gln Leu Ala Val Glu Ser Ser Gly Asp Thr Leu
65                  70                  75                  80

Arg Val Val Gln Gln Met Leu Met Gly Glu Leu Ser Leu Val Cys Pro
                85                  90                  95

Cys Cys Ala Asn Asn
            100

<210> SEQ ID NO 34
<211> LENGTH: 99
<212> TYPE: PRT
<213> ORGANISM: Human papillomavirus type 52

<400> SEQUENCE: 34

Met Arg Gly Asp Lys Ala Thr Ile Lys Asp Tyr Ile Leu Asp Leu Gln
1               5                   10                  15

Pro Glu Thr Thr Asp Leu His Cys Tyr Glu Gln Leu Gly Asp Ser Ser
            20                  25                  30

Asp Glu Glu Asp Thr Asp Gly Val Asp Arg Pro Asp Gly Gln Ala Glu
        35                  40                  45

Gln Ala Thr Ser Asn Tyr Tyr Ile Val Thr Tyr Cys His Ser Cys Asp
    50                  55                  60

Ser Thr Leu Arg Leu Cys Ile His Ser Thr Ala Thr Asp Leu Arg Thr
65                  70                  75                  80

```
Leu Gln Gln Met Leu Leu Gly Thr Leu Gln Val Val Cys Pro Gly Cys
                85                  90                  95

Ala Arg Leu

<210> SEQ ID NO 35
<211> LENGTH: 105
<212> TYPE: PRT
<213> ORGANISM: Human papillomavirus type 56

<400> SEQUENCE: 35

Met His Gly Lys Val Pro Thr Leu Gln Asp Val Val Leu Glu Leu Thr
1               5                   10                  15

Pro Gln Thr Glu Ile Asp Leu Gln Cys Asn Glu Gln Leu Asp Ser Ser
            20                  25                  30

Glu Asp Glu Asp Glu Asp Val Asp His Leu Gln Glu Arg Pro Gln
        35                  40                  45

Gln Ala Arg Gln Ala Lys Gln His Thr Cys Tyr Leu Ile His Val Pro
    50                  55                  60

Cys Cys Glu Cys Lys Phe Val Val Gln Leu Asp Ile Gln Ser Thr Lys
65                  70                  75                  80

Glu Asp Leu Arg Val Val Gln Gln Leu Leu Met Gly Ala Leu Thr Val
                85                  90                  95

Thr Cys Pro Leu Cys Ala Ser Ser Asn
            100                 105

<210> SEQ ID NO 36
<211> LENGTH: 98
<212> TYPE: PRT
<213> ORGANISM: Human papillomavirus type 58

<400> SEQUENCE: 36

Met Arg Gly Asn Asn Pro Thr Leu Arg Glu Tyr Ile Leu Asp Leu His
1               5                   10                  15

Pro Glu Pro Thr Asp Leu Phe Cys Tyr Glu Gln Leu Cys Asp Ser Ser
            20                  25                  30

Asp Glu Asp Glu Ile Gly Leu Asp Gly Pro Asp Gly Gln Ala Gln Pro
        35                  40                  45

Ala Thr Ala Asn Tyr Tyr Ile Val Thr Cys Cys Tyr Thr Cys Gly Thr
    50                  55                  60

Thr Val Arg Leu Cys Ile Asn Ser Thr Thr Asp Val Arg Thr Leu
65                  70                  75                  80

Gln Gln Leu Leu Met Gly Thr Cys Thr Ile Val Cys Pro Ser Cys Ala
                85                  90                  95

Gln Gln

<210> SEQ ID NO 37
<211> LENGTH: 107
<212> TYPE: PRT
<213> ORGANISM: Human papillomavirus type 59

<400> SEQUENCE: 37

Met His Gly Pro Lys Ala Thr Leu Cys Asp Ile Val Leu Asp Leu Glu
1               5                   10                  15

Pro Gln Asn Tyr Glu Glu Val Asp Leu Val Cys Tyr Glu Gln Leu Pro
            20                  25                  30

Asp Ser Asp Ser Glu Asn Glu Lys Asp Glu Pro Asp Gly Val Asn His
        35                  40                  45
```

```
Pro Leu Leu Leu Ala Arg Arg Ala Glu Pro Gln Arg His Asn Ile Val
        50                  55                  60
Cys Val Cys Cys Lys Cys Asn Asn Gln Leu Gln Leu Val Val Glu Thr
 65                  70                  75                  80
Ser Gln Asp Gly Leu Arg Ala Leu Gln Gln Leu Phe Met Asp Thr Leu
                 85                  90                  95
Ser Phe Val Cys Pro Leu Cys Ala Ala Asn Gln
                100                 105
```

<210> SEQ ID NO 38
<211> LENGTH: 110
<212> TYPE: PRT
<213> ORGANISM: Human papillomavirus type 68

<400> SEQUENCE: 38

```
Met His Gly Pro Lys Pro Thr Val Gln Glu Ile Val Leu Glu Leu Cys
 1               5                  10                  15
Pro Tyr Asn Glu Ile Gln Pro Val Asp Leu Val Cys His Glu Gln Leu
                20                  25                  30
Gly Asp Ser Asp Glu Ile Asp Glu Pro Asp His Ala Val Asn His
                35                  40                  45
His Gln His Leu Leu Ala Arg Arg Asp Glu Gln Gln Arg His Arg
        50                  55                  60
Ile Gln Cys Leu Cys Cys Lys Cys Asn Lys Ala Leu Gln Leu Val Val
 65                  70                  75                  80
Glu Ala Ser Arg Asp Asn Leu Arg Thr Leu Gln Gln Leu Phe Met Asp
                 85                  90                  95
Ser Leu Asn Phe Val Cys Pro Trp Cys Ala Thr Glu Thr Gln
                100                 105                 110
```

<210> SEQ ID NO 39
<211> LENGTH: 152
<212> TYPE: PRT
<213> ORGANISM: Human papillomavirus
<220> FEATURE:
<221> NAME/KEY: MISC_FEATURE
<222> LOCATION: (1)..(152)
<223> OTHER INFORMATION: where Xaa is any amino acid

<400> SEQUENCE: 39

```
Xaa Xaa Xaa Phe Glx Asp Pro Xaa Glu Arg Pro Xaa Lys Leu Xaa Asp
 1               5                  10                  15
Leu Cys Xaa Xaa Leu Xaa Xaa Xaa His Asx Ile Xaa Xaa Xaa Cys
                20                  25                  30
Val Tyr Cys Lys Xaa Glx Leu Glx Arg Xaa Glu Val Tyr Xaa Phe Ala
                 35                  40                  45
Phe Xaa Asp Leu Xaa Ile Val Tyr Arg Asp Xaa Xaa Pro Xaa Ala Xaa
        50                  55                  60
Cys Xaa Xaa Cys Leu Xaa Phe Tyr Ser Lys Ile Xaa Glu Xaa Arg Xaa
 65                  70                  75                  80
Tyr Xaa Xaa Ser Val Tyr Gly Xaa Thr Leu Glu Xaa Xaa Thr Xaa Lys
                 85                  90                  95
Xaa Leu Xaa Asx Leu Leu Ile Arg Cys Xaa Xaa Cys Gln Xaa Pro Leu
                100                 105                 110
Cys Pro Xaa Glu Lys Xaa Arg His Xaa Asx Xaa Lys Xaa Arg Phe His
        115                 120                 125
Asn Ile Xaa Gly Xaa Trp Thr Gly Xaa Cys Xaa Xaa Cys Trp Xaa Xaa
```

```
                130               135               140
Xaa Arg Xaa Xaa Xaa Xaa Xaa Xaa
145                 150
```

<210> SEQ ID NO 40
<211> LENGTH: 104
<212> TYPE: PRT
<213> ORGANISM: Human papillomavirus
<220> FEATURE:
<221> NAME/KEY: MISC_FEATURE
<222> LOCATION: (1)..(104)
<223> OTHER INFORMATION: where Xaa is any amino acid

<400> SEQUENCE: 40

```
Met Xaa Gly Xaa Xaa Pro Thr Leu Xaa Xaa Xaa Val Leu Asp Leu Xaa
1               5                   10                  15

Pro Glx Xaa Xaa Xaa Asp Leu Xaa Cys Tyr Glu Gln Leu Xaa Asp Ser
            20                  25                  30

Xaa Xaa Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Tyr Xaa Ile Xaa Xaa Xaa Xaa Cys
    50                  55                  60

Cys Xaa Cys Xaa Xaa Xaa Xaa Xaa Leu Xaa Val Glx Ser Xaa Xaa Xaa
65                  70                  75                  80

Asp Leu Arg Xaa Leu Gln Gln Leu Leu Met Gly Thr Leu Xaa Xaa Val
                85                  90                  95

Cys Pro Xaa Cys Ala Xaa Xaa Xaa
            100
```

<210> SEQ ID NO 41
<211> LENGTH: 9
<212> TYPE: PRT
<213> ORGANISM: Human papillomavirus type 16

<400> SEQUENCE: 41

```
Arg Ala His Tyr Asn Ile Val Thr Phe
1               5
```

<210> SEQ ID NO 42
<211> LENGTH: 477
<212> TYPE: DNA
<213> ORGANISM: Human papillomavirus type 18

<400> SEQUENCE: 42

```
atggcgcgct ttgaggatcc aacacggcga ccctacaagc tacctgatct gtgcacggaa      60
ctgaacactt cactgcaaga catagaaata acctgtgtat attgcaagac agtattggaa    120
cttacagagg tatttgaatt tgcatttaaa gatttatttg tggtgtatag agacagtata    180
ccccatgctg catgccataa atgtatagat tttattcta gaattagaga attaagacat     240
tattcagact ctgtgtatgg agacacattg gaaaaactaa ctaacactgg ttatacaat    300
ttattaataa ggtgcctgcg gtgccagaaa ccgttgaatc cagcgagaaaa acttagacac   360
cttaatgaaa aacgacgatt tcacaacata gctgggcact atagaggcca gtgccattcg   420
tgctgcaacc gagcacgaca ggaacgactc caacgacgca gagaaacaca agtataa      477
```

<210> SEQ ID NO 43
<211> LENGTH: 474
<212> TYPE: DNA
<213> ORGANISM: Human papillomavirus type 31

```
<400> SEQUENCE: 43
atgttcaaaa atcctgcaga aagacctcgg aaattgcatg aactaagctc ggcattggaa      60 atacccctacg atgaactaag attgaattgt gtctactgca aggtcagtt  aacagaaaca     120 gaggtattag attttgcatt tacagattta acaatagtat ataggacga  cacaccacac     180 ggagtgtgta caaatgtttt aagattttat tcaaaagtaa gtgaatttag atggtataga    240
tatagtgtgt atggaacaac attagaaaaa ttgacaaaca aaggtatatg tgatttgtta    300
attaggtgta taacgtgtca agaccgttg tgtccagaag aaaaacaaag acatttggat     360
aaaaagaaac gattccacaa catagaggga aggtggacag gacgttgcat agcatgttgg    420
agaagacctc gtactgaaac ccaagtgtaa acatgcgtgg agaaacacct acgt           474

<210> SEQ ID NO 44
<211> LENGTH: 450
<212> TYPE: DNA
<213> ORGANISM: Human papillomavirus type 33

<400> SEQUENCE: 44
atgtttcaag acactgagga aaaaccacga acattgcatg atttgtgcca agcattggag      60
acaactatac acaacattga actacagtgc gtggaatgca aaaaaccttt gcaacgatct    120
gaggtatatg attttgcatt tgcagattta acagttgtat atagagaggg aaatccattt    180
ggaatatgta aactgtgttt gcggttctta tctaaaatta gtgaatatag acattataat    240
tattctgtat atggaaatac attagaacaa acagttaaaa aacctttaaa tgaaatatta    300
attaggtgta ttatatgtca agacctttg tgtcctcaag aaaaaaaacg acatgtggat    360
ttaaacaaac gatttcataa tatttcgggt cgttgggcag ggcgctgtgc ggcgtgttgg    420
aggtcccgac gtagagaaac tgcactgtga                                      450

<210> SEQ ID NO 45
<211> LENGTH: 450
<212> TYPE: DNA
<213> ORGANISM: Human papillomavirus type 35

<400> SEQUENCE: 45
atgtttcagg acccagctga acgaccttac aaactgcatg atttgtgcaa cgaggtagaa      60
gaaagcatcc atgaaatttg tttgaattgt gtatactgca acaagaatt  acagcggagt    120 gaggtatatg actttgcatg ctatgatttg tgtatagtat atagagaagg ccagccatat    180
ggagtatgca tgaaatgttt aaaattttat tcaaaaataa gtgaatatag atggtataga    240
tatagtgtgt atggagaaac gttagaaaaa caatgcaaca acagttatg  tcatttatta    300 attaggtgta ttacatgtca aaaaccgctg tgtccagttg aaaagcaaag catttagaa     360 gaaaaaaaac gattccataa catcgtgga  cggtggacag tcggtgtat  gtcctgttgg    420 aaaccaacac gtagagaaac cgaggtgtaa                                       450

<210> SEQ ID NO 46
<211> LENGTH: 477
<212> TYPE: DNA
<213> ORGANISM: Human papillomavirus type 39

<400> SEQUENCE: 46
atggcgcgat ttcacaatcc tgcagaacgg ccatacaaat tgccagacct gtgcacaacg      60
ctggacacca ccttgcagga cattacaata gcctgtgtct attgcagacg accactacag    120
caaaccgagg tatatgaatt tgcatttagt gatttatatg tagtatatag ggacgggaa     180
```

```
ccactagctg catgccaatc atgtataaaa ttttatgcta aaatacggga gctacgatat      240
tactcggact cggtgtatgc aactacatta gaaaatataa ctaatacaaa gttatataat      300
ttattaataa ggtgcatgtg ttgtctgaaa ccgctgtgtc cagcagaaaa attaagacac      360
ctaaatagca aacgaagatt tcataaaata gcaggaagct atacaggaca gtgtcgacgg      420
tgctggacca caaaacggga ggaccgcaga ctaacacgaa gagaaaccca agtataa        477

<210> SEQ ID NO 47
<211> LENGTH: 477
<212> TYPE: DNA
<213> ORGANISM: Human papillomavirus type 45

<400> SEQUENCE: 47
atggcgcgct ttgacgatcc aaagcaacga ccctacaagc taccagattt gtgcacagaa       60
ttgaatacat cactacaaga cgtatctatt gcctgtgtat attgcaaagc aacattggaa      120
cgcacagagg tatatcaatt tgcttttaaa gatttatgta tagtgtatag agactgtata      180
gcatatgctg catgccataa atgtatagac ttttattcca gaattagaga attaagatat      240
tattcaaact ctgtatatgg agagacactg aaaaaaataa ctaatacaga gttgtataat      300
ttgttaataa ggtgcctgcg gtgccagaaa ccattgaacc cagcagaaaa acgtagacac      360
cttaaggaca aacgaagatt tcacagcata gctggacagt accgagggca gtgtaataca      420
tgttgtgacc aggcacggca agaaagactt cgcagacgta gggaaacaca agtatag        477

<210> SEQ ID NO 48
<211> LENGTH: 456
<212> TYPE: DNA
<213> ORGANISM: Human papillomavirus type 51

<400> SEQUENCE: 48
atgttcgaag acaagaggga aagaccacga acgctgcatg aattatgtga agctttgaac       60
gtttctatgc acaatataca ggtagtgtgt gtgtattgta aaaggaatt atgtagagca      120 gatgtatata atgtagcatt tactgaaatt aagattgtat atagggataa taatccatat      180
gcagtatgca acaatgtttt actgttttat tcaaaaatta gagagtatag acgttatagc      240
aggtctgtgt atggtactac attagaggca attactaaaa aaagcttata tgatttatcg      300
ataaggtgtc atagatgtca aagaccactt gggcctgaag aaaagcaaaa attggtggac      360
gaaaaaaaaa ggttccatga aatagcggga cgttggacgg ggcaatgcgc taattgctgg      420
caacgtacac gacaacgtaa cgaaacccaa gtgtaa                               456

<210> SEQ ID NO 49
<211> LENGTH: 447
<212> TYPE: DNA
<213> ORGANISM: Human papillomavirus type 52

<400> SEQUENCE: 49
atgtttgagg atccagcaac acgaccccgg accctgcacg aattgtgtga ggtgctggaa       60
gaatcggtgc atgaaataag gctgcagtgt gtgcagtgca aaaagagct acaacgaaga      120 gaggtataca gtttctatt tacagattta cgaatagtat atagagacaa taatccatat      180
ggcgtgtgta ttatgtgcct acgcttttta tctaagataa gtgaatatag gcattatcaa      240
tattcactgt atgggaaaac attagaagag agggtaaaaa aaccattaag tgaaataact      300
attagatgta taatttgtca aacgccatta tgtcctgaag aaaagaaag acatgttaat      360
```

```
gcaaacaagc gatttcataa tattatgggt cgttggacag ggcgctgttc agagtgttgg    420
agaccccgac ctgtgaccca agtgtaa                                       447
```

<210> SEQ ID NO 50
<211> LENGTH: 465
<212> TYPE: DNA
<213> ORGANISM: Human papillomavirus type 56

<400> SEQUENCE: 50

```
atggagccac aattcaacaa tccacaggaa cgtccacgaa gcctgcacca cttgagtgag    60
gtattagaaa tacctttaat tgatcttaga ttatcatgtg tatattgcaa aaagaactaa   120
acacgtgctg aggtatataa ttttgcatgc actgaattaa aattagtgta tagggatgat   180
tttccttatg cagtgtgcag agtatgttta ttgtttttata gtaaagttag aaaatatagg   240
tattatgact attcagtgta tggagctaca ctagaaagta taactaaaaa acagttatgt   300
gatttattaa taggtgctca cagatgtcaa agtccgttaa ctccggagga aaagcaattg   360
cattgtgaca gaaaaagacg atttcatcta atagcacatg gttggaccgg gtcatgtttg   420
gggtgctgga gacaaacatc tagagaacct agagaatcta cagta                   465
```

<210> SEQ ID NO 51
<211> LENGTH: 450
<212> TYPE: DNA
<213> ORGANISM: Human papillomavirus type 58

<400> SEQUENCE: 51

```
atgttccagg acgcagagga gaaaccacgg acattgcatg atttgtgtca ggcgttggag    60
acatctgtgc atgaaatcga attgaaatgc gttgaatgca aaaagacttt gcagcgatct   120
gaggtatatg actttgtatt tgcagattta agaatagtgt atagagatgg aaatccattt   180
gcagtatgta aagtgtgctt acgattgcta tctaaaataa gtgagtatag acattataat   240
tattcgctat atggagacac attagaacaa acactaaaaa agtgtttaaa tgaaatatta   300
attagatgta ttatttgtca agaccattg tgtccacaag aaaaaaaaag gcatgtggat   360
ttaaacaaaa ggtttcataa tatttcgggt cgttggacag ggcgctgtgc agtgtgttgg   420
agaccccgac gtagacaaac acaagtgtaa                                    450
```

<210> SEQ ID NO 52
<211> LENGTH: 483
<212> TYPE: DNA
<213> ORGANISM: Human papillomavirus type 59

<400> SEQUENCE: 52

```
atggcacgct ttgaggatcc tacacaacga ccatacaaac tgcctgattt gagcacaaca    60
ttgaatattc ctctgcatga tattcgcatc aattgtgtgt tttgcaaagg ggaactgcaa   120
gaaagagagg tatttgaatt tgcttttaat gacttattta gtgtatatag agactgtaca   180
ccgtatgcag cgtgtctgaa atgcatttca ttttatgcaa gagtaagaga attaagatat   240
tatagagatt ccgtgtatgg agaaacatta gaggctgaaa ccaagacacc gttacatgag   300
ctgctgatac gctgttatag atgcctaaaa cctctatgtc caacagataa attaaagcat   360
ataactgaaa aaagaagatt ccataatata gctggaatat atacaggaca gtgtcgtggg   420
tgtcggaccc gagcaagaca cctaagacag caacgacaag cgcgtagtga aacactggtg   480
taa                                                                 483
```

<210> SEQ ID NO 53
<211> LENGTH: 477
<212> TYPE: DNA
<213> ORGANISM: Human papillomavirus type 68

<400> SEQUENCE: 53

| | | | | | |
|---|---|---|---|---|---|
| atggcgctat | ttcacaaccc | tgaggaacgg | ccatacaaat | tgccagacct | gtgcaggaca | 60 |
| ttggacacta | cattgcatga | cgttacaata | gactgtgtct | attgcagaag | gcaactacaa | 120 |
| cggacagagg | tatatgaatt | tgcctttagt | gacctatgtg | tagtgtatag | agacggggta | 180 |
| ccatttgctg | catgccaatc | atgtattaaa | ttttatgcta | aaatacggga | actacgatat | 240 |
| tactcggaat | cggtgtatgc | aactacatta | gaaaccataa | ctaatacaaa | gttatataat | 300 |
| ttattgataa | ggtgcatgag | ttgcctgaaa | ccattgtgtc | cagcgaaaa | actaaggcac | 360 |
| ctaacaacaa | aacgaagatt | acataaaata | gcaggaaact | ttacaggaca | gtgtcggcac | 420 |
| tgctggacca | gtaagcgaga | ggaccgcaga | cgcatacgtc | aagaaacaca | agtttaa | 477 |

<210> SEQ ID NO 54
<211> LENGTH: 318
<212> TYPE: DNA
<213> ORGANISM: Human papillomavirus type 18

<400> SEQUENCE: 54

| | | | | | |
|---|---|---|---|---|---|
| atgcatggac | ctaaggcaac | attgcaagac | attgtattgc | atttagagcc | ccaaaatgaa | 60 |
| attccggttg | accttctatg | tcacgagcaa | ttaagcgact | cagaggaaga | aaacgatgaa | 120 |
| atagatgag | ttaatcatca | acatttacca | gcccgacgag | ccgaaccaca | acgtcacaca | 180 |
| atgttgtgta | tgtgttgtaa | gtgtgaagcc | agaattaagc | tagtagtaga | aagctcagca | 240 |
| gacgaccttc | gagcattcca | gcagctgttt | ctgaacaccc | tgtcctttgt | gtgtccgtgg | 300 |
| tgtgcatccc | agcagtaa | | | | | 318 |

<210> SEQ ID NO 55
<211> LENGTH: 297
<212> TYPE: DNA
<213> ORGANISM: Human papillomavirus type 31

<400> SEQUENCE: 55

| | | | | | |
|---|---|---|---|---|---|
| atgcgtggag | aaacacctac | gttgcaagac | tatgtgttag | atttgcaacc | tgaggcaact | 60 |
| gacctccact | gttatgagca | attacccgac | agctcagatg | aggaggatgt | catagacagt | 120 |
| ccagctggac | aagcagaacc | ggacacatcc | aattacaata | tcgttaccct | ttgttgtcag | 180 |
| tgtaagtcta | cacttcgttt | tgtgtgtacag | agcacacaag | tagatattcg | catattgcaa | 240 |
| gagctgttaa | tgggctcatt | tggaatcgtg | tgccccaact | gttctactag | actgtaa | 297 |

<210> SEQ ID NO 56
<211> LENGTH: 294
<212> TYPE: DNA
<213> ORGANISM: Human papillomavirus type 33

<400> SEQUENCE: 56

| | | | | | |
|---|---|---|---|---|---|
| atgagaggac | acaagccaac | gttaaaggaa | tatgttttag | atttatatcc | tgaaccaact | 60 |
| gacctatact | gctatgagca | attaagtgac | agctcagatg | aggatgaagg | cttggaccgg | 120 |
| ccagatggac | aagcacaacc | agccacagct | gattactaca | ttgtaacctg | ttgtcacact | 180 |
| tgtaacacca | cagttcgttt | atgtgtcaac | agtacagcaa | gtgacctacg | aaccatacag | 240 |
| caactactta | tgggcacagt | gaatattgtg | tgccctacct | gtgcacaaca | ataa | 294 |

```
<210> SEQ ID NO 57
<211> LENGTH: 300
<212> TYPE: DNA
<213> ORGANISM: Human papillomavirus type 35

<400> SEQUENCE: 57
atgcatggag aaataactac attgcaagac tatgttttag atttggaacc cgaggcaact      60
gacctatact gttatgagca attgtgtgac agctcagagg aggaggaaga tactattgac     120
ggtccagctg gacaagcaaa accagacacc tccaattata atattgtaac gtcctgttgt     180
aaatgtgagg cgacactacg tctgtgtgta cagagcacac acattgacat cgtaaattg      240 gaagatttat taatgggcac atttggaata gtgtgccccg gctgttcaca gagagcataa     300

<210> SEQ ID NO 58
<211> LENGTH: 330
<212> TYPE: DNA
<213> ORGANISM: Human papillomavirus type 39

<400> SEQUENCE: 58
atgcgtggac caaagcccac cttgcaggaa attgtattag atttatgtcc ttacaatgaa      60
atacagccgg ttgaccttgt atgtcacgag caattaggag agtcagagga tgaaatagat     120
gaacccgacc atgcagttaa tcaccaacat caactactag ccagacggga tgaaccacag     180
cgtcacacaa tacagtgttc gtgttgtaag tgtaacaaca cactgcagct ggtagtagaa     240
gcctcacggg atactctgcg acaactcag cagctgttta tggactcact aggatttgtg      300
tgtccgtggt gtgcaactgc aaaccagtaa                                      330

<210> SEQ ID NO 59
<211> LENGTH: 321
<212> TYPE: DNA
<213> ORGANISM: Human papillomavirus type 45

<400> SEQUENCE: 59
atgcatggac cccgggaaac actgcaagaa attgtattgc atttggaacc tcagaatgaa      60
ttagatcctg ttgacctgtt gtgttacgag caattaagcg agtcagagga ggaaaacgat     120
gaagcagatg gagttagtca tgcacaacta ccagcccgac gagccgaacc acagcgtcac     180
aaaattttgt gtgtatgttg taagtgtgac ggcagaattg agcttacagt agagagctcg     240
gcagaggacc ttagaacact acagcagctg tttttgagca ccttgtcctt tgtgtgtccg     300
tggtgtgcaa ctaaccaata a                                               321

<210> SEQ ID NO 60
<211> LENGTH: 306
<212> TYPE: DNA
<213> ORGANISM: Human papillomavirus type 51

<400> SEQUENCE: 60
atgcgtggta atgtaccaca attaaaagat gtagtattgc atttaacacc acagactgaa      60
attgacttgc aatgctacga gcaatttgac agctcagagg aggaggatga agtagataat     120
atgcgtgacc agctaccaga aagacgggct ggacaggcta cgtgttacag aattgaagct     180
ccgtgttgca ggtgttcaag tgtagtacaa ctggcagtgg aaagcagtgg agacacccttt    240 cgcgttgtac agcagatgtt aatgggcgaa ctaagcctgg tttgcccgtg ttgtgcgaac     300
aactag                                                                306
```

```
<210> SEQ ID NO 61
<211> LENGTH: 300
<212> TYPE: DNA
<213> ORGANISM: Human papillomavirus type 52

<400> SEQUENCE: 61
atgcgtggag acaaagcaac tataaaagat tatatattag atctgcaacc tgaaacaact      60
gacctacact gctatgagca attaggtgac agctcagatg aggaggatac agatggtgtg     120
gaccggccag atggacaagc agaacaagcc acaagcaatt actacattgt gacatattgt     180
cacagttgtg atagcacact acggctatgc attcatagca ctgcgacgga ccttcgtact     240
ctacagcaaa tgctgttggg cacattacaa gttgtgtgcc ccggctgtgc acggctataa     300

<210> SEQ ID NO 62
<211> LENGTH: 318
<212> TYPE: DNA
<213> ORGANISM: Human papillomavirus type 56

<400> SEQUENCE: 62
atgcatggta aagtaccaac gctgcaagac gttgtattag aactaacacc tcaaacagaa      60
attgacctac agtgcaatga gcaattggac agctcagagg atgaggatga ggatgaagta     120
gaccatttgc aggagcggcc acagcaagct agacaagcta acaacatac gtgttaccta     180 atacacgtac cttgttgtga gtgtaagttt gtggtgcagt tggacattca gagtaccaaa     240
gaggacctgc gtgttgtaca acagctgctt atgggtgcgt taacagtaac gtgcccactc     300
tgcgcatcaa gtaactaa                                                   318

<210> SEQ ID NO 63
<211> LENGTH: 297
<212> TYPE: DNA
<213> ORGANISM: Human papillomavirus type 58

<400> SEQUENCE: 63
atgagaggaa acaacccaac gctaagagaa tatattttag atttacatcc tgaaccaact      60
gacctattct gctatgagca attatgtgac agctcagacg aggatgaaat aggcttggac     120
gggccagatg acaagcaca accggccaca gctaattact acattgtaac ttgttgttac     180
acttgtggca ccacgttcg tttgtgtatc aacagtacaa caccgacgt acgaacccta     240 cagcagctgc ttatgggcac atgtaccatt gtgtgcccta gctgtgcaca gcaataa       297

<210> SEQ ID NO 64
<211> LENGTH: 324
<212> TYPE: DNA
<213> ORGANISM: Human papillomavirus type 59

<400> SEQUENCE: 64
atgcatggac caaaagcaac actttgtgac attgttttag atttggaacc acaaaattat      60
gaggaagttg accttgtgtg ctacgagcaa ttacctgact ccgactccga gaatgaaaaa     120
gatgaaccag atggagttaa tcatcctttg ctactagcta gacgagctga accacagcgt     180
cacaacattg tgtgtgtgtg ttgtaagtgt aataatcaac ttcagctagt agtagaaacc     240
tcgcaagacg gattgcgagc cttcagcag ctgtttatgg acacactatc ctttgtgtgt     300
cctttgtgtg cagcaaaacca gtaa                                           324

<210> SEQ ID NO 65
<211> LENGTH: 333
<212> TYPE: DNA
```

```
<213> ORGANISM: Human papillomavirus type 68

<400> SEQUENCE: 65
atgcatggac caaagcccac cgtgcaggaa attgtgttag agctatgtcc atacaatgaa      60
atacagccgg ttgaccttgt atgtcacgag caattaggag attcagacga tgaaatagat     120
gaacccgacc atgcagttaa tcaccaccaa catctactac tagccagacg ggacgaacaa     180
cagcgtcaca gaattcagtg tctgtgttgt aagtgtaaca aggcactgca actagtagta     240
gaagcgtcgc gggacaacct gcggacacta caacagctgt ttatggactc actaaatttt     300
gtgtgtccgt ggtgtgcaac tgaaacccag taa                                  333
```